US012352761B2

(12) United States Patent
Sitbon et al.

(10) Patent No.: US 12,352,761 B2
(45) Date of Patent: Jul. 8, 2025

(54) USE OF LIGANDS DERIVED FROM RECEPTOR-BINDING DOMAIN OF PORCINE ENDOGENOUS RETROVIRUS TYPE B FOR DIAGNOSING SMVT-RELATED DISEASES

(71) Applicants: METAFORA BIOSYSTEMS, Paris (FR); CENTRE NATIONAL DE LA RECHERCHE SCIENTIFIQUE, Paris (FR); UNIVERSITÉ DE MONTPELLIER, Montpellier (FR); UNIVERSITÉ DE PARIS, Paris (FR)

(72) Inventors: Marc Sitbon, Montpellier (FR); Vincent Petit, Paris (FR); Svilena Ivanova, Neuchâtel (CH); Jean-Luc Battini, Montpellier (FR); Valérie Courgnaud, Montpellier (FR); Donatella Giovannini, Montpellier (FR); Jawida Lezaar, Montpellier (FR)

(73) Assignees: METAFORA BIOSYSTEMS, Paris (FR); CENTRE NATIONAL DE LA RECHERCHE SCIENTIFIQUE, Paris (FR); UNIVERSITÉ DE MONTPELLIER, Montpellier (FR); UNIVERSITÉ PARIS CITÉ, Paris (FR)

( * ) Notice: Subject to any disclaimer, the term of this patent is extended or adjusted under 35 U.S.C. 154(b) by 1105 days.

(21) Appl. No.: 17/282,150

(22) PCT Filed: Oct. 7, 2019

(86) PCT No.: PCT/EP2019/077078
§ 371 (c)(1),
(2) Date: Apr. 1, 2021

(87) PCT Pub. No.: WO2020/070330
PCT Pub. Date: Apr. 9, 2020

(65) Prior Publication Data
US 2022/0003782 A1   Jan. 6, 2022

(30) Foreign Application Priority Data
Oct. 5, 2018   (EP) .................................... 18306319

(51) Int. Cl.
*A61K 49/00*   (2006.01)
*G01N 33/68*   (2006.01)
*C07K 14/08*   (2006.01)

(52) U.S. Cl.
CPC ......... *G01N 33/6872* (2013.01); *A61K 49/00* (2013.01); *C07K 14/08* (2013.01); *G01N 2333/15* (2013.01)

(58) Field of Classification Search
None
See application file for complete search history.

(56) References Cited

U.S. PATENT DOCUMENTS 7,842,291 B1   11/2010   Ruben et al.

FOREIGN PATENT DOCUMENTS

| WO | 2004/096841 A1 | 11/2004 |
|---|---|---|
| WO | 2010/079208 A1 | 7/2010 |
| WO | 2012/035166 A1 | 3/2012 |
| WO | 2013/060893 A1 | 5/2013 |
| WO | 2015/110606 A1 | 7/2015 |
| WO | 2017/085271 A1 | 5/2017 |

OTHER PUBLICATIONS

Whisstock et al., (Quarterly Reviews of Biophysics 2003, vol. 36 (3): 307-340,).*
Witowski et al., (Biochemistry 38:11643-11650, 1999).*
Kisselev L., (Structure, 2002, vol. 10: 8-9).*
Devos et al., (Proteins: Structure, Function and Genetics, 2000, vol. 41: 98-107).*
Mikayama et al. (Nov. 1993. Proc.Natl.Acad.Sci. USA, vol. 90 : 10056-10060).*
International Search Report issued on Jan. 15, 2020, in connection with corresponding International Application No. PCT/EP2019/077078; 6 pages.
Wang, et al., "Human Placental Na+-dependent Multivitamin Transporter. Cloning, functional expression, gene structure, and chromosomal localization", Journal of Biological Chemistry, May 21, 1999, vol. 274, No. 21, pp. 14875-14883 (9 pp.,), doi: 10.1074/jbc.274.21.14875.
Prasad, et al., "Cloning and Functional Expression of a cDNA Encoding a Mammalian Sodium-dependent Vitamin Transporter Mediating the Uptake of Pantothenate, Biotin, and Lipoate", Journal of Biological Chemistry, Mar. 27, 1998, vol. 273, No. 13, pp. 7501-7506 (6 pp.), doi: 10.1074/jbc.273.13.7501.
Subramanian et al., "Mutations in SLC5A6 associated with brain, immune, bone, and intestinal dysfunction in a young child", HHS Public Access Author Manuscript, Human Genetics, Feb. 2017, vol. 136, No. 2, 18 pp., doi: 10.1007/s00439-016-1751-x.
Quick et al., "The Sodium/Multivitamin Transporter: a Multipotent System with Therapeutic Implications", HHS Public Access Author Manuscript, Vitamins and Hormones, 2015, vol. 98, 35 pp., doi: 10.1016/bs.vh.2014.12.003.
Ghosal et al., "*Salmonella* infection inhibits intestinal biotin transport: cellular and molecular mechanisms", American Journal of Physiology—Gastrointestinal and Liver Physiology, Jul. 15, 2015, vol. 309, No. 2, G123-131 (9 pp.), doi: 10.1152/ajpgi.00112.2015.
Provenzani et al., "Global alterations in mRNA polysomal recruitment in a cell model of colorectal cancer progression to metastasis", Carcinogenesis, Jul. 2006, vol. 27, No. 7, pp. 1323-1333 (11 pp.), doi: 10.1093/carcin/bgi377.

(Continued)

*Primary Examiner* — Jennifer E Graser
(74) *Attorney, Agent, or Firm* — Maier & Maier, PLLC

(57) ABSTRACT

Methods for detecting and/or measuring the level of sodium-dependent multivitamin transporter (SMVT) in a biological sample. The methods include the steps of: (a) contacting the biological sample with a PERV-B.RBD ligand, a variant and/or a fragment thereof; and, detecting and/or measuring the binding of the PERV-B.RBD ligand, variant and/or fragment thereof to SMVT.

14 Claims, 2 Drawing Sheets

Specification includes a Sequence Listing.

(56) References Cited

OTHER PUBLICATIONS

Sissung et al., "Identification of novel SNPs associated with risk and prognosis in patients with castration-resistant prostate cancer", Pharmacogenomics, Dec. 2016, vol. 17, No. 18; pp. 1979-1986 (8 pp.), doi: 10.2217/pgs-2016-0134.

Leithner et al., "TASK-1 Regulates Apoptosis and Proliferation in a Subset of Non-Small Cell Lung Cancers", PLoS One, Jun. 13, 2016, vol. 11, No. 6, Article e0157453 (18 pp.), doi: 10.1371/journal.pone.0157453.

Pita et al., "Cell Cycle Deregulation and TP53 and RAS Mutations Are Major Events in Poorly Differentiated and Undifferentiated Thyroid Carcinomas", Journal of Clinical Endocrinology and Metabolism, Mar. 2014, vol. 99, No. 3, E497-507 (11 pp.), doi: 10.1210/jc.2013-1512.

Vadlapudi et al., "Sodium Dependent Multivitamin Transporter (SMVT): A Potential Target for Drug Delivery", HHS Public Access Author Manuscript, Current Drug Targets, Jun. 2012, vol. 13, No. 7, 21 pp., doi: 10.2174/138945012800675650.

Griffin et al., "Computer Analysis of Sequence Data, Parts I and II," 1994, Humana Press, New Jersey, Journal of Evolutionary Biology, 7: 628-629.

Devereux et al., "A comprehensive set of sequence analysis programs for the VAX," Nucleic Acids Research, Jan. 11, 1984, vol. 12, No. 1 Pt 1, pp. 387-395 (9 pp.), doi: 10.1093/nar/12.1part1.387.

Altschul et al., "Basic Local Alignment Search Tool", Journal of Molecular Biology, Oct. 5, 1990, vol. 215, No. 3, pp. 403-410 (8 pp.), doi: 10.1016/S0022-2836(05)80360-2.

Krupovic et al., "Ortervirales: New Virus Order Unifying Five Families of Reverse-Transcribing Viruses", Journal of Virology, May 29, 2018, vol. 92, No. 12, e00515-18 (5 pp.), doi: 10.1128/JVI.00515-18.

Schwantje et al., "Genetic defect of the sodium-dependent multivitamin transporter: A treatable disease, mimicking piotinidase deficiency", JIMD Reports, May 28, 2019, vol. 48, No. 1, pp. 11-14 (4 pp.), doi: 10.1002/jmd2.12040.

Boonstra et al., "uPAR-targeted multimodal tracer for pre- and intraoperative imaging in cancer surgery", Oncotarget, Jun. 10, 2015, vol. 6, No. 16, pp. 14260-14273 (14 pp.), doi: 10.18632/oncotarget.3680.

Watanabe et al., "Effects of biotin deficiency on embryonic development in mice", Nutrition, Jan. 2009, vol. 25, No. 1, pp. 78-84 (7 pp.), doi: 10.1016/j.nut.2008.06.031.

Buys et al., "Genetic Changes in the Evolution of Multidrug Resistance for Cultured Human Ovarian Cancer Cells", Genes Chromosomes & Cancer, Dec. 2007, vol. 46, No. 12, pp. 1069-1079 (11 pp.), doi: 10.1002/gcc.20492.

* cited by examiner

SEQUENCE LISTING

```
<160> NUMBER OF SEQ ID NOS: 27

<210> SEQ ID NO 1
<211> LENGTH: 635
<212> TYPE: PRT
<213> ORGANISM: Homo sapiens
<220> FEATURE:
<223> OTHER INFORMATION: human sodium-dependent multivitamin
      transporter - SLC5A6

<400> SEQUENCE: 1

Met Ser Val Gly Val Ser Thr Ser Ala Pro Leu Ser Pro Thr Ser Gly
1               5                   10                  15

Thr Ser Val Gly Met Ser Thr Phe Ser Ile Met Asp Tyr Val Val Phe
            20                  25                  30

Val Leu Leu Leu Val Leu Ser Leu Ala Ile Gly Leu Tyr His Ala Cys
        35                  40                  45

Arg Gly Trp Gly Arg His Thr Val Gly Glu Leu Leu Met Ala Asp Arg
    50                  55                  60

Lys Met Gly Cys Leu Pro Val Ala Leu Ser Leu Leu Ala Thr Phe Gln
65                  70                  75                  80

Ser Ala Val Ala Ile Leu Gly Val Pro Ser Glu Ile Tyr Arg Phe Gly
                85                  90                  95

Thr Gln Tyr Trp Phe Leu Gly Cys Cys Tyr Phe Leu Gly Leu Leu Ile
            100                 105                 110

Pro Ala His Ile Phe Ile Pro Val Phe Tyr Arg Leu His Leu Thr Ser
        115                 120                 125

Ala Tyr Glu Tyr Leu Glu Leu Arg Phe Asn Lys Thr Val Arg Val Cys
    130                 135                 140

Gly Thr Val Thr Phe Ile Phe Gln Met Val Ile Tyr Met Gly Val Val
145                 150                 155                 160

Leu Tyr Ala Pro Ser Leu Ala Leu Asn Ala Val Thr Gly Phe Asp Leu
                165                 170                 175

Trp Leu Ser Val Leu Ala Leu Gly Ile Val Cys Thr Val Tyr Thr Ala
```

```
            180                 185                 190
Leu Gly Gly Leu Lys Ala Val Ile Trp Thr Asp Val Phe Gln Thr Leu
            195                 200                 205
Val Met Phe Leu Gly Gln Leu Ala Val Ile Val Gly Ser Ala Lys
    210                 215                 220
Val Gly Gly Leu Gly Arg Val Trp Ala Val Ala Ser Gln His Gly Arg
225                 230                 235                 240
Ile Ser Gly Phe Glu Leu Asp Pro Asp Pro Phe Val Arg His Thr Phe
                245                 250                 255
Trp Thr Leu Ala Phe Gly Gly Val Phe Met Met Leu Ser Leu Tyr Gly
                260                 265                 270
Val Asn Gln Ala Gln Val Gln Arg Tyr Leu Ser Ser Arg Thr Glu Lys
                275                 280                 285
Ala Ala Val Leu Ser Cys Tyr Ala Val Phe Pro Phe Gln Gln Val Ser
                290                 295                 300
Leu Cys Val Gly Cys Leu Ile Gly Leu Val Met Phe Ala Tyr Tyr Gln
305                 310                 315                 320
Glu Tyr Pro Met Ser Ile Gln Gln Ala Gln Ala Ala Pro Asp Gln Phe
                325                 330                 335
Val Leu Tyr Phe Val Met Asp Leu Leu Lys Gly Leu Pro Gly Leu Pro
                340                 345                 350
Gly Leu Phe Ile Ala Cys Leu Phe Ser Gly Ser Leu Ser Thr Ile Ser
                355                 360                 365
Ser Ala Phe Asn Ser Leu Ala Thr Val Thr Met Glu Asp Leu Ile Arg
        370                 375                 380
Pro Trp Phe Pro Glu Phe Ser Glu Ala Arg Ala Ile Met Leu Ser Arg
385                 390                 395                 400
Gly Leu Ala Phe Gly Tyr Gly Leu Leu Cys Leu Gly Met Ala Tyr Ile
                405                 410                 415
Ser Ser Gln Met Gly Pro Val Leu Gln Ala Ala Ile Ser Ile Phe Gly
                420                 425                 430
Met Val Gly Gly Pro Leu Leu Gly Leu Phe Cys Leu Gly Met Phe Phe
        435                 440                 445
Pro Cys Ala Asn Pro Pro Gly Ala Val Val Gly Leu Leu Ala Gly Leu
    450                 455                 460
Val Met Ala Phe Trp Ile Gly Ile Gly Ser Ile Val Thr Ser Met Gly
465                 470                 475                 480
Ser Ser Met Pro Pro Ser Pro Ser Asn Gly Ser Ser Phe Ser Leu Pro
                485                 490                 495
Thr Asn Leu Thr Val Ala Thr Val Thr Thr Leu Met Pro Leu Thr Thr
                500                 505                 510
Phe Ser Lys Pro Thr Gly Leu Gln Arg Phe Tyr Ser Leu Ser Tyr Leu
                515                 520                 525
Trp Tyr Ser Ala His Asn Ser Thr Thr Val Ile Val Gly Leu Ile
                530                 535                 540
Val Ser Leu Leu Thr Gly Arg Met Arg Gly Arg Ser Leu Asn Pro Ala
545                 550                 555                 560
Thr Ile Tyr Pro Val Leu Pro Lys Leu Leu Ser Leu Leu Pro Leu Ser
                565                 570                 575
Cys Gln Lys Arg Leu His Cys Arg Ser Tyr Gly Gln Asp His Leu Asp
                580                 585                 590
Thr Gly Leu Phe Pro Glu Lys Pro Arg Asn Gly Val Leu Gly Asp Ser
                595                 600                 605
```

```
Arg Asp Lys Glu Ala Met Ala Leu Asp Gly Thr Ala Tyr Gln Gly Ser
        610                 615                 620

Ser Ser Thr Cys Ile Leu Gln Glu Thr Ser Leu
625                 630                 635

<210> SEQ ID NO 2
<211> LENGTH: 548
<212> TYPE: PRT
<213> ORGANISM: Porcine endogenous retrovirus B
<220> FEATURE:
<223> OTHER INFORMATION: porcine endogenous retrovirus type B envelope
      protein AAQ88198.1

<400> SEQUENCE: 2

Met His Pro Thr Leu Ser Trp Arg His Leu Pro Thr Arg Gly Gly Glu
1               5                   10                  15

Pro Lys Arg Leu Arg Ile Pro Leu Ser Phe Ala Ser Ile Ala Trp Phe
            20                  25                  30

Leu Thr Leu Thr Ile Thr Pro Gln Ala Ser Ser Lys Arg Leu Ile Asp
        35                  40                  45

Ser Ser Asn Pro His Arg Pro Leu Ser Leu Thr Trp Leu Ile Ile Asp
50                  55                  60

Pro Asp Thr Gly Val Thr Val Asn Ser Thr Arg Gly Val Ala Pro Arg
65                  70                  75                  80

Gly Thr Trp Trp Pro Glu Leu His Phe Cys Leu Arg Leu Ile Asn Pro
                85                  90                  95

Ala Val Lys Ser Thr Pro Pro Asn Leu Val Arg Ser Tyr Gly Phe Tyr
            100                 105                 110

Cys Cys Pro Gly Thr Glu Lys Glu Lys Tyr Cys Gly Gly Ser Glu Glu
        115                 120                 125

Ser Phe Cys Arg Arg Trp Ser Cys Val Thr Ser Asn Asp Gly Asp Trp
130                 135                 140

Lys Trp Pro Ile Ser Leu Gln Asp Arg Val Lys Phe Ser Phe Val Asn
145                 150                 155                 160

Ser Gly Pro Gly Lys Tyr Lys Val Met Lys Leu Tyr Lys Asp Lys Ser
                165                 170                 175

Cys Ser Pro Ser Asp Leu Asp Tyr Leu Lys Ile Ser Phe Thr Glu Lys
            180                 185                 190

Gly Lys Gln Glu Asn Ile Gln Lys Trp Ile Asn Gly Met Ser Trp Gly
        195                 200                 205

Ile Val Phe Tyr Lys Tyr Gly Gly Ala Gly Ser Thr Leu Thr Ile
210                 215                 220

Arg Leu Arg Ile Glu Thr Gly Thr Glu Pro Val Ala Val Gly Pro
225                 230                 235                 240

Asp Lys Val Leu Ala Glu Gln Gly Pro Pro Ala Leu Glu Pro Pro His
            245                 250                 255

Asn Leu Pro Val Pro Gln Leu Ser Leu Arg Pro Asp Ile Thr Gln
            260                 265                 270

Pro Pro Ser Asn Gly Thr Thr Gly Leu Ile Pro Thr Asn Thr Pro Arg
        275                 280                 285

Asn Ser Pro Gly Val Pro Val Lys Thr Gly Gln Arg Leu Phe Ser Leu
        290                 295                 300

Ile Gln Gly Ala Phe Gln Ala Ile Asn Ser Thr Asp Pro Asp Ala Thr
305                 310                 315                 320

Ser Ser Cys Trp Leu Cys Leu Ser Ser Gly Pro Pro Tyr Tyr Glu Gly
```

```
                            325                 330                 335

Met Ala Lys Glu Gly Lys Phe Asn Val Thr Lys Glu His Arg Asn Gln
            340                 345                 350

Cys Thr Trp Gly Ser Arg Asn Lys Leu Thr Leu Thr Glu Val Ser Gly
            355                 360                 365

Lys Gly Thr Cys Ile Gly Lys Ala Pro Pro Ser His Gln His Leu Cys
            370                 375                 380

Tyr Ser Thr Val Val Tyr Glu Gln Ala Ser Glu Asn Gln Tyr Leu Val
385                 390                 395                 400

Pro Gly Tyr Asn Arg Trp Trp Ala Cys Asn Thr Gly Leu Pro Pro Cys
                405                 410                 415

Val Ser Ser Val Phe Asn Gln Ser Lys Asp Phe Cys Val Met Val
                420                 425                 430

Gln Ile Val Pro Arg Val Tyr Tyr His Pro Glu Glu Val Val Leu Asp
                435                 440                 445

Glu Tyr Asp Tyr Arg Tyr Asn Arg Pro Lys Arg Glu Pro Val Ser Leu
450                 455                 460

Thr Leu Ala Val Met Leu Gly Leu Gly Thr Ala Val Gly Val Gly Thr
465                 470                 475                 480

Gly Thr Ala Ala Leu Ile Thr Gly Pro Gln Gln Leu Glu Lys Gly Leu
                485                 490                 495

Gly Glu Leu His Ala Ala Met Thr Glu Asp Leu Arg Ala Leu Glu Glu
                500                 505                 510

Ser Val Ser Asn Leu Glu Glu Ser Leu Thr Ser Leu Ser Glu Val Val
                515                 520                 525

Leu Gln Asn Arg Arg Gly Leu Asp Leu Leu Phe Leu Arg Glu Gly Gly
                530                 535                 540

Leu Cys Ala Ala
545

<210> SEQ ID NO 3
<211> LENGTH: 43
<212> TYPE: PRT
<213> ORGANISM: Artificial Sequence
<220> FEATURE:
<223> OTHER INFORMATION: PERV-B Env protein signal peptide

<400> SEQUENCE: 3

Met His Pro Thr Leu Ser Trp Arg His Leu Pro Thr Arg Gly Gly Glu
1               5                   10                  15

Pro Lys Arg Leu Arg Ile Pro Leu Ser Phe Ala Ser Ile Ala Trp Phe
            20                  25                  30

Leu Thr Leu Thr Ile Thr Pro Gln Ala Ser Ser
        35                  40

<210> SEQ ID NO 4
<211> LENGTH: 459
<212> TYPE: PRT
<213> ORGANISM: Artificial Sequence
<220> FEATURE:
<223> OTHER INFORMATION: Porcine endogenous retrovirus type B SU protein

<400> SEQUENCE: 4

Met His Pro Thr Leu Ser Trp Arg His Leu Pro Thr Arg Gly Gly Glu
1               5                   10                  15

Pro Lys Arg Leu Arg Ile Pro Leu Ser Phe Ala Ser Ile Ala Trp Phe
            20                  25                  30
```

-continued

Leu Thr Leu Thr Ile Thr Pro Gln Ala Ser Ser Lys Arg Leu Ile Asp
        35                  40                  45

Ser Ser Asn Pro His Arg Pro Leu Ser Leu Thr Trp Leu Ile Ile Asp
50                  55                  60

Pro Asp Thr Gly Val Thr Val Asn Ser Thr Arg Gly Val Ala Pro Arg
65                  70                  75                  80

Gly Thr Trp Trp Pro Glu Leu His Phe Cys Leu Arg Leu Ile Asn Pro
                85                  90                  95

Ala Val Lys Ser Thr Pro Pro Asn Leu Val Arg Ser Tyr Gly Phe Tyr
            100                 105                 110

Cys Cys Pro Gly Thr Glu Lys Glu Lys Tyr Cys Gly Gly Ser Glu Glu
            115                 120                 125

Ser Phe Cys Arg Arg Trp Ser Cys Val Thr Ser Asn Asp Gly Asp Trp
    130                 135                 140

Lys Trp Pro Ile Ser Leu Gln Asp Arg Val Lys Phe Ser Phe Val Asn
145                 150                 155                 160

Ser Gly Pro Gly Lys Tyr Lys Val Met Lys Leu Tyr Lys Asp Lys Ser
                165                 170                 175

Cys Ser Pro Ser Asp Leu Asp Tyr Leu Lys Ile Ser Phe Thr Glu Lys
            180                 185                 190

Gly Lys Gln Glu Asn Ile Gln Lys Trp Ile Asn Gly Met Ser Trp Gly
            195                 200                 205

Ile Val Phe Tyr Lys Tyr Gly Gly Ala Gly Ser Thr Leu Thr Ile
    210                 215                 220

Arg Leu Arg Ile Glu Thr Gly Thr Glu Pro Pro Val Ala Val Gly Pro
225                 230                 235                 240

Asp Lys Val Leu Ala Glu Gln Gly Pro Pro Ala Leu Glu Pro Pro His
            245                 250                 255

Asn Leu Pro Val Pro Gln Leu Thr Ser Leu Arg Pro Asp Ile Thr Gln
            260                 265                 270

Pro Pro Ser Asn Gly Thr Thr Gly Leu Ile Pro Thr Asn Thr Pro Arg
            275                 280                 285

Asn Ser Pro Gly Val Pro Val Lys Thr Gly Gln Arg Leu Phe Ser Leu
    290                 295                 300

Ile Gln Gly Ala Phe Gln Ala Ile Asn Ser Thr Asp Pro Asp Ala Thr
305                 310                 315                 320

Ser Ser Cys Trp Leu Cys Leu Ser Ser Gly Pro Pro Tyr Tyr Glu Gly
                325                 330                 335

Met Ala Lys Glu Gly Lys Phe Asn Val Thr Lys Glu His Arg Asn Gln
            340                 345                 350

Cys Thr Trp Gly Ser Arg Asn Lys Leu Thr Leu Thr Glu Val Ser Gly
            355                 360                 365

Lys Gly Thr Cys Ile Gly Lys Ala Pro Pro Ser His Gln His Leu Cys
    370                 375                 380

Tyr Ser Thr Val Val Tyr Glu Gln Ala Ser Glu Asn Gln Tyr Leu Val
385                 390                 395                 400

Pro Gly Tyr Asn Arg Trp Trp Ala Cys Asn Thr Gly Leu Pro Pro Cys
                405                 410                 415

Val Ser Ser Ser Val Phe Asn Gln Ser Lys Asp Phe Cys Val Met Val
            420                 425                 430

Gln Ile Val Pro Arg Val Tyr Tyr His Pro Glu Glu Val Val Leu Asp
            435                 440                 445

Glu Tyr Asp Tyr Arg Tyr Asn Arg Pro Lys Arg

<210> SEQ ID NO 5
<211> LENGTH: 238
<212> TYPE: PRT
<213> ORGANISM: Artificial Sequence
<220> FEATURE:
<223> OTHER INFORMATION: RBD domain of the PERV-B.RBD ligand

<400> SEQUENCE: 5

```
Met His Pro Thr Leu Ser Trp Arg His Leu Pro Thr Arg Gly Gly Glu
1               5                   10                  15

Pro Lys Arg Leu Arg Ile Pro Leu Ser Phe Ala Ser Ile Ala Trp Phe
            20                  25                  30

Leu Thr Leu Thr Ile Thr Pro Gln Ala Ser Ser Lys Arg Leu Ile Asp
        35                  40                  45

Ser Ser Asn Pro His Arg Pro Leu Ser Leu Thr Trp Leu Ile Ile Asp
    50                  55                  60

Pro Asp Thr Gly Val Thr Val Asn Ser Thr Arg Gly Val Ala Pro Arg
65                  70                  75                  80

Gly Thr Trp Trp Pro Glu Leu His Phe Cys Leu Arg Leu Ile Asn Pro
                85                  90                  95

Ala Val Lys Ser Thr Pro Pro Asn Leu Val Arg Ser Tyr Gly Phe Tyr
            100                 105                 110

Cys Cys Pro Gly Thr Glu Lys Glu Lys Tyr Cys Gly Gly Ser Glu Glu
        115                 120                 125

Ser Phe Cys Arg Arg Trp Ser Cys Val Thr Ser Asn Asp Gly Asp Trp
    130                 135                 140

Lys Trp Pro Ile Ser Leu Gln Asp Arg Val Lys Phe Ser Phe Val Asn
145                 150                 155                 160

Ser Gly Pro Gly Lys Tyr Lys Val Met Lys Leu Tyr Lys Asp Lys Ser
                165                 170                 175

Cys Ser Pro Ser Asp Leu Asp Tyr Leu Lys Ile Ser Phe Thr Glu Lys
            180                 185                 190

Gly Lys Gln Glu Asn Ile Gln Lys Trp Ile Asn Gly Met Ser Trp Gly
        195                 200                 205

Ile Val Phe Tyr Lys Tyr Gly Gly Gly Ala Gly Ser Thr Leu Thr Ile
    210                 215                 220

Arg Leu Arg Ile Glu Ala Gly Thr Glu Pro Pro Val Ala Val
225                 230                 235
```

<210> SEQ ID NO 6
<211> LENGTH: 195
<212> TYPE: PRT
<213> ORGANISM: Artificial Sequence
<220> FEATURE:
<223> OTHER INFORMATION: PERV-B.RBD domain without signal peptide

<400> SEQUENCE: 6

```
Lys Arg Leu Ile Asp Ser Ser Asn Pro His Arg Pro Leu Ser Leu Thr
1               5                   10                  15

Trp Leu Ile Ile Asp Pro Asp Thr Gly Val Thr Val Asn Ser Thr Arg
            20                  25                  30

Gly Val Ala Pro Arg Gly Thr Trp Trp Pro Glu Leu His Phe Cys Leu
        35                  40                  45

Arg Leu Ile Asn Pro Ala Val Lys Ser Thr Pro Pro Asn Leu Val Arg
    50                  55                  60
```

-continued

```
Ser Tyr Gly Phe Tyr Cys Cys Pro Gly Thr Glu Lys Glu Lys Tyr Cys
65                  70                  75                  80

Gly Gly Ser Glu Glu Ser Phe Cys Arg Arg Trp Ser Cys Val Thr Ser
                85                  90                  95

Asn Asp Gly Asp Trp Lys Trp Pro Ile Ser Leu Gln Asp Arg Val Lys
            100                 105                 110

Phe Ser Phe Val Asn Ser Gly Pro Gly Lys Tyr Lys Val Met Lys Leu
        115                 120                 125

Tyr Lys Asp Lys Ser Cys Ser Pro Ser Asp Leu Asp Tyr Leu Lys Ile
    130                 135                 140

Ser Phe Thr Glu Lys Gly Lys Gln Glu Asn Ile Gln Lys Trp Ile Asn
145                 150                 155                 160

Gly Met Ser Trp Gly Ile Val Phe Tyr Lys Tyr Gly Gly Gly Ala Gly
                165                 170                 175

Ser Thr Leu Thr Ile Arg Leu Arg Ile Glu Ala Gly Thr Glu Pro Pro
            180                 185                 190

Val Ala Val
        195
```

<210> SEQ ID NO 7
<211> LENGTH: 714
<212> TYPE: DNA
<213> ORGANISM: Artificial Sequence
<220> FEATURE:
<223> OTHER INFORMATION: coding sequence for PERV-B.RDB RBD domain

<400> SEQUENCE: 7

```
atgcatccca cgttaagctg gcgccacctc ccgactcggg gtggagagcc gaaaagactg     60
agaatcccct taagcttcgc ctccatcgcc tggttcctta ctctaacaat aactccccag    120
gccagtagta aacgccttat agacagctcg aacccccata gacctttatc ccttacctgg    180
ctgattattg accctgatac gggtgtcact gtaaatagca ctcgaggtgt tgctcctaga    240
ggcacctggt ggcctgaact gcatttctgc ctccgattga ttaaccccgc tgttaaaagc    300
acacctccca acctagtccg tagttatggg ttctattgct gcccaggcac agagaaagag    360
aaatactgtg gggttctga ggaatccttc tgtaggagat ggagctgcgt cacctccaac    420
gatggagact ggaaatggcc gatctctctc caggaccggg taaaattctc ctttgtcaat    480
tccggcccgg gcaagtacaa agtgatgaaa ctatataaag ataagagctg ctccccatca    540
gacttagatt atctaaagat aagtttcact gaaaaaggaa aacaggaaaa tattcaaaag    600
tggataaatg gtatgagctg ggaatagtt ttttataaat atggcggggg agcagggtcc    660
actttaacca ttcgccttag gatagaggcg gggacagaac cccctgtggc agtg          714
```

<210> SEQ ID NO 8
<211> LENGTH: 585
<212> TYPE: DNA
<213> ORGANISM: Artificial Sequence
<220> FEATURE:
<223> OTHER INFORMATION: coding sequence for PERV-B.RBD domain without signal peptide

<400> SEQUENCE: 8

```
aaacgcctta tagacagctc gaacccccat agacctttat cccttacctg gctgattatt     60
gaccctgata cgggtgtcac tgtaaatagc actcgaggtg ttgctcctag aggcacctgg    120
tggcctgaac tgcatttctg cctccgattg attaaccccg ctgttaaaag cacacctccc    180
aacctagtcc gtagttatgg gttctattgc tgcccaggca cagagaaaga gaaatactgt    240
```

```
ggggggttctg aggaatcctt ctgtaggaga tggagctgcg tcacctccaa cgatggagac      300
tggaaatggc cgatctctct ccaggaccgg gtaaaattct cctttgtcaa ttccggcccg      360
ggcaagtaca aagtgatgaa actatataaa gataagagct gctccccatc agacttagat      420
tatctaaaga taagttttcac tgaaaaagga aaacaggaaa atattcaaaa gtggataaat      480
ggtatgagct ggggaatagt tttttataaa tatggcgggg gagcagggtc cactttaacc      540
attcgcctta ggatagaggc ggggacagaa ccccctgtgg cagtg                     585
```

<210> SEQ ID NO 9
<211> LENGTH: 228
<212> TYPE: PRT
<213> ORGANISM: Artificial Sequence
<220> FEATURE:
<223> OTHER INFORMATION: FC fragment

<400> SEQUENCE: 9

```
Ala Pro Ser Thr Cys Ser Lys Pro Thr Cys Pro Pro Glu Leu Leu
1               5                   10                  15

Gly Gly Pro Ser Val Phe Ile Phe Pro Pro Lys Pro Lys Asp Thr Leu
                20                  25                  30

Met Ile Ser Arg Thr Pro Glu Val Thr Cys Val Val Asp Val Ser
            35                  40                  45

Gln Asp Asp Pro Glu Val Gln Phe Thr Trp Tyr Ile Asn Asn Glu Gln
50                  55                  60

Val Arg Thr Ala Arg Pro Pro Leu Arg Glu Gln Gln Phe Asp Cys Thr
65                  70                  75                  80

Ile Arg Val Val Ser Thr Leu Pro Ile Ala His Gln Asp Trp Leu Arg
                85                  90                  95

Gly Lys Glu Phe Lys Cys Lys Val His Asn Lys Ala Leu Pro Ala Pro
                100                 105                 110

Ile Glu Lys Thr Ile Ser Lys Ala Arg Gly Gln Pro Leu Glu Pro Lys
            115                 120                 125

Val Tyr Thr Met Gly Pro Pro Arg Glu Glu Leu Ser Ser Arg Ser Val
        130                 135                 140

Ser Leu Thr Cys Met Ile Asn Gly Phe Tyr Pro Ser Asp Ile Ser Val
145                 150                 155                 160

Glu Trp Glu Lys Asn Gly Lys Ala Glu Asp Asn Tyr Lys Thr Thr Pro
                165                 170                 175

Ala Val Leu Asp Ser Asp Gly Ser Tyr Phe Leu Tyr Ser Lys Leu Ser
            180                 185                 190

Val Pro Thr Ser Glu Trp Gln Arg Gly Asp Val Phe Thr Cys Ser Val
        195                 200                 205

Met His Glu Ala Leu His Asn His Tyr Thr Gln Lys Ser Ile Ser Arg
    210                 215                 220

Ser Pro Gly Lys
225
```

<210> SEQ ID NO 10
<211> LENGTH: 687
<212> TYPE: DNA
<213> ORGANISM: Artificial Sequence
<220> FEATURE:
<223> OTHER INFORMATION: DNA coding sequence for the rabbit Fc fragment

<400> SEQUENCE: 10

```
gcaccctcga catgcagcaa gcccacgtgc ccaccccctg aactcctggg gggaccgtct      60
```

```
gtcttcatct tcccccccaaa acccaaggac accctcatga tctcacgcac ccccgaggtc        120
acatgcgtgg tggtggacgt gagccaggat gaccccgagg tgcagttcac atggtacata        180
aacaacgagc aggtgcgcac cgcccggccg ccgctacggg agcagcagtt caacagcacg        240
atccgcgtgg tcagcaccct ccccatcacg caccaggact ggctgagggg caaggagttc        300
aagtgcaaag tccacaacaa ggcactcccg gcccccatcg agaaaaccat ctccaaagcc        360
agagggcagc ccctggagcc gaaggtctac accatgggcc ctccccggga ggagctgagc        420
agcaggtcgg tcagcctgac ctgcatgatc aacggcttct acccttccga catctcggtg        480
gagtgggaga agaacgggaa ggcagaggac aactacaaga ccacgccggc cgtgctggac        540
agcgacggct cctacttcct ctacaacaag ctctcagtgc ccacgagtga gtggcagcgg        600
ggcgacgtct tcacctgctc cgtgatgcac gaggccttgc acaaccacta cacgcagaag        660
tccatctccc gctctccggg taaatga                                             687
```

<210> SEQ ID NO 11
<211> LENGTH: 229
<212> TYPE: PRT
<213> ORGANISM: Artificial Sequence
<220> FEATURE:
<223> OTHER INFORMATION: Mouse Fc fragment

<400> SEQUENCE: 11

```
Val Asp Val Pro Arg Asp Cys Gly Cys Lys Pro Cys Ile Cys Thr Val
1               5                   10                  15

Pro Glu Val Ser Ser Val Phe Ile Phe Pro Pro Lys Pro Lys Asp Val
            20                  25                  30

Leu Thr Ile Thr Leu Thr Pro Lys Val Thr Cys Val Val Val Asp Ile
        35                  40                  45

Ser Lys Asp Asp Pro Glu Val Gln Phe Ser Trp Phe Val Asp Asp Val
    50                  55                  60

Glu Val His Thr Ala Gln Thr Gln Pro Arg Glu Glu Gln Phe Asn Ser
65                  70                  75                  80

Thr Phe Arg Ser Val Ser Glu Leu Pro Ile Met His Gln Asp Trp Leu
                85                  90                  95

Asn Gly Lys Glu Phe Lys Cys Arg Val Asn Ser Ala Ala Phe Pro Ala
            100                 105                 110

Pro Ile Glu Lys Thr Ile Ser Lys Thr Lys Gly Arg Pro Lys Ala Pro
        115                 120                 125

Gln Val Tyr Thr Ile Pro Pro Lys Glu Gln Met Ala Lys Asp Lys
    130                 135                 140

Val Ser Leu Thr Cys Met Ile Thr Asp Phe Phe Pro Glu Asp Ile Thr
145                 150                 155                 160

Val Glu Trp Gln Trp Asn Gly Gln Pro Ala Glu Asn Tyr Lys Asn Thr
                165                 170                 175

Gln Pro Ile Met Asp Thr Asp Gly Ser Tyr Phe Val Tyr Ser Lys Leu
            180                 185                 190

Asn Val Gln Lys Ser Asn Trp Glu Ala Gly Asn Thr Phe Thr Cys Ser
        195                 200                 205

Val Leu His Glu Gly Leu His Asn His Thr Glu Lys Ser Leu Ser
    210                 215                 220

His Ser Pro Gly Lys
225
```

<210> SEQ ID NO 12
<211> LENGTH: 690
<212> TYPE: DNA
<213> ORGANISM: Artificial Sequence
<220> FEATURE:
<223> OTHER INFORMATION: sequence coding for the mouse Fc fragment

<400> SEQUENCE: 12

```
gtcgacgtgc ccaggattg tggttgtaag ccttgcatat gtacagtccc agaagtatca      60
tctgtcttca tcttccccc aaagcccaag gatgtgctca ccattactct gactcctaag     120
gtcacgtgtg ttgtggtaga catcagcaag gatgatcccg aggtccagtt cagctggttt    180
gtagatgatg tggaggtgca cacagctcag acgcaacccc gggaggagca gttcaacagc    240
actttccgct cagtcagtga acttcccatc atgcaccagg actggctcaa tggcaaggag    300
ttcaaatgca gggtcaacag tgcagctttc cctgccccca tcgagaaaac catctccaaa    360
accaaaggca gaccgaaggc tccacaggtg tacaccattc cacctcccaa ggagcagatg    420
gccaaggata aagtcagtct gacctgcatg ataacagact cttccctga agacattact     480
gtggagtggc agtggaatgg gcagccagcg gagaactaca agaacactca gcccatcatg    540
gacacagatg gctcttactt cgtctacagc aagctcaatg tgcagaagag caactgggag    600
gcaggaaata ctttcacctg ctctgtgtta catgagggcc tgcacaacca ccatactgag    660
aagagcctct cccactctcc tggtaaatga                                     690
```

<210> SEQ ID NO 13
<211> LENGTH: 469
<212> TYPE: PRT
<213> ORGANISM: Artificial Sequence
<220> FEATURE:
<223> OTHER INFORMATION: PERV-B.RBD ligand with mice FC fragment

<400> SEQUENCE: 13

```
Met His Pro Thr Leu Ser Trp Arg His Leu Pro Thr Arg Gly Gly Glu
1

-continued

```
Gly Lys Gln Glu Asn Ile Gln Lys Trp Ile Asn Gly Met Ser Trp Gly
        195                 200                 205

Ile Val Phe Tyr Lys Tyr Gly Gly Gly Ala Gly Ser Thr Leu Thr Ile
    210                 215                 220

Arg Leu Arg Ile Glu Ala Gly Thr Glu Pro Pro Val Ala Val Gly Ser
225                 230                 235                 240

Val Asp Val Pro Arg Asp Cys Gly Cys Lys Pro Cys Ile Cys Thr Val
                245                 250                 255

Pro Glu Val Ser Ser Val Phe Ile Phe Pro Pro Lys Pro Lys Asp Val
            260                 265                 270

Leu Thr Ile Thr Leu Thr Pro Lys Val Thr Cys Val Val Val Asp Ile
        275                 280                 285

Ser Lys Asp Asp Pro Glu Val Gln Phe Ser Trp Phe Val Asp Asp Val
    290                 295                 300

Glu Val His Thr Ala Gln Thr Gln Pro Arg Glu Glu Gln Phe Asn Ser
305                 310                 315                 320

Thr Phe Arg Ser Val Ser Glu Leu Pro Ile Met His Gln Asp Trp Leu
                325                 330                 335

Asn Gly Lys Glu Phe Lys Cys Arg Val Asn Ser Ala Ala Phe Pro Ala
            340                 345                 350

Pro Ile Glu Lys Thr Ile Ser Lys Thr Lys Gly Arg Pro Lys Ala Pro
        355                 360                 365

Gln Val Tyr Thr Ile Pro Pro Pro Lys Glu Gln Met Ala Lys Asp Lys
    370                 375                 380

Val Ser Leu Thr Cys Met Ile Thr Asp Phe Phe Pro Glu Asp Ile Thr
385                 390                 395                 400

Val Glu Trp Gln Trp Asn Gly Gln Pro Ala Glu Asn Tyr Lys Asn Thr
                405                 410                 415

Gln Pro Ile Met Asp Thr Asp Gly Ser Tyr Phe Val Tyr Ser Lys Leu
            420                 425                 430

Asn Val Gln Lys Ser Asn Trp Glu Ala Gly Asn Thr Phe Thr Cys Ser
        435                 440                 445

Val Leu His Glu Gly Leu His Asn His His Thr Glu Lys Ser Leu Ser
    450                 455                 460

His Ser Pro Gly Lys
465

<210> SEQ ID NO 14
<211> LENGTH: 1455
<212> TYPE: DNA
<213> ORGANISM: Artificial Sequence
<220> FEATURE:
<223> OTHER INFORMATION: coding sequence for the PERV-B.RBD ligand with
      a FC fragment

<400> SEQUENCE: 14
atgcatccca cgttaagctg gcgccacctc ccgactcggg gtggagagcc gaaaagactg      60
agaatcccct taagcttcgc ctccatcgcc tggttcctta ctctaacaat aactccccag     120
gccagtagta aacgccttat agacagctcg aacccccata gacctttatc ccttacctgg     180
ctgattattg accctgatac gggtgtcact gtaaatagca ctcgaggtgt tgctcctaga     240
ggcacctggt ggcctgaact gcatttctgc ctccgattga ttaaccccgc tgttaaaagc     300
acacctccca acctagtccg tagttatggg ttctattgct gcccaggcac agagaaagag     360
aaatactgtg gggttctgaa ggaatccttc tgtaggagat ggagctgcgt cacctccaac     420
```

```
gatggagact ggaaatggcc gatctctctc caggaccggg taaaattctc ctttgtcaat    480
tccggcccgg gcaagtacaa agtgatgaaa ctatataaag ataagagctg ctccccatca    540
gacttagatt atctaaagat aagtttcact gaaaaaggaa acaggaaaaa tattcaaaag    600
tggataaatg gtatgagctg ggaatagtt ttttataaat atggcggggg agcagggtcc     660
actttaacca ttcgccttag gatagaggcg gggacagaac ccctgtggc agtgggatcc     720 gtcgacgtgc ccagggattg tggttgtaag ccttgcatat gtacagtccc agaagtatca    780
tctgtcttca tcttcccccc aaagcccaag gatgtgctca ccattactct gactcctaag    840
gtcacgtgtg ttgtggtaga catcagcaag gatgatcccg aggtccagtt cagctggttt    900
gtagatgatg tggaggtgca cacagctcag acgcaacccc gggaggagca gttcaacagc    960
actttccgct cagtcagtga acttcccatc atgcaccagg actggctcaa tggcaaggag   1020
ttcaaatgca gggtcaacag tgcagctttc cctgccccca tcgagaaaac catctcccaaa  1080 accaaaggca gaccgaaggc tccacaggtg tacaccattc cacctcccaa ggagcagatg   1140
gccaaggata aagtcagtct gacctgcatg ataacagact tcttccctga agacattact   1200
gtggagtggc agtggaatgg gcagccagcg gagaactaca agaacactca gcccatcatg   1260
gacacagatg gctcttactt cgtctacagc aagctcaatg tgcagaagag caactgggag   1320
gcaggaaata ctttcacctg ctctgtgtta catgagggcc tgcacaacca ccatactgag   1380
aagagcctct cccactctcc tggtaaatga tcccagtgtc cttggagccc tctggtccta   1440
cagcggccgc tctag                                                    1455

<210> SEQ ID NO 15
<211> LENGTH: 19
<212> TYPE: RNA
<213> ORGANISM: Artificial Sequence
<220> FEATURE:
<223> OTHER INFORMATION: siRNA luciferase

<400> SEQUENCE: 15
cuuacgcuga guacuucga                                                  19

<210> SEQ ID NO 16
<211> LENGTH: 21
<212> TYPE: RNA
<213> ORGANISM: Artificial Sequence
<220> FEATURE:
<223> OTHER INFORMATION: siRNA SMVT

<400> SEQUENCE: 16
ggaugagucu ugguguguut t                                               21

<210> SEQ ID NO 17
<211> LENGTH: 548
<212> TYPE: PRT
<213> ORGANISM: Porcine endogenous retrovirus B
<220> FEATURE:
<223> OTHER INFORMATION: PERV-B Env protein

<400> SEQUENCE: 17

Met His Pro Thr Leu Ser Trp Arg His Leu Pro Thr Arg Gly Gly Glu
1               5                   10                  15

Pro Lys Arg Leu Arg Ile Pro Leu Ser Phe Ala Ser Ile Ala Trp Phe
            20                  25                  30

Leu Thr Leu Thr Ile Thr Pro Gln Ala Ser Ser Lys Arg Leu Ile Asp
        35                  40                  45
```

```
Ser Ser Asn Pro His Arg Pro Leu Ser Leu Thr Trp Leu Ile Ile Asp
    50                  55                  60

Pro Asp Thr Gly Val Thr Val Asn Ser Thr Arg Gly Val Ala Pro Arg
 65                  70                  75                  80

Gly Thr Trp Trp Pro Glu Leu His Phe Cys Leu Arg Leu Ile Asn Pro
                     85                  90                  95

Ala Val Lys Ser Thr Pro Pro Asn Leu Val Arg Ser Tyr Gly Phe Tyr
                100                 105                 110

Cys Cys Pro Gly Thr Glu Lys Glu Lys Tyr Cys Gly Gly Ser Gly Glu
            115                 120                 125

Ser Phe Cys Arg Arg Trp Ser Cys Val Thr Ser Asn Asp Gly Asp Trp
    130                 135                 140

Lys Trp Pro Ile Ser Leu Gln Asp Arg Val Lys Phe Ser Phe Val Asn
145                 150                 155                 160

Ser Gly Pro Gly Lys Tyr Lys Val Met Lys Leu Tyr Lys Asp Lys Ser
                165                 170                 175

Cys Ser Pro Ser Asp Leu Asp Tyr Leu Lys Ile Ser Phe Thr Glu Lys
            180                 185                 190

Gly Lys Gln Glu Asn Ile Gln Lys Trp Ile Asn Gly Met Ser Trp Gly
        195                 200                 205

Ile Val Phe Tyr Lys Tyr Gly Gly Ala Gly Ser Thr Leu Thr Ile
    210                 215                 220

Arg Leu Arg Ile Glu Thr Gly Thr Glu Pro Pro Val Ala Val Gly Pro
225                 230                 235                 240

Asp Lys Val Leu Ala Glu Gln Gly Pro Pro Ala Leu Glu Pro Pro His
                245                 250                 255

Asn Leu Pro Val Pro Gln Leu Thr Ser Leu Arg Pro Asp Ile Thr Gln
            260                 265                 270

Pro Pro Ser Asn Gly Thr Thr Gly Leu Ile Pro Thr Asn Thr Pro Arg
        275                 280                 285

Asn Ser Pro Gly Val Pro Val Lys Thr Gly Gln Arg Leu Phe Ser Leu
    290                 295                 300

Ile Gln Gly Ala Phe Gln Ala Ile Asn Ser Thr Asp Pro Asp Ala Thr
305                 310                 315                 320

Ser Ser Cys Trp Leu Cys Leu Ser Ser Gly Pro Pro Tyr Tyr Glu Gly
                325                 330                 335

Met Ala Lys Glu Gly Lys Phe Asn Val Thr Lys Glu His Arg Asn Gln
            340                 345                 350

Cys Thr Trp Gly Ser Arg Asn Lys Leu Thr Leu Thr Glu Val Ser Gly
        355                 360                 365

Lys Gly Thr Cys Ile Gly Lys Ala Pro Pro Ser His Gln His Leu Cys
    370                 375                 380

Tyr Ser Thr Val Val Tyr Glu Gln Ala Ser Glu Asn Gln Tyr Leu Val
385                 390                 395                 400

Pro Gly Tyr Asn Arg Trp Trp Ala Cys Asn Thr Gly Leu Thr Pro Cys
                405                 410                 415

Val Ser Thr Ser Val Phe Asn Gln Ser Lys Asp Phe Cys Val Met Val
            420                 425                 430

Gln Ile Val Pro Arg Val Tyr Tyr His Pro Glu Glu Val Leu Asp
        435                 440                 445

Glu Tyr Asp Tyr Arg Tyr Asn Arg Pro Lys Arg Glu Pro Val Ser Leu
    450                 455                 460

Thr Leu Ala Val Met Leu Gly Leu Gly Thr Ala Val Gly Val Gly Thr
```

```
                465                 470                 475                 480
Gly Thr Ala Ala Leu Ile Thr Gly Pro Gln Gln Leu Glu Lys Gly Leu
                    485                 490                 495

Gly Glu Leu His Ala Ala Met Thr Glu Asp Leu Arg Ala Leu Glu Glu
                500                 505                 510

Ser Val Ser Asn Leu Glu Glu Ser Leu Thr Ser Leu Ser Glu Val Val
                515                 520                 525

Leu Gln Asn Arg Arg Gly Leu Asp Leu Leu Phe Leu Arg Glu Gly Gly
            530                 535                 540

Leu Cys Ala Ala
545

<210> SEQ ID NO 18
<211> LENGTH: 459
<212> TYPE: PRT
<213> ORGANISM: Artificial Sequence
<220> FEATURE:
<223> OTHER INFORMATION: PERV-B SU protein

<400> SEQUENCE: 18

Met His Pro Thr Leu Ser Trp Arg His Leu Pro Thr Arg Gly Gly Glu
1               5                   10                  15

Pro Lys Arg Leu Arg Ile Pro Leu Ser Phe Ala Ser Ile Ala Trp Phe
                20                  25                  30

Leu Thr Leu Thr Ile Thr Pro Gln Ala Ser Ser Lys Arg Leu Ile Asp
            35                  40                  45

Ser Ser Asn Pro His Arg Pro Leu Ser Leu Thr Trp Leu Ile Ile Asp
50                  55                  60

Pro Asp Thr Gly Val Thr Val Asn Ser Thr Arg Gly Val Ala Pro Arg
65                  70                  75                  80

Gly Thr Trp Trp Pro Glu Leu His Phe Cys Leu Arg Leu Ile Asn Pro
                85                  90                  95

Ala Val Lys Ser Thr Pro Pro Asn Leu Val Arg Ser Tyr Gly Phe Tyr
                100                 105                 110

Cys Cys Pro Gly Thr Glu Lys Glu Lys Tyr Cys Gly Gly Ser Gly Glu
            115                 120                 125

Ser Phe Cys Arg Arg Trp Ser Cys Val Thr Ser Asn Asp Gly Asp Trp
        130                 135                 140

Lys Trp Pro Ile Ser Leu Gln Asp Arg Val Lys Phe Ser Phe Val Asn
145                 150                 155                 160

Ser Gly Pro Gly Lys Tyr Lys Val Met Lys Leu Tyr Lys Asp Lys Ser
                165                 170                 175

Cys Ser Pro Ser Asp Leu Asp Tyr Leu Lys Ile Ser Phe Thr Glu Lys
                180                 185                 190

Gly Lys Gln Glu Asn Ile Gln Lys Trp Ile Asn Gly Met Ser Trp Gly
            195                 200                 205

Ile Val Phe Tyr Lys Tyr Gly Gly Gly Ala Gly Ser Thr Leu Thr Ile
        210                 215                 220

Arg Leu Arg Ile Glu Thr Gly Thr Glu Pro Val Ala Val Gly Pro
225                 230                 235                 240

Asp Lys Val Leu Ala Glu Gln Gly Pro Pro Ala Leu Glu Pro Pro His
                245                 250                 255

Asn Leu Pro Val Pro Gln Leu Thr Ser Leu Arg Pro Asp Ile Thr Gln
                260                 265                 270

Pro Pro Ser Asn Gly Thr Thr Gly Leu Ile Pro Thr Asn Thr Pro Arg
```

```
                275                 280                 285
Asn Ser Pro Gly Val Pro Val Lys Thr Gly Gln Arg Leu Phe Ser Leu
    290                 295                 300
Ile Gln Gly Ala Phe Gln Ala Ile Asn Ser Thr Asp Pro Asp Ala Thr
305                 310                 315                 320
Ser Ser Cys Trp Leu Cys Leu Ser Ser Gly Pro Pro Tyr Tyr Glu Gly
                325                 330                 335
Met Ala Lys Glu Gly Lys Phe Asn Val Thr Lys Glu His Arg Asn Gln
            340                 345                 350
Cys Thr Trp Gly Ser Arg Asn Lys Leu Thr Leu Thr Glu Val Ser Gly
            355                 360                 365
Lys Gly Thr Cys Ile Gly Lys Ala Pro Pro Ser His Gln His Leu Cys
        370                 375                 380
Tyr Ser Thr Val Val Tyr Glu Gln Ala Ser Glu Asn Gln Tyr Leu Val
385                 390                 395                 400
Pro Gly Tyr Asn Arg Trp Trp Ala Cys Asn Thr Gly Leu Thr Pro Cys
                405                 410                 415
Val Ser Thr Ser Val Phe Asn Gln Ser Lys Asp Phe Cys Val Met Val
            420                 425                 430
Gln Ile Val Pro Arg Val Tyr Tyr His Pro Glu Val Val Leu Asp
        435                 440                 445
Glu Tyr Asp Tyr Arg Tyr Asn Arg Pro Lys Arg
    450                 455
```

<210> SEQ ID NO 19
<211> LENGTH: 238
<212> TYPE: PRT
<213> ORGANISM: Artificial Sequence
<220> FEATURE:
<223> OTHER INFORMATION: PERV-B.RBD ligand

<400> SEQUENCE: 19

```
Met His Pro Thr Leu Ser Trp Arg His Leu Pro Thr Arg Gly Gly Glu
1               5                   10                  15
Pro Lys Arg Leu Arg Ile Pro Leu Ser Phe Ala Ser Ile Ala Trp Phe
            20                  25                  30
Leu Thr Leu Thr Ile Thr Pro Gln Ala Ser Ser Lys Arg Leu Ile Asp
        35                  40                  45
Ser Ser Asn Pro His Arg Pro Leu Ser Leu Thr Trp Leu Ile Ile Asp
    50                  55                  60
Pro Asp Thr Gly Val Thr Val Asn Ser Thr Arg Gly Val Ala Pro Arg
65                  70                  75                  80
Gly Thr Trp Trp Pro Glu Leu His Phe Cys Leu Arg Leu Ile Asn Pro
                85                  90                  95
Ala Val Lys Ser Thr Pro Pro Asn Leu Val Arg Ser Tyr Gly Phe Tyr
            100                 105                 110
Cys Cys Pro Gly Thr Glu Lys Glu Lys Tyr Cys Gly Gly Ser Gly Glu
        115                 120                 125
Ser Phe Cys Arg Arg Trp Ser Cys Val Thr Ser Asn Asp Gly Asp Trp
    130                 135                 140
Lys Trp Pro Ile Ser Leu Gln Asp Arg Val Lys Phe Ser Phe Val Asn
145                 150                 155                 160
Ser Gly Pro Gly Lys Tyr Lys Val Met Lys Leu Tyr Lys Asp Lys Ser
                165                 170                 175
Cys Ser Pro Ser Asp Leu Asp Tyr Leu Lys Ile Ser Phe Thr Glu Lys
```

```
                180             185              190
Gly Lys Gln Glu Asn Ile Gln Lys Trp Ile Asn Gly Met Ser Trp Gly
            195                 200             205

Ile Val Phe Tyr Lys Tyr Gly Gly Ala Gly Ser Thr Leu Thr Ile
        210                 215             220

Arg Leu Arg Ile Glu Thr Gly Thr Glu Pro Pro Val Ala Val
225                 230             235

<210> SEQ ID NO 20
<211> LENGTH: 195
<212> TYPE: PRT
<213> ORGANISM: Artificial Sequence
<220> FEATURE:
<223> OTHER INFORMATION: PERV-B-RBD ligand without signal peptide

<400> SEQUENCE: 20

Lys Arg Leu Ile Asp Ser Ser Asn Pro His Arg Pro Leu Ser Leu Thr
1               5                   10                  15

Trp Leu Ile Ile Asp Pro Asp Thr Gly Val Thr Val Asn Ser Thr Arg
            20                  25                  30

Gly Val Ala Pro Arg Gly Thr Trp Trp Pro Glu Leu His Phe Cys Leu
        35                  40                  45

Arg Leu Ile Asn Pro Ala Val Lys Ser Thr Pro Pro Asn Leu Val Arg
    50                  55                  60

Ser Tyr Gly Phe Tyr Cys Cys Pro Gly Thr Glu Lys Glu Lys Tyr Cys
65                  70                  75                  80

Gly Gly Ser Gly Glu Ser Phe Cys Arg Arg Trp Ser Cys Val Thr Ser
                85                  90                  95

Asn Asp Gly Asp Trp Lys Trp Pro Ile Ser Leu Gln Asp Arg Val Lys
            100                 105                 110

Phe Ser Phe Val Asn Ser Gly Pro Gly Lys Tyr Lys Val Met Lys Leu
        115                 120                 125

Tyr Lys Asp Lys Ser Cys Ser Pro Ser Asp Leu Asp Tyr Leu Lys Ile
    130                 135                 140

Ser Phe Thr Glu Lys Gly Lys Gln Glu Asn Ile Gln Lys Trp Ile Asn
145                 150                 155                 160

Gly Met Ser Trp Gly Ile Val Phe Tyr Lys Tyr Gly Gly Thr Gly
                165                 170                 175

Ser Thr Leu Thr Ile Arg Leu Arg Ile Glu Thr Gly Thr Glu Pro Pro
            180                 185                 190

Val Ala Val
        195

<210> SEQ ID NO 21
<211> LENGTH: 238
<212> TYPE: PRT
<213> ORGANISM: Artificial Sequence
<220> FEATURE:
<223> OTHER INFORMATION: PERV-B RBD ligand

<400> SEQUENCE: 21

Met His Pro Thr Leu Ser Trp Arg His Leu Pro Thr Arg Gly Gly Glu
1               5                   10                  15

Pro Lys Arg Leu Arg Ile Pro Leu Ser Phe Ala Ser Ile Ala Trp Phe
            20                  25                  30

Leu Thr Leu Thr Ile Thr Pro Gln Ala Ser Ser Lys Arg Leu Ile Asp
        35                  40                  45
```

Ser Ser Asn Pro His Arg Pro Leu Ser Leu Thr Trp Leu Ile Ile Asp
    50                  55                  60

Pro Asp Thr Gly Val Thr Val Asn Ser Thr Arg Gly Val Ala Pro Arg
65                  70                  75                  80

Gly Thr Trp Trp Pro Glu Leu His Phe Cys Leu Arg Leu Ile Asn Pro
                85                  90                  95

Ala Val Lys Ser Thr Pro Pro Asn Leu Val Arg Ser Tyr Gly Phe Tyr
            100                 105                 110

Cys Cys Pro Gly Thr Glu Lys Glu Lys Tyr Cys Gly Gly Ser Glu Glu
                115                 120                 125

Ser Phe Cys Arg Arg Trp Ser Cys Val Thr Ser Asn Asp Gly Asp Trp
    130                 135                 140

Lys Trp Pro Ile Ser Leu Gln Asp Arg Val Lys Phe Ser Phe Val Asn
145                 150                 155                 160

Ser Gly Pro Gly Lys Tyr Lys Val Met Lys Leu Tyr Lys Asp Lys Ser
                165                 170                 175

Cys Ser Pro Ser Asp Leu Asp Tyr Leu Lys Ile Ser Phe Thr Glu Lys
            180                 185                 190

Gly Lys Gln Glu Asn Ile Gln Lys Trp Ile Asn Gly Met Ser Trp Gly
                195                 200                 205

Ile Val Phe Tyr Lys Tyr Gly Gly Ala Gly Ser Thr Leu Thr Ile
    210                 215                 220

Arg Leu Arg Ile Glu Thr Gly Thr Glu Pro Pro Val Ala Val
225                 230                 235

<210> SEQ ID NO 22
<211> LENGTH: 195
<212> TYPE: PRT
<213> ORGANISM: Artificial Sequence
<220> FEATURE:
<223> OTHER INFORMATION: PERV-B.RBD without signal peptide

<400> SEQUENCE: 22

Lys Arg Leu Ile Asp Ser Ser Asn Pro His Arg Pro Le

-continued

```
Ser Thr Leu Thr Ile Arg Leu Arg Ile Glu Thr Gly Thr Glu Pro Pro
            180                 185                 190

Val Ala Val
        195

<210> SEQ ID NO 23
<211> LENGTH: 21
<212> TYPE: RNA
<213> ORGANISM: Artificial Sequence
<220> FEATURE:
<223> OTHER INFORMATION: siRNA SMVT-A

<400> SEQUENCE: 23
gcaggaucau gccagaaaut t                                              21

<210> SEQ ID NO 24
<211> LENGTH: 635
<212> TYPE: PRT
<213> ORGANISM: Homo sapiens
<220> FEATURE:
<223> OTHER INFORMATION: SMVT variant 2

<400> SEQUENCE: 24

Met Ser Val Gly Val Ser Thr Ser Ala Pro Leu Ser Pro Thr Ser Gly
1               5                   10                  15

Thr Ser Val Gly Met Ser Thr Phe Ser Ile Met Asp Tyr Val Val Phe
            20                  25                  30

Val Leu Leu Leu Val Leu Ser Leu Ala Ile Gly Leu Tyr His Ala Cys
        35                  40                  45

Arg Gly Trp Gly Arg His Thr Val Gly Glu Leu Met Ala Asp Arg
    50                  55                  60

Lys Met Gly Cys Leu Pro Val Ala Leu Ser Leu Leu Ala Thr Phe Gln
65                  70                  75                  80

Ser Ala Val Ala Ile Leu Gly Val Pro Ser Glu Ile Tyr Arg Phe Gly
                85                  90                  95

Thr Gln Tyr Trp Phe Leu Gly Cys Cys Tyr Phe Leu Gly Leu Leu Ile
            100                 105                 110

Pro Ala His Ile Phe Ile Pro Val Phe Tyr Arg Leu His Leu Thr Ser
        115                 120                 125

Ala Tyr Glu Tyr Leu Glu Leu Arg Phe Asn Lys Thr Val Arg Val Cys
    130                 135                 140

Gly Thr Val Thr Phe Ile Phe Gln Met Val Ile Tyr Met Gly Val Val
145                 150                 155                 160

Leu Tyr Ala Pro Ser Leu Ala Leu Asn Ala Val Thr Gly Leu Asp Leu
                165                 170                 175

Trp Leu Ser Val Leu Ala Leu Gly Ile Val Cys Thr Val Tyr Thr Ala
            180                 185                 190

Leu Gly Gly Leu Lys Ala Val Ile Trp Thr Asp Val Phe Gln Thr Leu
        195                 200                 205

Val Met Phe Leu Gly Gln Leu Ala Val Ile Ile Val Gly Ser Ala Lys
    210                 215                 220

Val Gly Gly Leu Gly Arg Val Trp Ala Val Ala Ser Gln His Gly Arg
225                 230                 235                 240

Ile Ser Gly Phe Glu Leu Asp Pro Asp Pro Phe Val Arg His Thr Phe
                245                 250                 255

Trp Thr Leu Ala Phe Gly Gly Val Phe Met Met Leu Ser Leu Tyr Gly
            260                 265                 270
```

```
Val Asn Gln Ala Gln Val Gln Arg Tyr Leu Ser Ser Arg Thr Glu Lys
            275                 280                 285

Ala Ala Val Leu Ser Cys Tyr Ala Val Phe Pro Phe Gln Gln Val Ser
290                 295                 300

Leu Cys Val Gly Cys Leu Ile Gly Leu Val Met Phe Ala Tyr Tyr Gln
305                 310                 315                 320

Glu Tyr Pro Met Ser Ile Gln Ala Gln Ala Ala Pro Asp Gln Phe
                325                 330                 335

Val Leu Tyr Phe Val Met Asp Leu Leu Lys Gly Leu Pro Gly Leu Pro
            340                 345                 350

Gly Leu Phe Ile Ala Cys Leu Phe Ser Gly Ser Leu Ser Thr Ile Ser
            355                 360                 365

Ser Ala Phe Asn Ser Leu Ala Thr Val Thr Met Glu Asp Leu Ile Arg
370                 375                 380

Pro Trp Phe Pro Glu Phe Ser Glu Ala Arg Ala Ile Met Leu Ser Arg
385                 390                 395                 400

Gly Leu Ala Phe Gly Tyr Gly Leu Leu Cys Leu Gly Met Ala Tyr Ile
                405                 410                 415

Ser Ser Gln Met Gly Pro Val Leu Gln Ala Ala Ile Ser Ile Phe Gly
                420                 425                 430

Met Val Gly Gly Pro Leu Leu Gly Leu Phe Cys Leu Gly Met Phe Phe
            435                 440                 445

Pro Cys Ala Asn Pro Pro Gly Ala Val Val Gly Leu Leu Ala Gly Leu
            450                 455                 460

Val Met Ala Phe Trp Ile Gly Ile Gly Ser Ile Val Thr Ser Met Gly
465                 470                 475                 480

Phe Ser Met Pro Pro Ser Pro Ser Asn Gly Ser Ser Phe Ser Leu Pro
                485                 490                 495

Thr Asn Leu Thr Val Ala Thr Val Thr Thr Leu Met Pro Leu Thr Thr
                500                 505                 510

Phe Ser Lys Pro Thr Gly Leu Gln Arg Phe Tyr Ser Leu Ser Tyr Leu
            515                 520                 525

Trp Tyr Ser Ala His Asn Ser Thr Thr Val Ile Val Val Gly Leu Ile
530                 535                 540

Val Ser Leu Leu Thr Gly Arg Met Arg Gly Arg Ser Leu Asn Pro Ala
545                 550                 555                 560

Thr Ile Tyr Pro Val Leu Pro Lys Leu Leu Ser Leu Leu Pro Leu Ser
                565                 570                 575

Cys Gln Lys Arg Leu His Cys Arg Ser Tyr Gly Gln Asp His Leu Asp
            580                 585                 590

Thr Gly Leu Phe Pro Glu Lys Pro Arg Asn Gly Val Leu Gly Asp Ser
            595                 600                 605

Arg Asp Lys Glu Ala Met Ala Leu Asp Gly Thr Ala Tyr Gln Gly Ser
610                 615                 620

Ser Ser Thr Cys Ile Leu Gln Glu Thr Ser Leu
625                 630                 635

<210> SEQ ID NO 25
<211> LENGTH: 548
<212> TYPE: PRT
<213> ORGANISM: Artificial Sequence
<220> FEATURE:
<223> OTHER INFORMATION: PERV-B Env

<400> SEQUENCE: 25
```

-continued

```
Met His Pro Thr Leu Ser Trp Arg His Leu Pro Thr Arg Gly Gly Glu
1               5                   10                  15

Pro Lys Arg Leu Arg Ile Pro Leu Ser Phe Ala Ser Ile Ala Trp Phe
            20                  25                  30

Leu Thr Leu Thr Ile Thr Pro Gln Ala Ser Ser Lys Arg Leu Ile Asp
        35                  40                  45

Ser Ser Asn Pro His Arg Pro Leu Ser Leu Thr Trp Leu Ile Ile Asp
    50                  55                  60

Pro Asp Thr Gly Val Thr Val Asn Ser Thr Arg Gly Val Ala Pro Arg
65                  70                  75                  80

Gly Thr Trp Trp Pro Glu Leu His Phe Cys Leu Arg Leu Ile Asn Pro
                85                  90                  95

Ala Val Lys Ser Thr Pro Pro Asn Leu Val Arg Ser Tyr Gly Phe Tyr
                100                 105                 110

Cys Cys Pro Gly Thr Glu Lys Glu Lys Tyr Cys Gly Ser Glu Glu
            115                 120                 125

Ser Phe Cys Arg Arg Trp Ser Cys Val Thr Ser Asn Asp Gly Asp Trp
    130                 135                 140

Lys Trp Pro Ile Ser Leu Gln Asp Arg Val Lys Phe Ser Phe Val Asn
145                 150                 155                 160

Ser Gly Pro Gly Lys Tyr Lys Val Met Lys Leu Tyr Lys Asp Lys Ser
                165                 170                 175

Cys Ser Pro Ser Asp Leu Asp Tyr Leu Lys Ile Ser Phe Thr Glu Lys
            180                 185                 190

Gly Lys Gln Glu Asn Ile Gln Lys Trp Ile Asn Gly Met Ser Trp Gly
            195                 200                 205

Ile Val Phe Tyr Lys Tyr Gly Gly Ala Gly Ser Thr Leu Thr Ile
    210                 215                 220

Arg Leu Arg Ile Glu Thr Gly Thr Glu Pro Val Ala Val Gly Pro
225                 230                 235                 240

Asp Lys Val Leu Ala Glu Gln Gly Pro Ala Leu Glu Pro Pro His
                245                 250                 255

Asn Leu Pro Val Pro Gln Leu Thr Ser Leu Arg Pro Asp Ile Thr Gln
            260                 265                 270

Pro Pro Ser Asn Gly Thr Thr Gly Leu Ile Pro Thr Asn Thr Pro Arg
        275                 280                 285

Asn Ser Pro Gly Val Pro Val Lys Thr Gly Gln Arg Leu Phe Ser Leu
    290                 295                 300

Ile Gln Gly Ala Phe Gln Ala Ile Asn Ser Thr Asp Pro Asp Ala Thr
305                 310                 315                 320

Ser Ser Cys Trp Leu Cys Leu Ser Ser Gly Pro Pro Tyr Tyr Glu Gly
                325                 330                 335

Met Ala Lys Glu Gly Lys Phe Asn Val Thr Lys Glu His Arg Asn Gln
            340                 345                 350

Cys Thr Trp Gly Ser Arg Asn Lys Leu Thr Leu Thr Glu Val Ser Gly
        355                 360                 365

Lys Gly Thr Cys Ile Gly Lys Ala Pro Pro Ser His Gln His Leu Cys
    370                 375                 380

Tyr Ser Thr Val Val Tyr Glu Gln Ala Ser Glu Asn Gln Tyr Leu Val
385                 390                 395                 400

Pro Gly Tyr Asn Arg Trp Trp Ala Cys Asn Thr Gly Leu Thr Pro Cys
                405                 410                 415

Val Ser Ser Ser Val Phe Asn Gln Ser Lys Asp Phe Cys Val Met Val
```

```
                    420                 425                 430
Gln Ile Val Pro Arg Val Tyr Tyr His Pro Glu Glu Val Leu Asp
            435                 440                 445
Glu Tyr Asp Tyr Arg Tyr Asn Arg Pro Lys Arg Glu Pro Val Ser Leu
        450                 455                 460
Thr Leu Ala Val Met Leu Gly Leu Gly Thr Ala Val Gly Val Gly Thr
465                 470                 475                 480
Gly Thr Ala Ala Leu Ile Thr Gly Pro Gln Gln Leu Glu Lys Gly Leu
                485                 490                 495
Gly Glu Leu His Ala Ala Met Thr Glu Asp Leu Arg Ala Leu Glu Glu
            500                 505                 510
Ser Val Ser Asn Leu Glu Glu Ser Leu Thr Ser Leu Ser Glu Val Val
        515                 520                 525
Leu Gln Asn Arg Arg Gly Leu Asp Leu Leu Phe Leu Arg Glu Gly Gly
        530                 535                 540
Leu Cys Ala Ala
545

<210> SEQ ID NO 26
<211> LENGTH: 459
<212> TYPE: PRT
<213> ORGANISM: Artificial Sequence
<220> FEATURE:
<223> OTHER INFORMATION: PERVB Env SU domain

<400> SEQUENCE: 26

Met His Pro Thr Leu Ser Trp Arg His Leu Pro Thr Arg Gly Gly Glu
1               5                   10                  15
Pro Lys Arg Leu Arg Ile Pro Leu Ser Phe Ala Ser Ile Ala Trp Phe
            20                  25                  30
Leu Thr Leu Thr Ile Thr Pro Gln Ala Ser Ser Lys Arg Leu Ile Asp
        35                  40                  45
Ser Ser Asn Pro His Arg Pro Leu Ser Leu Thr Trp Leu Ile Ile Asp
    50                  55                  60
Pro Asp Thr Gly Val Thr Val Asn Ser Thr Arg Gly Val Ala Pro Arg
65                  70                  75                  80
Gly Thr Trp Trp Pro Glu Leu His Phe Cys Leu Arg Leu Ile Asn Pro
                85                  90                  95
Ala Val Lys Ser Thr Pro Pro Asn Leu Val Arg Ser Tyr Gly Phe Tyr
            100                 105                 110
Cys Cys Pro Gly Thr Glu Lys Glu Lys Tyr Cys Gly Gly Ser Glu Glu
        115                 120                 125
Ser Phe Cys Arg Arg Trp Ser Cys Val Thr Ser Asn Asp Gly Asp Trp
    130                 135                 140
Lys Trp Pro Ile Ser Leu Gln Asp Arg Val Lys Phe Ser Phe Val Asn
145                 150                 155                 160
Ser Gly Pro Gly Lys Tyr Lys Val Met Lys Leu Tyr Lys Asp Lys Ser
                165                 170                 175
Cys Ser Pro Ser Asp Leu Asp Tyr Leu Lys Ile Ser Phe Thr Glu Lys
            180                 185                 190
Gly Lys Gln Glu Asn Ile Gln Lys Trp Ile Asn Gly Met Ser Trp Gly
        195                 200                 205
Ile Val Phe Tyr Lys Tyr Gly Gly Gly Ala Gly Ser Thr Leu Thr Ile
    210                 215                 220
Arg Leu Arg Ile Glu Thr Gly Thr Glu Pro Pro Val Ala Val Gly Pro
```

-continued

```
225                 230                 235                 240

Asp Lys Val Leu Ala Glu Gln Gly Pro Pro Ala Leu Glu Pro Pro His
                245                 250                 255

Asn Leu Pro Val Pro Gln Leu Thr Ser Leu Arg Pro Asp Ile Thr Gln
            260                 265                 270

Pro Pro Ser Asn Gly Thr Thr Gly Leu Ile Pro Thr Asn Thr Pro Arg
        275                 280                 285

Asn Ser Pro Gly Val Pro Val Lys Thr Gly Gln Arg Leu Phe Ser Leu
    290                 295                 300

Ile Gln Gly Ala Phe Gln Ala Ile Asn Ser Thr Asp Pro Asp Ala Thr
305                 310                 315                 320

Ser Ser Cys Trp Leu Cys Leu Ser Ser Gly Pro Pro Tyr Tyr Glu Gly
                325                 330                 335

Met Ala Lys Glu Gly Lys Phe Asn Val Thr Lys Glu His Arg Asn Gln
            340                 345                 350

Cys Thr Trp Gly Ser Arg Asn Lys Leu Thr Leu Thr Glu Val Ser Gly
        355                 360                 365

Lys Gly Thr Cys Ile Gly Lys Ala Pro Pro Ser His Gln His Leu Cys
    370                 375                 380

Tyr Ser Thr Val Val Tyr Glu Gln Ala Ser Glu Asn Gln Tyr Leu Val
385                 390                 395                 400

Pro Gly Tyr Asn Arg Trp Trp Ala Cys Asn Thr Gly Leu Thr Pro Cys
                405                 410                 415

Val Ser Ser Ser Val Phe Asn Gln Ser Lys Asp Phe Cys Val Met Val
            420                 425                 430

Gln Ile Val Pro Arg Val Tyr Tyr His Pro Glu Glu Val Val Leu Asp
        435                 440                 445

Glu Tyr Asp Tyr Arg Tyr Asn Arg Pro Lys Arg
    450                 455

<210> SEQ ID NO 27
<211> LENGTH: 714
<212> TYPE: DNA
<213> ORGANISM: Artificial Sequence
<220> FEATURE:
<223> OTHER INFORMATION: coding sequence for the PERV-B.RBD ligand

<400> SEQUENCE: 27
atgcatccca cgttaagctg gcgccacctc ccgactcggg gtggagagcc gaaaagactg      60
agaatcccct taagcttcgc ctccatcgcc tggttcctta ctctaacaat aactccccag     120
gccagtagta aacgccttat agacagctcg aacccccata gacctttatc ccttacctgg     180
ctgattattg accctgatac gggtgtcact gtaaatagca ctcgaggtgt tgctcctaga     240
ggcacctggt ggcctgaact gcatttctgc ctccgattga ttaaccccgc tgttaaaagc     300
acacctccca acctagtccg tagttatggg ttctattgct gcccaggcac agagaaagag     360
aaatactgtg ggggttctga ggaatccttc tgtaggagat ggagctgcgt cacctccaac     420
gatggagact ggaaatggcc gatctctctc caggaccggg taaaattctc ctttgtcaat     480
tccggcccgg gcaagtacaa agtgatgaaa ctatataaag ataagagctg ctccccatca     540
gacttagatt atctaaagat aagtttcact gaaaaaggaa aacaggaaaa tattcaaaag     600
tggataaatg gtatgagctg ggaatagttt ttttataaat atggcggggg agcagggtcc     660
actttaacca ttcgccttag gatagagacg gggacagaac cccctgtggc agtg           714
```

USE OF LIGANDS DERIVED FROM RECEPTOR-BINDING DOMAIN OF PORCINE ENDOGENOUS RETROVIRUS TYPE B FOR DIAGNOSING SMVT-RELATED DISEASES

FIELD

The present invention relates to the diagnosis of diseases related to the sodium-dependent multivitamin transporter/solute carrier family 5 member 6 (SMVT/SLC5A6). In particular, the present invention relates to methods for measuring the level of SMVT in a biological sample using a receptor binding domain (RBD) ligand related to the envelope protein of porcine endogenous retrovirus type B (PERV-B).

BACKGROUND

The sodium-dependent multivitamin transporter (SMVT), the product of the solute carrier family 5 member 6 (SLC5A6) gene, is a 12-pass transmembrane protein responsible for the cellular uptake of biotin, pantothenic acid and lipoic acid (Wang et al., J Biol Chem. 1999 May 21; 274(21):14875-83; Prasad et al., J Biol Chem. 1998 Mar. 27; 273(13):7501-6). As such, it plays an essential role in the synthesis and metabolism of proteins, carbohydrates and lipids. Biotin deficiency leads to a variety of clinical abnormalities, including for instance growth retardation, neurological disorders and dermatological disorders (Subramanian et al., Hum Genet. 2017 February; 136(2):253-261) and animal studies have shown that biotin deficiencies during pregnancy lead to embryonic growth retardation, congenital malformation and death (Watanabe et al., Nutrition. 2009 January; 25(1):78-84; Quick and Shi, Vitam Horm. 2015; 98:63-100). Additionally, the inhibition of biotin uptake and a reduced activity of the SLC5A6 promoter in intestinal cells upon *Salmonella* infection has been reported (Ghosal et al., Am J Physiol Gastrointest Liver Physiol. 2015 Jul. 15; 309(2):G123-31). Furthermore, SMVT expression is altered in several cancer cell lines suggesting its implication in cancer, in particular liver cancer, prostate cancer, lung cancer, gallbladder cancer, pancreas cancer, colon cancer, ovarian cancer, brain cancer, kidney cancer and lymphomas (see the Examples). Furthermore, SMVT gene expression has also been found altered in colon cancer (Provenzani et al., Carcinogenesis. 2006 July: 27(7):1323-33), Vincristine-sensitive and resistant ovarian carcinoma cell lines (Buys et al., Genes Chromosomes Cancer. 2007 December; 46(12): 1069-79), prostate cancer (Sissung et al., Pharmacogenomics. 2016 Dec.; 17(18):1979-1986), lung adenocarcinoma (Leithner et al., PLoS One. 2016 Jun. 13; 11(6):e0157453) and anaplastic thyroid carcinomas (Pita et al., J Clin Endocrinol Metab. 2014 March; 99(3):E497-507). SMVT has also been considered as a potential target for drug delivery (Vadlapudi et al., Curr Drug Targets. 2012 June; 13(7):994-1003). Hence, beyond its interest in the determination of the metabolic state of a given cell, there is a need for a specific ligand targeting SMVT for its use in the diagnosis of SMVT-related diseases and drug targeting.

Here, the inventors demonstrated that a ligand related to the porcine endogenous retrovirus type B (PERV-B, that may also be referred to as porcine endogenous retrovirus subgroup B) envelope protein can bind specifically to SMVT. Several retrovirus envelope glycoproteins (Env) use nutrient transporters from the solute carrier family as receptors. The SLC-Env binding is mediated by the receptor binding domain (RBD) of the Env protein. Such interactions could in principle be used to develop ligands usable for the detection and quantification of a nutrient transporter. Yet, the limited knowledge on the potential targets at the human cell surface recognized by the various RBDs has limited until now the development of probes based on this interaction.

The present invention thus relates to the use of ligands derived from the envelope protein, in particular the RDB domain in said protein, of the porcine endogenous retrovirus of type B (PERV-B.RBD ligands) for the detection and quantification of SMVT on the cell surface, and in particular for diagnostic purposes.

SUMMARY

The present invention relates to an in vitro method for detecting and/or measuring the level of sodium-dependent multivitamin transporter (SMVT) in a biological sample, wherein said method comprises the steps of:
a. contacting said biological sample with a PERV-B.RBD ligand, a variant and/or a fragment thereof; and,
b. detecting and/or measuring the binding of said PERV-B.RBD ligand, variant and/or fragment thereof to SMVT.

In one embodiment, the method of the invention further comprises comparing the binding level measured at step b. with a reference value.

In one embodiment, the amino acid sequence of said PERV-B.RBD ligand, variant and/or fragment thereof comprises or consists of an amino acid sequence selected from the group comprising or consisting of the amino acid sequences SEQ ID NO: 2, SEQ ID, NO: 4, SEQ ID NO: 5, SEQ ID NO:6, SEQ ID NO: 17, SEQ ID NO: 18, SEQ ID NO: 19, SEQ ID NO: 20, SEQ ID NO: 21 and SEQ ID NO: 22 and variants and/or fragments thereof.

In one embodiment, the amino acid sequence of said PERV-B.RBD ligand, variant and/or fragment thereof comprises or consists of an amino acid sequence selected from the group comprising or consisting of the amino acid sequences SEQ ID NO: 2, SEQ ID, NO: 4, SEQ ID NO: 5, SEQ ID NO:6, SEQ ID NO: 17, SEQ ID NO: 18, SEQ ID NO: 19, SEQ ID NO: 20, SEQ ID NO: 21, SEQ ID NO: 22, SEQ ID NO: 25 and SEQ ID NO: 26 and variants and/or fragments thereof.

In one embodiment, the amino acid sequence of said PERV-B.RBD ligand, variant and/or fragment thereof comprises or consists of an amino acid sequence selected from the group comprising or consisting of the amino acid sequences SEQ ID NO: 5, SEQ ID NO:6, SEQ ID NO: 19, SEQ ID NO: 20, SEQ ID NO: 21 and SEQ ID NO: 22 and variants and/or fragments thereof.

In one embodiment, said PERV-B.RBD ligand, variant and/or fragment thereof is labeled with a detectable label.

In one embodiment, said method is for diagnosing a SMVT-related disease in a subject or for identifying a subject as being at risk of developing a SMVT-related disease.

In one embodiment, said SMVT-related disease is cancer, preferably selected from the group comprising liver cancer, prostate cancer, lung, cancer, gallbladder cancer, pancreas cancer, colon cancer, ovarian cancer, brain cancer, kidney cancer, thyroid cancer and lymphomas.

In one embodiment, said SMVT-related disease is a neurodegenerative disease, preferably multiple sclerosis or Huntington's disease.

In one embodiment, said SMVT-related disease is a neuroinflammatory disease, preferably multiple sclerosis.

In one embodiment, said SMVT-related disease is a disorder of pregnancy, preferably pre-eclampsia or intrauterine growth retardation.

In one embodiment, said SMVT-related disease is an infectious disease, preferably an infectious disease caused by a bacterium, more preferably an infectious disease caused by a bacterium belonging to the order Enterobacteriales.

The present invention further relates to a PERV-B.RBD ligand, a variant and/or a fragment thereof for use in an in vivo diagnosis method of a SMVT-related disease in a subject.

In one embodiment, said SMVT-related disease is a cancer, a neuroinflammatory or neurodegenerative disease, an infectious disease, a disorder of pregnancy or a disorder related to a mutation in the SLC5A6 gene. In one embodiment, said SMVT-related disease is a cancer, a neuroinflammatory disease, an infectious disease or a disorder of pregnancy. In one embodiment, said SMVT-related disease is a disorder related to a mutation in the SLC5A6 gene. In one embodiment, the SMVT-related disease is cancer, a disorder of pregnancy, an infectious disease or a neurodegenerative disease.

In one embodiment, said cancer is selected from the group comprising or consisting of liver cancer, prostate cancer, lung cancer, gallbladder cancer, pancreas cancer, colon cancer, ovarian cancer, brain cancer, kidney cancer, thyroid cancer, lymphomas, urothelial cancer, cervical cancer and endometrial cancer In one embodiment, said in vivo diagnosis method is based on medical imaging.

The present invention further relates to a PERV-B.RBD ligand coupled to a detectable label, preferably wherein said detectable label is a Fc fragment.

The present invention further relates to the use of the labeled PERV-B.RBD as described herein as a probe for medical imagery.

In the present invention, the following terms have the following meanings:

The term "about" preceding a figure means plus or less 10% of the value of said figure. It is to be understood that the figure to which the term "about" refers is itself also specifically, and preferably, disclosed.

The term "amino acid" as used herein, refers to both natural and synthetic amino acids, and both D and L amino acids. They are represented by their full name, their three letter code or their one letter code as well known in the art Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P;

Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. "Standard amino acid" or "naturally occurring amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. For example, naphtlylalanine can be substituted for tryptophan to facilitate synthesis. Other synthetic amino acids that can be substituted include, but are not limited to, L-hydroxypropyl, L-3,4-dihydroxyphenylalanyl, alpha-amino acids such as L-alpha-hydroxylysyl and D-alpha-methylalanyl, L-alpha-methylalanyl, beta-amino acids, and isoquinolyl. The term "amino acid" also encompasses chemically modified amino acids, including, but not limited to, salts, amino acid derivatives (such as amides), and substitutions Amino acids contained within the polypeptides of the present invention, and particularly at the carboxy- or amino-terminus, can be modified by methylation, amidation, acetylation or substitution with other chemical groups which can change the polypeptide's circulating half-life without adversely affecting their activity. Additionally, a disulfide linkage may be present or absent in the polypeptides of the invention. The RBD ligands of the invention may comprise standard amino acids or non-standard amino acids. Polypeptide mimetics include polypeptides having the following modifications: i) polypeptides wherein one or more of the peptidyl—C(O)NR— linkages (bonds) have been replaced by a non-peptidyl linkage such as a —CH$_2$-carbamate linkage (—CH$_2$OC(O)NR—), a phosphonate linkage, a —CH$_2$-sulfonamide (—CH$_2$—S(O)$_2$NR—) linkage, a urea (—NHC(O)NH—) linkage, a —CH$_2$-secondary amine linkage, or with an alkylated peptidyl linkage (—C(O)NR—) wherein R is C$_1$-C$_4$ alkyl; ii) polypeptides wherein the N-terminus is derivatized to a —NRR$^1$ group, to a —NRC(O)R group, to a —NRC(O)OR group, to a —NRS(O)$_2$R group, to a —NHC(O)NHR group where R and R$^1$ are hydrogen or C$_1$-C$_4$ alkyl with the proviso that R and R$^1$ are not both hydrogen; iii) polypeptides wherein the C terminus is derivatized to —C(O)R$^2$ where R$^2$ is selected from the group consisting of C$_1$-C$_4$ alkoxy, and —NR$^3$R$^4$ where R$^3$ and R$^4$ are independently selected from the group consisting of hydrogen and C$_1$-C$_4$ alkyl.

The term "cancer", as used herein, refers to any member of a class of diseases or disorders characterized by uncontrolled division of cells and the ability of these cells to invade other tissues, either by direct growth into adjacent tissue through invasion or by implantation into distant sites by metastasis. Metastasis is defined as the stage in which cancer cells are transported through the bloodstream or lymphatic system. Cancers are classified by the type of cells that the tumor resembles and, therefore, the tissue presumed to be the origin of the tumor. For example, carcinomas are malignant tumors derived from epithelial cells. This group represents the most common cancers, including the common forms of breast, prostate, lung, and colon cancer. Lymphomas and leukemias include malignant tumors derived from blood and bone marrow cells. Sarcomas are malignant tumors derived from connective tissue or mesenchymal cells. Mesotheliomas are tumors derived from the mesothelial cells lining the peritoneum and the pleura. Gliomas are tumors derived from glia, the most common type of brain cell. Germinomas are tumors derived from germ cells, normally found in the testicle and ovary. Choriocarcinomas are malignant tumors derived from the placenta.

The term "diagnosis" as used herein, refers to medical diagnosis, the process of determining which disease explain the symptoms of a subject.

The term "diagnostic composition" refers to a composition to be administered in a subject in order to perform a diagnosis and in particular an in vivo diagnosis. In one embodiment, a diagnostic composition is for detecting cells wherein the function of a vitamin transporter, in particular SMVT, is dysregulated, preferably within the body of a subject.

The term "envelope protein" ("Env", encoded by the env gene) refers to a protein synthesized as a single polyprotein, which is subsequently cleaved by a cellular furin-like PR domain into two components: the surface envelope protein ("SU protein" or gp70) and the transmembrane envelope protein ("TM protein" or p15E). The Env protein is glycosylated. The SU protein is responsible for binding with the host receptor. It comprises a receptor-binding domain ("RBD"). The TM protein, located inside the lipid bilayer anchors the SU protein to the surface of viral particles. The TM protein mediates the membrane fusion reaction with the host cell.

The term "identity", when used in a relationship between the sequences of two or more polypeptides or of two or more DNA sequences, refers to the degree of sequence relatedness between polypeptides or DNA sequences (respectively), as determined by the number of matches between strings of two or more amino acid residues or of two or more nucleotides, respectively. "Identity" measures the percent of identical matches between the smaller of two or more sequences with gap alignments (if any) addressed by a particular mathematical model or computer program (i.e., "algorithms") Identity of related polypeptides or DNA sequences can be readily calculated by known methods. Such methods include, but are not limited to, those described in Arthur M. Lesk, *Computational Molecular Biology: Sources and Methods for Sequence Analysis* (New-York: Oxford University Press, 1988); Douglas W. Smith, *Biocomputing: Informatics and Genome Projects* (New-York: Academic Press, 1993); Hugh G. Griffin and Annette M. Griffin, *Computer Analysis of Sequence Data, Part* 1 (New Jersey: Humana Press, 1994); Gunnar von Heinje, *Sequence Analysis in Molecular Biology: Treasure Trove or Trivial Pursuit* (Academic Press, 1987); Michael Gribskov and John Devereux, *Sequence Analysis Primer* (New York: M. Stockton Press, 1991); and Carillo et al., 1988. *SIAM J. Appl. Math.* 48(5): 1073-1082. Preferred methods for determining identity are designed to give the largest match between the sequences tested. Methods of determining identity are described in publicly available computer programs. Preferred computer program methods for determining identity between two sequences include the GCG program package, including GAP (Devereux et al., 1984. *Nucl. Acid. Res.* 12(1 Pt 1):387-395; Genetics Computer Group, University of Wisconsin Biotechnology Center, Madison, WI), BLASTP, BLASTN, TBLASTN and FASTA (Altschul et al., 1990. *J. Mol. Biol.* 215(3):403-410). The BLASTX program is publicly available from the National Center for Biotechnology Information (NCBI) and other sources (BLAST Manual, Altschul et al. NCB/NLM/NIH Bethesda, Md. 20894; Altschul et al., 1990. *J. Mol. Biol.* 215(3):403-410). The well-known Smith Waterman algorithm may also be used to determine identity.

The term "ligand" as used herein, refers to a small molecule (including but not limited to proteins, peptides, peptidomimetic compounds and other small molecule compounds) that binds specifically to another molecule.

The term "polypeptide" refers to a linear polymer of amino acids (preferably at least 50 amino acids) linked together by peptide bonds.

The terms "porcine endogenous retrovirus" and "PERV" refers to endogenous viruses that belong to the Ortervirales order, Retroviridae family, Orthoretrovirinae subfamily, *Gammaretrovirus* genus and *Porcine type-C oncovirus* species (International Committee on the Taxonomy of Viruses—ICTV; Krupovic et al., *J Virol.* 2018 May 29; 92(12)). As such, they have a single stranded RNA genome characterized by the presence of reverse transcriptase that allows the production of double stranded DNA, subsequently inserted in the genome of the host cells. The term "endogenous retrovirus" refers to the endogenous viral elements in the genome of a host species that become part of the transmitted genes by the host to its progeny. There are three replication-competent subtypes of PERV: porcine endogenous retrovirus type A (PERV-A), porcine endogenous retrovirus type B (PERV-B) and porcine endogenous retrovirus type C (PERV-C). PERV-A and PERV-B are polytropic, capable of infecting both porcine and human cells.

The term "protein" specifically refers to a functional entity formed of one or more polypeptides, and optionally of non-polypeptides cofactors.

The term "sample", as used herein, refers to any biological material obtained via suitable methods known to the person skilled in the art from a subject. The sample may be collected in a clinically acceptable manner, e.g., in a way that cells, nucleic acids (such as DNA and RNA), proteins and/or metabolites are preserved. A "sample" may include body tissue and/or bodily fluids.

The terms "sodium-dependent multivitamin transporter", "SMVT", "solute carrier family 5 member 6" and "SLC5A6" refers to a transmembrane protein present at the surface of cells in several organisms including, but not limited to, drosophila, zebrafish, rodents, pig, primates and human. SMVT belong to the group of solute carrier membrane transport protein that comprises over 400 identified members organized into 65 families. SMVT, like most member of the SLC group, is located in the plasma membrane where it is responsible for sodium-dependent uptake of biotin, pantothenic acid and lipoic acid. The protein bears 12 transmembrane domains with both amino and carboxyl termini predicted to be located on the cytoplasmic side. In human, the SMVT protein is the product of the SLC5A6 gene. SLC5A6 is expressed in various tissues including, but not limited to, placenta, intestine, brain, liver, lung, kidney, cornea, retina and heart. The modification of the level of SMVT, beyond reflecting the metabolic state of a cell, has also been associated with several diseases.

The term "SMVT-related diseases" refers to diseases associated with a modification (e.g., an overexpression or down-expression) of the level of SMVT at the surface of a subject cells. The term thus encompasses diseases associated with a deregulation of biotin, pantothenic acid and lipoid acid uptake such as for example embryonic growth retardation, neurological disorders and dermatological disorders. Furthermore, a variation of the expression of SMVT has been found associated with cancer, in particular liver cancer, prostate cancer, lung cancer, gallbladder cancer, pancreas cancer, colon cancer, ovarian cancer, brain cancer, kidney cancer and lymphomas.

The term "therapeutically effective amount" means level or amount of agent that is aimed at, without causing significant negative or adverse side effects to the target, (1) delaying or preventing the onset of a SMVT-related disease; (2) slowing down or stopping the progression, aggravation, or deterioration of one or more symptoms of a SMVT-related disease; (3) bringing about ameliorations of the symptoms of a SMVT-related disease; (4) reducing the severity or incidence of a SMVT-related disease; or (5) curing a SMVT-related disease. A therapeutically effective amount may be administered prior to the onset of a SMVT-related disease, for a prophylactic or preventive action. Alternatively or additionally, the therapeutically effective amount may be administered after initiation of a SMVT-related disease, for a therapeutic action.

The term "treatment" refers to both therapeutic treatment and prophylactic or preventive measures; wherein the object is to prevent or slow down (lessen) a SMVT-related disease. Those in need of treatment include those already with a SMVT-related disease as well as those prone to have a SMVT-related disease or those in whom a SMVT-related disease is to be prevented. A subject or mammal is successfully "treated" for a disease if, after receiving a therapeutic amount of a ligand according to the invention, the patient shows observable and/or measurable reduction in or absence of one or more of the following: reduction in the number of pathogenic cells; reduction in the percentage of total cells that are pathogenic; and/or relief to some extent, of one or more of the symptoms associated with the specific disease or condition; reduced morbidity and mortality, and improvement in quality of life issues. The above parameters for assessing successful treatment and improvement in the disease are readily measurable by routine procedures familiar to a physician.

The term "subject", as used herein, refers to an animal, preferably a mammal, more preferably a human. In one embodiment, the subject is a patient, i.e., a recipient of health care services, who/which is awaiting the receipt of, or is receiving medical care or was/is/will be the object of a medical procedure, or is monitored for the development of a disease.

The term "variant" refers to a polypeptide variant that typically differs from a polypeptide specifically disclosed herein in one or more substitutions, deletions, additions and/or insertions. Such variants may be naturally occurring or may be synthetically generated, for example, by modifying one or more of the above polypeptide sequences and evaluating one or more biological activities of the polypeptide as described herein and/or using any of a number of techniques well known in the art. Modifications may be made in the structure of polypeptides and still obtain a functional molecule that encodes a variant or derivative polypeptide with desirable characteristics. When it is desired to alter the amino acid sequence of a polypeptide to create an equivalent, or even an improved, variant or portion of a ligand of the invention, one skilled in the art will typically change one or more of the codons of the encoding DNA sequence. For example, certain amino acids may be substituted by other amino acids in a protein structure without appreciable loss of its ability to bind to a cell surface receptor, preferably to cell surface nutrient transporters, more preferably to SMVT. Since it is the binding capacity and nature of a protein that defines that protein's biological functional activity, certain amino acid sequence substitutions can be made in a protein sequence, and, of course, its underlying DNA coding sequence, and nevertheless obtain a protein with similar properties. It is thus contemplated that various changes may be made in the peptide sequences, or corresponding DNA sequences that encode said peptides without appreciable loss of their biological utility or activity. In many instances, a polypeptide variant will contain one or more conservative substitutions. A "conservative substitution" is one in which an amino acid is substituted by another amino acid that has similar properties, such that one skilled in the art of peptide chemistry would expect the secondary structure and hydropathic nature of the polypeptide to be substantially unchanged. As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skilled in the art and may include substitution within the following groups: arginine and lysine; glutamate and aspartate; serine and threonine; glutamine and asparagine; and valine, leucine and isoleucine. Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include histidine, lysine and arginine; and amino acids with uncharged polar head groups having similar hydrophilicity values include leucine, isoleucine and valine; glycine and alanine; asparagine and glutamine; and, serine, threonine, phenylalanine and tyrosine. Other groups of amino acids that may represent conservative changes include: (1) Ala, Pro, Gly, Glu, Asp, Gln, Asn, Ser, Thr; (2) Cys, Ser, Tyr, Thr; (3) Val, Ile, Leu, Met, Ala, Phe; (4) Lys, Arg, His; and (5) Phe, Tyr, Trp, His. The term "conservative amino acid substitution" may further be defined as an amino acid exchange within one of the following five groups: I: Small aliphatic, nonpolar or slightly polar residues: Ala, Ser, Thr, Pro, Gly; II: Polar, negatively charged residues and their amides: Asp, Asn, Glu, Gln; III: Polar, positively charged residues: His, Arg, Lys; IV: Large, aliphatic, nonpolar residues: Met, Leu, Ile, Val, Cys; V. Large, aromatic residues: Phe, Tyr, Trp. A variant may also, or alternatively, contain non-conservative changes. In a preferred embodiment, variant polypeptides differ from a native sequence by substitution, deletion or addition of 1, 2, 3, 4, 5, 6, 7, 8, 9 or 10 amino acids. Variants may also (or alternatively) be modified by, for example, the deletion or addition of amino acids that have minimal influence on the immunogenicity, secondary structure, hydropathic nature and/or binding properties of the polypeptide.

DETAILED DESCRIPTION

Figure 1:
FIG. 1 is a plot showing a representative example of the result of three independent automated screenings identifying SLC5A6/SMVT as the PERV-B.RBD cognate receptor among 172 soluble carrier family member. The fluorescence intensity (y-axis-positively correlating with the binding of PERV-B.RBD) is plotted for each of the SLC receptor tested (x-axis).

The present invention relates to in vitro methods for detecting and/or measuring the level of the cell surface nutrient transporter sodium-dependent multivitamin transporter (SMVT) in a biological sample, wherein said method comprises the steps of:
 a. contacting said biological sample with at least one PERV-B.RBD ligand, a variant and/or fragment thereof; and,
 b. detecting and/or measuring the binding of said PERV-B.RBD ligand, variant and/or fragment thereof to SMVT.

The present invention relates to in vitro methods for detecting and/or measuring the level of the cell surface nutrient transporter sodium-dependent multivitamin transporter (SMVT) in a biological sample, wherein said method comprises the steps of:
 a. contacting said biological sample with at least one PERV-B.RBD ligand, a variant and/or fragment thereof; and,
 b. measuring the binding of said PERV-B.RBD ligand, variant and/or fragment thereof to SMVT.

As used herein, the term PERV-B.RBD ligand refers to a receptor binding domain (RBD) ligand derived from the envelope protein of porcine endogenous retrovirus type B (PERV-B).

In one embodiment, the term "level of SMVT" refers to the amount of SMVT present at the surface of a cell and/or within the cell.

In one embodiment, the method of the invention is for assessing the expression level of SMVT present on the cell surface. In another embodiment, the method of the invention is for assessing the expression level of SMVT present within the cell.

In one embodiment, SMVT is human SMVT (UniProtKB—Q9Y289—SEQ ID NO: 1).

(SEQ ID NO: 1)
MSVGVSTSAPLSPTSGTSVGMSTFSIMDYVVFVLLLVLSLAIGLYHACRG

WGRHTVGELLMADRKMGCLPVALSLLATFQSAVAILGVPSEIYRFGTQYW

FLGCCYFLGLLIPAHIFIPVFYRLHLTSAYEYLELRFNKTVRVCGTVTFI

FQMVIYMGVVLYAPSLALNAVTGFDLWLSVLALGIVCTVYTALGGLKAVI

WTDVFQTLVMFLGQLAVIIVGSAKVGGLGRVWAVASQHGRISGFELDPDP

FVRHTFWTLAFGGVFMMLSLYGVNQAQVQRYLSSRTEKAAVLSCYAVFPF

QQVSLCVGCLIGLVMFAYYQEYPMSIQQAQAAPDQFVLYFVMDLLKGLPG

LPGLFIACLFSGSLSTISSAFNSLATVTMEDLIRPWFPEFSEARAIMLSR

GLAFGYGLLCLGMAYISSQMGPVLQAAISIFGMVGGPLLGLFCLGMFFPC

ANPPGAVVGLLAGLVMAFWIGIGSIVTSMGSSMPPSPSNGSSFSLPTNLT

VATVTTLMPLTTFSKPTGLQRFYSLSYLWYSAHNSTTVIVVGLIVSLLTG

RMRGRSLNPATIYPVLPKLLSLLPLSCQKRLHCRSYGQDHLDTGLFPEKP

RNGVLGDSRDKEAMALDGTAYQGSSSTCILQETSL

In one embodiment, SMVT is a human SMVT comprising or consisting of an amino acid sequence SEQ ID NO: 24.

In one embodiment, SMVT comprises or consists of an amino acid sequence presenting a sequence identity of at least about 70% with the amino acid sequence SEQ ID NO: 1, preferably a sequence identity of at least about 75%, 80%, 85%, 90%, 91%, 92%, 93%, 94%, 95%, 96%, 97%, 98%, 99% or more with the amino acid sequence SEQ ID NO: 1 or 24.

In one embodiment, SMVT comprises or consists of a fragment of SEQ ID NO: 1 or 24, preferably a fragment of at least about 100 amino acids, more preferably of at least about 150, 200, 250, 300, 350, 400, 450, 500, 550, 600 amino acids.

In one embodiment, the PERV-B.RBD ligand of the invention comprises a part or the totality of the receptor-binding domain (RBD) found in the surface component of the envelope protein (Env) of porcine endogenous retrovirus (PERV) that binds SMVT. In one embodiment, the PERV-B.RBD ligand of the invention comprises a part or the totality of the receptor-binding domain (RBD) found in the surface component of the envelope protein (Env) of porcine endogenous retrovirus type B (PERV-B) that binds SMVT.

In one embodiment, the PERV-B.RBD ligand of the invention comprises a part or the totality of the surface envelope protein. In one embodiment PERV-B.RBD ligand of the invention does not comprise the transmembrane domain of the envelope protein. Therefore, in one embodiment, the PERV-B.RBD ligand of the invention is a soluble peptide. As used herein, the term "soluble peptide" refers to a peptide which is not anchored within a membrane, such as, for example, by a transmembrane or a GPI anchor domain.

In one embodiment, the PERV-B.RBD ligand of the invention comprises a part or the totality of the receptor-binding domain (RBD) found in the soluble part of the envelope protein (Env) of porcine endogenous retrovirus-B (PERV-B) that binds to SMVT.

In one embodiment, the envelope protein of PERV-B comprises or consists of a sequence SEQ ID NO: 2 (Uniprot accession number: Q6W4T9—GenBank Accession number AAQ88198.1), or a sequence presenting a sequence identity of at least about 70%, preferably a sequence identity of at least about 75%, 80%, 85%, 90%, 91%, 92%, 93%, 94%, 95%, 96%, 97%, 98%, 99% or more, with the amino acid sequence SEQ ID NO: 2.

(SEQ ID NO: 2)
MHPTLSWRHLPTRGGEPKRLRIPLSFASIAWFLTLTITPQASSKRLIDSS

NPHRPLSLTWLIIDPDTGVTVNSTRGVAPRGTWWPELHFCLRLINPAVKS

TPPNLVRSYGFYCCPGTEKEKYCGGSEESFCRRWSCVTSNDGDWKWPISL

QDRVKFSFVNSGPGKYKVMKLYKDKSCSPSDLDYLKISFTEKGKQENIQK

WINGMSWGIVFYKYGGGAGSTLTIRLRIETGTEPPVAVGPDKVLAEQGPP

ALEPPHNLPVPQLTSLRPDITQPPSNGTTGLIPTNTPRNSPGVPVKTGQR

LFSLIQGAFQAINSTDPDATSSCWLCLSSGPPYYEGMAKEGKFNVTKEHR

NQCTWGSRNKLTLTEVSGKGTCIGKAPPSHQHLCYSTVVYEQASENQYLV

-continued
PGYNRWWACNTGLPPCVSSSVFNQSKDFCVMVQIVPRVYYHPEEVVLDEY

DYRYNRPKREPVSLTLAVMLGLGTAVGVGTGTAALITGPQQLEKGLGELH

AAMTEDLRALEESVSNLEESLTSLSEVVLQNRRGLDLLFLREGGLCAA

In another embodiment, the envelope protein of PERV-B comprises or consists of a sequence SEQ ID NO: 17, or a sequence presenting a sequence identity of at least about 70%, preferably a sequence identity of at least about 75%, 80%, 85%, 90%, 91%, 92%, 93%, 94%, 95%, 96%, 97%, 98%, 99% or more, with the amino acid sequence SEQ ID NO: 17.

(SEQ ID NO: 17)
MHPTLSWRHLPTRGGEPKRLRIPLSFASIAWFLTLTITPQASSKRLIDSS

NPHRPLSLTWLIIDPDTGVTVNSTRGVAPRGTWWPELHFCLRLINPAVKS

TPPNLVRSYGFYCCPGTEKEKYCGGSGESFCRRWSCVTSNDGDWKWPISL

QDRVKFSFVNSGPGKYKVMKLYKDKSCSPSDLDYLKISFTEKGKQENIQK

WINGMSWGIVFYKYGGGAGSTLTIRLRIETGTEPPVAVGPDKVLAEQGPP

ALEPPHNLPVPQLTSLRPDITQPPSNGTTGLIPTNTPRNSPGVPVKTGQR

LFSLIQGAFQAINSTDPDATSSCWLCLSSGPPYYEGMAKEGKFNVTKEHR

NQCTWGSRNKLTLTEVSGKGTCIGKAPPSHQHLCYSTVVYEQASENQYLV

PGYNRWWACNTGLTPCVSTSVFNQSKDFCVMVQIVPRVYYHPEEVVLDEY

DYRYNRPKREPVSLTLAVMLGLGTAVGVGTGTAALITGPQQLEKGLGELH

AAMTEDLRALEESVSNLEESLTSLSEVVLQNRRGLDLLFLREGGLCAA

In another embodiment, the envelope protein of PERV-B comprises or consists of a sequence SEQ ID NO: 25, or a sequence presenting a sequence identity of at least about 70%, preferably a sequence identity of at least about 75%, 80%, 85%, 90%, 91%, 92%, 93%, 94%, 95%, 96%, 97%, 98%, 99% or more, with the amino acid sequence SEQ ID NO: 25.

(SEQ ID NO: 25)
MHPTLSWRHLPTRGGEPKRLRIPLSFASIAWFLTLTITPQASSKRLIDSS

NPHRPLSLTWLIIDPDTGVTVNSTRGVAPRGTWWPELHFCLRLINPAVKS

TPPNLVRSYGFYCCPGTEKEKYCGGSEESFCRRWSCVTSNDGDWKWPISL

QDRVKFSFVNSGPGKYKVMKLYKDKSCSPSDLDYLKISFTEKGKQENIQK

WINGMSWGIVFYKYGGGAGSTLTIRLRIETGTEPPVAVGPDKVLAEQGPP

ALEPPHNLPVPQLTSLRPDITQPPSNGTTGLIPTNTPRNSPGVPVKTGQR

LFSLIQGAFQAINSTDPDATSSCWLCLSSGPPYYEGMAKEGKFNVTKEHR

NQCTWGSRNKLTLTEVSGKGTCIGKAPPSHQHLCYSTVVYEQASENQYLV

PGYNRWWACNTGLTPCVSSSVFNQSKDFCVMVQIVPRVYYHPEEVVLDEY

DYRYNRPKREPVSLTLAVMLGLGTAVGVGTGTAALITGPQQLEKGLGELH

AAMTEDLRALEESVSNLEESLTSLSEVVLQNRRGLDLLFLREGGLCAA

In one embodiment, the amino-acid sequence of the PERV-B.RBD ligand of the invention comprises or consists of a fragment of SEQ ID NO: 2, 17 or 25, or a variant thereof.

In one embodiment, the amino-acid sequence of the PERV-B.RBD ligand of the invention comprises or consists of amino acids 1 to 540, preferably 1 to 530, 1 to 520, 1 to 510, 1 to 500, 1 to 490, 1 to 480, 1 to 490, 1 to 480, 1 to 470, 1 to 460, 1 to 450, 1 to 440, 1 to 430, 1 to 420, 1 to 410, 1 to 400, 1 to 390, 1 to 380, 1 to 370, 1 to 360, 1 to 350, 1 to 340, 1 to 330, 1 to 320, 1 to 310, 1 to 300, 1 to 290, 1 to 280, 1 to 270, 1 to 260, 1 to 250, 1 to 240, more preferably 1 to 238 of SEQ ID NO: 2, 17 or 25, or a variant thereof.

In one embodiment, the amino-acid sequence of the PERV-B.RBD ligand of the invention does not comprise a signal peptide, preferably does not comprise a signal peptide of amino sequence SEQ ID NO: 3 or a sequence presenting a sequence identity of at least about 70%, preferably a sequence identity of at least about 75%, 80%, 85%, 90%, 91%, 92%, 93%, 94%, 95%, 96%, 97%, 98%, 99% or more, with the amino acid sequence SEQ ID NO: 3. In one embodiment, the amino-acid sequence of the PERV-B.RBD ligand of the invention does not comprise a signal peptide corresponding to the first 38, 39, 40, 41 or 42 amino acids of SEQ ID NO: 3.

(SEQ ID NO: 3)
MHPTLSWRHLPTRGGEPKRLRIPLSFASIAWFLTLTITPQASS

In one embodiment, the amino-acid sequence of the PERV-B.RBD ligand of the invention comprises or consists of amino acids 44 to 540, preferably 44 to 530, 44 to 520, 44 to 510, 44 to 500, 44 to 490, 44 to 480, 44 to 470, 44 to 460, 44 to 450, 44 to 440, 44 to 430, 44 to 420, 44 to 410, 44 to 400, 44 to 390, 44 to 380, 44 to 370, 44 to 360, 44 to 350, 44 to 340, 44 to 330, 44 to 320, 44 to 310, 44 to 300, 44 to 290, 44 to 280, 44 to 270, 44 to 260, 44 to 250, 44 to 240, more preferably 44 to 238 of SEQ ID NO: 2, 17 or 25, or variants thereof.

In one embodiment, the amino-acid sequence of the PERV-B.RBD ligand of the invention comprises or consists of amino acids 39, 40, 41, 42, 43, 44, 45, 46, 47, 48 or 49 to 540, preferably 39, 40, 41, 42, 43, 44, 45, 46, 47, 48 or 49 to 530; 39, 40, 41, 42, 43, 44, 45, 46, 47, 48 or 49 to 520; 39, 40, 41, 42, 43, 44, 45, 46, 47, 48 or 49 to 510; 39, 40, 41, 42, 43, 44, 45, 46, 47, 48 or 49 to 500; 39, 40, 41, 42, 43, 44, 45, 46, 47, 48 or 49 to 490; 39, 40, 41, 42, 43, 44, 45, 46, 47, 48 or 49 to 480; 39, 40, 41, 42, 43, 44, 45, 46, 47, 48 or 49 to 470, 39, 40, 41, 42, 43, 44, 45, 46, 47, 48 or 49 to 460; 39, 40, 41, 42, 43, 44, 45, 46, 47, 48 or 49 to 450; 39, 40, 41, 42, 43, 44, 45, 46, 47, 48 or 49 to 440; 39, 40, 41, 42, 43, 44, 45, 46, 47, 48 or 49 to 430; 39, 40, 41, 42, 43, 44, 45, 46, 47, 48 or 49 to 420; 39, 40, 41, 42, 43, 44, 45, 46, 47, 48 or 49 to 410; 39, 40, 41, 42, 43, 44, 45, 46, 47, 48 or 49 to 400; 39, 40, 41, 42, 43, 44, 45, 46, 47, 48 or 49 to 390; 39, 40, 41, 42, 43, 44, 45, 46, 47, 48 or 49 to 380; 39, 40, 41, 42, 43, 44, 45, 46, 47, 48 or 49 to 370; 39, 40, 41, 42, 43, 44, 45, 46, 47, 48 or 49 to 360; 39, 40, 41, 42, 43, 44, 45, 46, 47, 48 or 49 to 350; 39, 40, 41, 42, 43, 44, 45, 46, 47, 48 or 49 to 340; 39, 40, 41, 42, 43, 44, 45, 46, 47, 48 or 49 to 330; 39, 40, 41, 42, 43, 44, 45, 46, 47, 48 or 49 to 320; 39, 40, 41, 42, 43, 44, 45, 46, 47, 48 or 49 to 310; 39, 40, 41, 42, 43, 44, 45, 46, 47, 48 or 49 to 300; 39, 40, 41, 42, 43, 44, 45, 46, 47, 48 or 49 to 290; 39, 40, 41, 42, 43, 44, 45, 46, 47, 48 or 49 to 280; 39, 40, 41, 42, 43, 44, 45, 46, 47, 48 or 49 to 270; 39, 40, 41, 42, 43, 44, 45, 46, 47, 48 or 49 to 260; 39, 40, 41, 42, 43, 44, 45, 46, 47, 48 or 49 to 250; 39, 40, 41, 42, 43, 44, 45, 46, 47, 48 or 49 to 240; more preferably 39, 40, 41, 42, 43, 44, 45, 46, 47, 48 or 49 to 238 of SEQ ID NO: 2, 17 or 25, or variants thereof.

In one embodiment, the amino-acid sequence of the PERV-B.RBD ligand of the invention comprises or consists of an amino acid sequence presenting a sequence identity of at least about 70%, preferably a sequence identity of at least about 75%, 80%, 85%, 90%, 91%, 92%, 93%, 94%, 95%, 96%, 97%, 98%, 99% or more, with the amino acid sequence SEQ ID NO: 2, 17 or 25, a variant and/or a fragment thereof.

In one embodiment, the amino-acid sequence of the PERV-B.RBD ligand of the invention comprises or consists of the amino acid sequence of an SU domain of the Env protein of porcine endogenous retrovirus-B (SEQ ID NO: 4), a variant and/or a fragment thereof.

```
                                        (SEQ ID NO: 4)
MHPTLSWRHLPTRGGEPKRLRIPLSFASIAWFLTLTITPQASSKRLIDSS

NPHRPLSLTWLIIDPDTGVTVNSTRGVAPRGTWWPELHFCLRLINPAVKS

TPPNLVRSYGFYCCPGTEKEKYCGGSEESFCRRWSCVTSNDGDWKWPISL

QDRVKFSFVNSGPGKYKVMKLYKDKSCSPSDLDYLKISFTEKGKQENIQK

WINGMSWGIVFYKYGGGAGSTLTIRLRIETGTEPPVAVGPDKVLAEQGPP

ALEPPHNLPVPQLTSLRPDITQPPSNGTTGLIPTNTPRNSPGVPVKTGQR

LFSLIQGAFQAINSTDPDATSSCWLCLSSGPPYYEGMAKEGKFNVTKEHR

NQCTWGSRNKLTLTEVSGKGTCIGKAPPSHQHLCYSTVVYEQASENQYLV

PGYNRWWACNTGLPPCVSSSVFNQSKDFCVMVQIVPRVYYHPEEVVLDEY

DYRYNRPKR
```

In one embodiment, the amino-acid sequence of the PERV-B.RBD ligand of the invention comprises or consists of the amino acid sequence of an SU domain of the Env protein of porcine endogenous retrovirus-B (SEQ ID NO: 18), a variant and/or a fragment thereof.

```
                                       (SEQ ID NO: 18)
MHPTLSWRHLPTRGGEPKRLRIPLSFASIAWFLTLTITPQASSKRLIDSS

NPHRPLSLTWLIIDPDTGVTVNSTRGVAPRGTWWPELHFCLRLINPAVKS

TPPNLVRSYGFYCCPGTEKEKYCGGSGESFCRRWSCVTSNDGDWKWPISL

QDRVKFSFVNSGPGKYKVMKLYKDKSCSPSDLDYLKISFTEKGKQENIQK

WINGMSWGIVFYKYGGGAGSTLTIRLRIETGTEPPVAVGPDKVLAEQGPP

ALEPPHNLPVPQLTSLRPDITQPPSNGTTGLIPTNTPRNSPGVPVKTGQR

LFSLIQGAFQAINSTDPDATSSCWLCLSSGPPYYEGMAKEGKFNVTKEHR

NQCTWGSRNKLTLTEVSGKGTCIGKAPPSHQHLCYSTVVYEQASENQYLV

PGYNRWWACNTGLTPCVSTSVFNQSKDFCVMVQIVPRVYYHPEEVVLDEY

DYRYNRPKR
```

In one embodiment, the amino-acid sequence of the PERV-B.RBD ligand of the invention comprises or consists of the amino acid sequence of an SU domain of the Env protein of porcine endogenous retrovirus-B (SEQ ID NO: 26), a variant and/or a fragment thereof.

```
                                       (SEQ ID NO: 26)
MHPTLSWRHLPTRGGEPKRLRIPLSFASIAWFLTLTITPQASSKRLIDSS

NPHRPLSLTWLIIDPDTGVTVNSTRGVAPRGTWWPELHFCLRLINPAVKS

TPPNLVRSYGFYCCPGTEKEKYCGGSEESFCRRWSCVTSNDGDWKWPISL
```

-continued

```
QDRVKFSFVNSGPGKYKVMKLYKDKSCSPSDLDYLKISFTEKGKQENIQK

WINGMSWGIVFYKYGGGAGSTLTIRLRIETGTEPPVAVGPDKVLAEQGPP

ALEPPHNLPVPQLTSLRPDITQPPSNGTTGLIPTNTPRNSPGVPVKTGQR

LFSLIQGAFQAINSTDPDATSSCWLCLSSGPPYYEGMAKEGKFNVTKEHR

NQCTWGSRNKLTLTEVSGKGTCIGKAPPSHQHLCYSTVVYEQASENQYLV

PGYNRWWACNTGLTPCVSSSVFNQSKDFCVMVQIVPRVYYHPEEVVLDEY

DYRYNRPKR
```

In one embodiment, the amino-acid sequence of the PERV-B.RBD ligand of the invention comprises or consists of amino acids 1 to 480, preferably of 1 to 470, 1 to 460, 1 to 450, 1 to 440, 1 to 430, 1 to 420, 1 to 410, 1 to 400, 1 to 390, 1 to 380, 1 to 370, 1 to 360, 1 to 350, 1 to 340, 1 to 330, 1 to 320, 1 to 310, 1 to 300, 1 to 290, 1 to 280, 1 to 270, 1 to 260, 1 to 250, 1 to 240, more preferably 1 to 238 of SEQ ID NO: 4, 18 or 26, or a variant thereof.

In one embodiment, the amino-acid sequence of the PERV-B.RBD ligand of the invention comprises or consists of amino acids 44 to 480, preferably of 44 to 470, 44 to 460, 44 to 450, 44 to 440, 44 to 430, 44 to 420, 44 to 410, 44 to 400, 44 to 390, 44 to 380, 44 to 370, 44 to 360, 44 to 350, 44 to 340, 44 to 330, 44 to 320, 44 to 310, 44 to 300, 44 to 290, 44 to 280, 44 to 270, 44 to 260, 44 to 250, 44 to 240, more preferably 44 to 238 of SEQ ID NO: 4, 18 or 26, or a variant thereof.

In one embodiment, the amino-acid sequence of the PERV-B.RBD ligand of the invention comprises or consists of amino acids 39, 40, 41, 42, 43, 44, 45, 46, 47, 48 or 49 to 480; preferably of 39, 40, 41, 42, 43, 44, 45, 46, 47, 48 or 49 to 470; 39, 40, 41, 42, 43, 44, 45, 46, 47, 48 or 49 to 460; 39, 40, 41, 42, 43, 44, 45, 46, 47, 48 or 49 to 450; 39, 40, 41, 42, 43, 44, 45, 46, 47, 48 or 49 to 440; 39, 40, 41, 42, 43, 44, 45, 46, 47, 48 or 49 to 430; 39, 40, 41, 42, 43, 44, 45, 46, 47, 48 or 49 to 420; 39, 40, 41, 42, 43, 44, 45, 46, 47, 48 or 49 to 410; 39, 40, 41, 42, 43, 44, 45, 46, 47, 48 or 49 to 400; 39, 40, 41, 42, 43, 44, 45, 46, 47, 48 or 49 to 390; 39, 40, 41, 42, 43, 44, 45, 46, 47, 48 or 49 to 380; 39, 40, 41, 42, 43, 44, 45, 46, 47, 48 or 49 to 370; 39, 40, 41, 42, 43, 44, 45, 46, 47, 48 or 49 to 360; 39, 40, 41, 42, 43, 44, 45, 46, 47, 48 or 49 to 350; 39, 40, 41, 42, 43, 44, 45, 46, 47, 48 or 49 to 340; 39, 40, 41, 42, 43, 44, 45, 46, 47, 48 or 49 to 330; 39, 40, 41, 42, 43, 44, 45, 46, 47, 48 or 49 to 320; 39, 40, 41, 42, 43, 44, 45, 46, 47, 48 or 49 to 310; 39, 40, 41, 42, 43, 44, 45, 46, 47, 48 or 49 to 300; 39, 40, 41, 42, 43, 44, 45, 46, 47, 48 or 49 to 290; 39, 40, 41, 42, 43, 44, 45, 46, 47, 48 or 49 to 280; 39, 40, 41, 42, 43, 44, 45, 46, 47, 48 or 49 to 270; 39, 40, 41, 42, 43, 44, 45, 46, 47, 48 or 49 to 260; 39, 40, 41, 42, 43, 44, 45, 46, 47, 48 or 49 to 250; 39, 40, 41, 42, 43, 44, 45, 46, 47, 48 or 49 to 240; more preferably 39, 40, 41, 42, 43, 44, 45, 46, 47, 48 or 49 to 238 of SEQ ID NO: 4, 18 or 26, or a variant thereof.

In one embodiment, the amino-acid sequence of the PERV-B.RBD ligand of the invention comprises or consists of an amino acid sequence presenting a sequence identity of at least about 70%, preferably a sequence identity of at least about 75%, 80%, 85%, 90%, 91%, 92%, 93%, 94%, 95%, 96%, 97%, 98%, 99% or more, with the amino acid sequence SEQ ID NO: 4, 18 or 26, a variant and/or a fragment thereof.

In one embodiment, the amino-acid sequence of the PERV-B.RBD ligand of the invention comprises or consists of the amino acid sequence SEQ ID NO: 5, a variant and/or a fragment thereof.

(SEQ ID NO: 5)
MHPTLSWRHLPTRGGEPKRLRIPLSFASIAWFLTLTITPQASSKRLIDSS

NPHRPLSLTWLIIDPDTGVTVNSTRGVAPRGTWWPELHFCLRLINPAVKS

TPPNLVRSYGFYCCPGTEKEKYCGGSEESFCRRWSCVTSNDGDWKWPISL

QDRVKFSFVNSGPGKYKVMKLYKDKSCSPSDLDYLKISFTEKGKQENIQK

WINGMSWGIVFYKYGGGAGSTLTIRLRIEAGTEPPVAV

In one embodiment, the amino-acid sequence of the PERV-B.RBD ligand of the invention comprises or consists of the amino acid sequence SEQ ID NO: 19, a variant and/or fragment thereof.

(SEQ ID NO: 19)
MHPTLSWRHLPTRGGEPKRLRIPLSFASIAWFLTLTITPQASSKRLIDSS

NPHRPLSLTWLIIDPDTGVTVNSTRGVAPRGTWWPELHFCLRLINPAVKS

TPPNLVRSYGFYCCPGTEKEKYCGGSGESFCRRWSCVTSNDGDWKWPISL

QDRVKFSFVNSGPGKYKVMKLYKDKSCSPSDLDYLKISFTEKGKQENIQK

WINGMSWGIVFYKYGGGAGSTLTIRLRIETGTEPPVAV

In one embodiment, the amino-acid sequence of the PERV-B.RBD ligand of the invention comprises or consists of the amino acid sequence SEQ ID NO: 21, a variant and/or a fragment thereof.

(SEQ ID NO: 21)
MHPTLSWRHLPTRGGEPKRLRIPLSFASIAWFLTLTITPQASSKRLIDSS

NPHRPLSLTWLIIDPDTGVTVNSTRGVAPRGTWWPELHFCLRLINPAVKS

TPPNLVRSYGFYCCPGTEKEKYCGGSEESFCRRWSCVTSNDGDWKWPISL

QDRVKFSFVNSGPGKYKVMKLYKDKSCSPSDLDYLKISFTEKGKQENIQK

WINGMSWGIVFYKYGGGAGSTLTIRLRIETGTEPPVAV

In one embodiment, the amino-acid sequence of the PERV-B.RBD ligand of the invention comprises or consists of an amino acid sequence presenting a sequence identity of at least about 70%, preferably a sequence identity of at least about 75%, 80%, 85%, 90%, 91%, 92%, 93%, 94%, 95%, 96%, 97%, 98%, 99% or more, with the amino acid sequence SEQ ID NO: 5, 19 or 21, a variant and/or a fragment thereof.

In one embodiment, the amino-acid sequence of the PERV-B.RBD ligand of the invention comprises or consists of amino acids 44 to 238 of SEQ ID NO: 5, 19 or 21, or a variant thereof.

In one embodiment, the amino-acid sequence of the PERV-B.RBD ligand of the invention comprises or consists of amino acids 39, 40, 41, 42, 43, 44, 45, 46, 47, 48 or 49 to 238 of SEQ ID NO: 5, 19 or 21, or a variant thereof.

In one embodiment, the amino-acid sequence of the PERV-B.RBD ligand of the invention comprises or consists of the amino acid sequence SEQ ID NO: 6, a variant and/or a fragment thereof.

(SEQ ID NO: 6)
KRLIDSSNPHRPLSLTWLIIDPDTGVTVNSTRGVAPRGTWWPELHFCLRL

INPAVKSTPPNLVRSYGFYCCPGTEKEKYCGGSEESFCRRWSCVTSNDGD

WKWPISLQDRVKFSFVNSGPGKYKVMKLYKDKSCSPSDLDYLKISFTEKG

KQENIQKWINGMSWGIVFYKYGGGAGSTLTIRLRIEAGTEPPVAV

In one embodiment, the amino-acid sequence of the PERV-B.RBD ligand of the invention comprises or consists of the amino acid sequence SEQ ID NO: 20, a variant and/or a fragment thereof.

(SEQ ID NO: 20)
KRLIDSSNPHRPLSLTWLIIDPDTGVTVNSTRGVAPRGTWWPELHFCLRL

INPAVKSTPPNLVRSYGFYCCPGTEKEKYCGGSGESFCRRWSCVTSNDGD

WKWPISLQDRVKFSFVNSGPGKYKVMKLYKDKSCSPSDLDYLKISFTEKG

KQENIQKWINGMSWGIVFYKYGGGTGSTLTIRLRIETGTEPPVAV

In one embodiment, the amino-acid sequence of the PERV-B.RBD ligand of the invention comprises or consists of the amino acid sequence SEQ ID NO: 22, a variant and/or a fragment thereof.

(SEQ ID NO: 22)
KRLIDSSNPHRPLSLTWLIIDPDTGVTVNSTRGVAPRGTWWPELHFCLRL

INPAVKSTPPNLVRSYGFYCCPGTEKEKYCGGSEESFCRRWSCVTSNDGD

WKWPISLQDRVKFSFVNSGPGKYKVMKLYKDKSCSPSDLDYLKISFTEKG

KQENIQKWINGMSWGIVFYKYGGGAGSTLTIRLRIETGTEPPVAV

In one embodiment, the amino-acid sequence of the PERV-B.RBD ligand of the invention comprises or consists of amino acids 2, 3, 4, 5, or 6 to 195 of SEQ ID NO: 6, 20 or 22, or a variant thereof.

In one embodiment, the amino-acid sequence of the PERV-B.RBD ligand of the invention comprises or consists of amino acids 39, 40, 41, 42, 43, 44, 45, 46, 47, 48 or 49 to 238 of SEQ ID NO: 2, 17, 25, 4, 18, 26, 5, 19 or 21, or a variant thereof.

In one embodiment, the amino-acid sequence of the PERV-B.RBD ligand of the invention comprises or consists of an amino acid sequence presenting a sequence identity of at least about 70%, preferably a sequence identity of at least about 75%, 80%, 85%, 90%, 91%, 92%, 93%, 94%, 95%, 96%, 97%, 98%, 99% or more, with the amino acid sequence SEQ ID NO: 6, 20 or 22, a variant and/or a fragment thereof.

In one embodiment, the amino-acid sequence of the PERV-B.RBD ligand of the invention comprises or consists of an amino acid sequence presenting a sequence identity of at least about 70%, preferably a sequence identity of at least about 75%, 80%, 85%, 90%, 91%, 92%, 93%, 94%, 95%, 96%, 97%, 98%, 99% or more, with the amino acid sequence SEQ ID NO: 5, 19 or 21, a variant and/or a fragment thereof.

In one embodiment, the amino-acid sequence of the PERV-B.RBD ligand of the invention comprises or consists of the amino acid sequence selected from the group comprising or consisting of the amino acid sequences SEQ ID NO: 2, 4, 5, 6, 17, 18, 19, 20, 21 and 22 and, variants and/or fragments thereof.

In one embodiment, the amino-acid sequence of the PERV-B.RBD ligand of the invention comprises or consists of the amino acid sequence selected from the group comprising or consisting of the amino acid sequences SEQ ID NO: 2, 4, 5, 6, 17, 18, 19, 20, 21, 22, 25 and 26, variants and/or fragments thereof.

In one embodiment, the amino-acid sequence of the PERV-B.RBD ligand of the invention comprises or consists of an amino acid sequence presenting a sequence identity of at least about 70%, preferably a sequence identity of at least about 75%, 80%, 85%, 90%, 91%, 92%, 93%, 94%, 95%, 96%, 97%, 98%, 99% or more, with an amino acid sequence selected from the group comprising or consisting of the amino acid sequences SEQ ID NO: 2, 4, 5, 6, 17, 18, 19, 20, 21 and 22 and, variants and/or fragments thereof.

In one embodiment, the amino-acid sequence of the PERV-B.RBD ligand of the invention comprises or consists of an amino acid sequence presenting a sequence identity of at least about 70%, preferably a sequence identity of at least about 75%, 80%, 85%, 90%, 91%, 92%, 93%, 94%, 95%, 96%, 97%, 98%, 99% or more, with an amino acid sequence selected from the group comprising or consisting of the amino acid sequences SEQ ID NO: 2, 4, 5, 6, 17, 18, 19, 20, 21, 22, 25 and 26 and, variants and/or fragments thereof.

In one embodiment, the amino-acid sequence of the PERV-B.RBD ligand of the invention comprises or consists of the amino acid sequence selected from the group comprising or consisting of the amino acid sequences SEQ ID NO: 5, 6, 19, 20, 21 and 22 and, variants and/or fragments thereof.

In one embodiment, the amino-acid sequence of the PERV-B.RBD ligand of the invention comprises or consists of the amino acid sequence selected from the group comprising or consisting of the amino acid sequences SEQ ID NO: 5, 19, and 21 and, variants and/or fragments thereof.

In one embodiment, the nucleic acid sequence encoding the PERV-B.RBD ligand of the invention, a variant and/or a fragment thereof, comprises or consists of the nucleic acid sequence SEQ ID NO: 7, a variant and/or a fragment thereof.

(SEQ ID NO: 7)
ATGCATCCCACGTTAAGCTGGCGCCACCTCCCGACTCGGGGTGGAGAGCC

GAAAAGACTGAGAATCCCCTTAAGCTTCGCCTCCATCGCCTGGTTCCTTA

CTCTAACAATAACTCCCCAGGCCAGTAGTAAACGCCTTATAGACAGCTCG

AACCCCCATAGACCTTTATCCCTTACCTGGCTGATTATTGACCCTGATAC

GGGTGTCACTGTAAATAGCACTCGAGGTGTTGCTCCTAGAGGCACCTGGT

GGCCTGAACTGCATTTCTGCCTCCGATTGATTAACCCCGCTGTTAAAAGC

ACACCTCCCAACCTAGTCCGTAGTTATGGGTTCTATTGCTGCCCAGGCAC

AGAGAAAGAGAAATACTGTGGGGGTTCTGAGGAATCCTTCTGTAGGAGAT

GGAGCTGCGTCACCTCCAACGATGGAGACTGGAAATGGCCGATCTCTCTC

CAGGACCGGGTAAAATTCTCCTTTGTCAATTCCGGCCCGGGCAAGTACAA

AGTGATGAAACTATATAAAGATAAGAGCTGCTCCCCATCAGACTTAGATT

ATCTAAAGATAAGTTTCACTGAAAAAGGAAAACAGGAAAATATTCAAAAG

TGGATAAATGGTATGAGCTGGGGAATAGTTTTTTATAAATATGGCGGGGG

AGCAGGGTCCACTTTAACCATTCGCCTTAGGATAGAGGCGGGGACAGAAC

CCCCTGTGGCAGTG

In one embodiment, the nucleic acid sequence encoding the PERV-B.RBD ligand of the invention, a variant and/or a fragment thereof, comprises or consists of a nucleic acid sequence presenting a sequence identity of at least about 70%, preferably a sequence identity of at least about 75%, 80%, 85%, 90%, 91%, 92%, 93%, 94%, 95%, 96%, 97%, 98%, 99% or more, with the nucleic acid sequence SEQ ID NO: 7, a variant and/or a fragment thereof.

In one embodiment, the nucleic acid sequence encoding the PERV-B.RBD ligand of the invention, a variant and/or a fragment thereof, comprises or consists of the nucleic acid sequence SEQ ID NO: 8, a variant and/or a fragment thereof.

(SEQ ID NO: 8)
AAACGCCTTATAGACAGCTCGAACCCCCATAGACCTTTATCCCTTACCTG

GCTGATTATTGACCCTGATACGGGTGTCACTGTAAATAGCACTCGAGGTG

TTGCTCCTAGAGGCACCTGGTGGCCTGAACTGCATTTCTGCCTCCGATTG

ATTAACCCCGCTGTTAAAAGCACACCTCCCAACCTAGTCCGTAGTTATGG

GTTCTATTGCTGCCCAGGCACAGAGAAAGAGAAATACTGTGGGGGTTCTG

AGGAATCCTTCTGTAGGAGATGGAGCTGCGTCACCTCCAACGATGGAGAC

TGGAAATGGCCGATCTCTCTCCAGGACCGGGTAAAATTCTCCTTTGTCAA

TTCCGGCCCGGGCAAGTACAAAGTGATGAAACTATATAAAGATAAGAGCT

GCTCCCCATCAGACTTAGATTATCTAAAGATAAGTTTCACTGAAAAAGGA

AAACAGGAAAATATTCAAAAGTGGATAAATGGTATGAGCTGGGGAATAGT

TTTTTATAAATATGGCGGGGAGCAGGGTCCACTTTAACCATTCGCCTTA

GGATAGAGGCGGGGACAGAACCCCCTGTGGCAGTG

In one embodiment, the nucleic acid sequence encoding the PERV-B.RBD ligand of the invention, a variant and/or a fragment thereof, comprises or consists of a nucleic acid sequence presenting a sequence identity of at least 70%, preferably a sequence identity of at least about 75%, 80%, 85%, 90%, 91%, 92%, 93%, 94%, 95%, 96%, 97%, 98%, 99% or more, with the nucleic acid sequence SEQ ID NO: 8, a variant and/or a fragment thereof.

In one embodiment, the nucleic acid sequence encoding the PERV-B.RBD ligand of the invention, a variant and/or a fragment thereof, comprises or consists of the nucleic acid sequence SEQ ID NO: 27, a variant and/or a fragment thereof.

(SEQ ID NO: 27)
ATGCATCCCACGTTAAGCTGGCGCCACCTCCCGACTCGGGGTGGAGAGCC

GAAAAGACTGAGAATCCCCTTAAGCTTCGCCTCCATCGCCTGGTTCCTTA

CTCTAACAATAACTCCCCAGGCCAGTAGTAAACGCCTTATAGACAGCTCG

AACCCCCATAGACCTTTATCCCTTACCTGGCTGATTATTGACCCTGATAC

GGGTGTCACTGTAAATAGCACTCGAGGTGTTGCTCCTAGAGGCACCTGGT

GGCCTGAACTGCATTTCTGCCTCCGATTGATTAACCCCGCTGTTAAAAGC

ACACCTCCCAACCTAGTCCGTAGTTATGGGTTCTATTGCTGCCCAGGCAC

AGAGAAAGAGAAATACTGTGGGGGTTCTGAGGAATCCTTCTGTAGGAGAT

GGAGCTGCGTCACCTCCAACGATGGAGACTGGAAATGGCCGATCTCTCTC

CAGGACCGGGTAAAATTCTCCTTTGTCAATTCCGGCCCGGGCAAGTACAA

AGTGATGAAACTATATAAAGATAAGAGCTGCTCCCCATCAGACTTAGATT

ATCTAAAGATAAGTTTCACTGAAAAAGGAAAACAGGAAAATATTCAAAAG

TGGATAAATGGTATGAGCTGGGGAATAGTTTTTTATAAATATGGCGGGGG

-continued

```
AGCAGGGTCCACTTTAACCATTCGCCTTAGGATAGAGACGGGGACAGAAC

CCCCTGTGGCAGTG
```

In one embodiment, the nucleic acid sequence encoding the PERV-B.RBD ligand of the invention, a variant and/or a fragment thereof, comprises or consists of a nucleic acid sequence presenting a sequence identity of at least 70%, preferably a sequence identity of at least about 75%, 80%, 85%, 90%, 91%, 92%, 93%, 94%, 95%, 96%, 97%, 98%, 99% or more, with the nucleic acid sequence SEQ ID NO: 27, a variant and/or a fragment thereof.

In one embodiment, the PERV-B.RBD ligand of the invention, a variant and/or a fragment thereof, is labeled with a detectable label.

The present invention thus relates to a PERV-B.RBD ligand as described herein, wherein said RBD ligand is coupled to a detectable label.

Examples of detectable labels include, but are not limited to, radioactive labels, paramagnetic metals, fluorescents labels and peptidic tags.

In one embodiment, the PERV-B.RBD ligand of the invention, a variant and/or a fragment thereof, is labeled with a radioactive label. Examples of radioactive labels include, but are not limited to, non-metallic radioisotopes and radioactive metals.

Examples of non-metallic radioisotopes comprise, but are not limited to, I-125, I-123, I-131, C-11, F-18, Br-75, Br-76, Br-77, Br-80, and At-211. The non-metallic radioisotopes may be conjugated covalently to either terminus of the ligand, functional groups of amino acid side chains, be part of a linear stabilized peptide as an additional substituent, e.g., in an amino acid phenylalanine or tyrosine carrying fluorine, bromine or iodine, or as an additional substituent carboxy or methyl, or as a replacement of any regular carbon atom in the ligand. These radioisotopes are useful in ligands as positron emission tomography (PET) probes or as single-photon emission computed tomography (SPECT) probes.

Examples of radioactive metals include, but are not limited to, Cu-64, Cu-67, Ga-67, Ga-68, Zr-89, Y-90, Tc-99m, In-111, Tb-161, Lu-177, Re-186, Re-188, and Bi-213. The radioactive metals may be covalently attached to the ligands, directly connected to the ligands or through a spacer.

In one embodiment, the PERV-B.RBD ligand of the invention, a variant and/or a fragment thereof, is labeled with paramagnetic metals.

Examples of paramagnetic metals comprise, but are not limited to, Gd, Fe, Mn. The paramagnetic metals may be covalently attached to the ligands, directly connected to the ligands or through a spacer. These ligands are useful as magnetic resonance imaging (MRI) probes.

In one embodiment, the PERV-B.RBD ligand of the invention, a variant and/or a fragment thereof, is labeled with a fluorescent label. Example of fluorescent label include, but are not limited to, fluorescent organic dyes, quantum dots and fluorescent protein. These ligands may be useful as optical imaging probes.

Example of fluorescent organic dyes include but are not limited to, commercial Alexa Fluor® dyes, fluorescein, rhodamine, or Cy® dyes (such as Cy3, Cy3.5, Cy5, Cy5.5, Cy7, and Cy7.5).

Example of fluorescent proteins include, but are not limited to, BFP, CFP, GFP, EGFP, mCherry, tdTomato, mPlum, mStrawberry, J-Red, DS-Red, mOrange, mCitrine, Venus, Ypet, YFP, Emerald, and the like. Another example of fluorescent protein is phycoerythrin. The fluorescent protein may be fused to the ligand by techniques of molecular cloning well known in the art.

In one embodiment, the PERV-B.RBD ligand of the invention, a variant and/or a fragment thereof, is labeled with a peptidic tag.

Example of peptidic tags include, but are not limited to, an antibody crystallizable region (Fc), Enzymes (alkaline phosphatase or horseradish peroxidase), Hemagglutinin tag, Poly Arginine tag, Poly Histidine tag, Myc tag, Strep tag, S-tag, HAT tag, 3× Flag tag, Calmodulin-Binding Peptide tag, SBP tag, Chitin Binding Domain tag, GST tag, Maltose-Binding Protein tag, Fluorescent Protein tag, T7 tag, V5 tag, X-press tag and the like. The peptidic tag may be fused to the ligands by techniques of molecular cloning well known in the art or covalently attached to the ligands.

In one embodiment, the PERV-B.RBD ligand, a variant and/or a fragment thereof, labeled as described herein is a fusion protein comprising a part or the totality of a RBD domain (as described herein), fused to a detection tag, such as, for example, a Fc fragment or a GFP. In one embodiment the PERV-B.RBD ligand of the invention, a variant and/or a fragment thereof, is fused to a Fc fragment or a fluorescent protein. In one embodiment, the PERV-B.RBD ligand, a variant and/or a fragment thereof, labeled as described herein is a fusion protein comprising a part or the totality of a RBD domain (as described herein), fused to phycoerythrin.

Examples of Fc fragments include, but are not limited to, rabbit Fc fragment (amino acid sequence SEQ ID NO: 9, encoded by SEQ ID NO: 10), mouse Fc fragment (amino acid sequence SEQ ID NO: 11, encoded by SEQ ID NO: 12).

```
                                       (SEQ ID NO: 9)
APSTCSKPTCPPPELLGGPSVFIFPPKPKDTLMISRTPEVTCVVVDVSQD

DPEVQFTWYINNEQVRTARPPLREQQFDCTIRVVSTLPIAHQDWLRGKEF

KCKVHNKALPAPIEKTISKARGQPLEPKVYTMGPPREELSSRSVSLTCMI

NGFYPSDISVEWEKNGKAEDNYKTTPAVLDSDGSYFLYSKLSVPTSEWQR

GDVFTCSVMHEALHNHYTQKSISRSPGK (SEQ ID NO: 10)
GCACCCTCGACATGCAGCAAGCCCACGTGCCCACCCCCTGAACTCCTGGG

GGGACCGTCTGTCTTCATCTTCCCCCCAAAACCCAAGGACACCCTCATGA

TCTCACGCACCCCCGAGGTCACATGCGTGGTGGTGGACGTGAGCCAGGAT

GACCCCGAGGTGCAGTTCACATGGTACATAAACAACGAGCAGGTGCGCAC

CGCCCGGCCGCCGCTACGGGAGCAGCAGTTCAACAGCACGATCCGCGTGG

TCAGCACCCTCCCCATCACGCACCAGGACTGGCTGAGGGGCAAGGAGTTC

AAGTGCAAAGTCCACAACAAGGCACTCCCGGCCCCCATCGAGAAAACCAT

CTCCAAAGCCAGAGGGCAGCCCCTGGAGCCGAAGGTCTACACCATGGGCC

CTCCCCGGGAGGAGCTGAGCAGCAGGTCGGTCAGCCTGACCTGCATGATC

AACGGCTTCTACCCTTCCGACATCTCGGTGGAGTGGGAGAAGAACGGGAA

GGCAGAGGACAACTACAAGACCACGCCGGCCGTGCTGGACAGCGACGGCT

CCTACTTCCTCTACAACAAGCTCTCAGTGCCCACGAGTGAGTGGCAGCGG

GGCGACGTCTTCACCTGCTCCGTGATGCACGAGGCCTTGCACAACCACTA

CACGCAGAAGTCCATCTCCCGCTCTCCGGGTAAATGA
```

(SEQ ID NO: 11)
VDVPRDCGCKPCICTVPEVSSVFIFPPKPKDVLTITLTPKVTCVVVDISK

DDPEVQFSWFVDDVEVHTAQTQPREEQFNSTFRSVSELPIMHQDWLNGKE

FKCRVNSAAFPAPIEKTISKTKGRPKAPQVYTIPPPREQMAKDKVSLTCM

ITDFFPEDITVEWQWNGQPAENYKNTQPIMDTDGSYFVYSKLNVQKSNWE

AGNTFTCSVLHEGLHNHHTEKSLSHSPGK (SEQ ID NO: 12)
GTCGACGTGCCCAGGGATTGTGGTTGTAAGCCTTGCATATGTACAGTCCC

AGAAGTATCATCTGTCTTCATCTTCCCCCCAAAGCCCAAGGATGTGCTCA

CCATTACTCTGACTCCTAAGGTCACGTGTGTTGTGGTAGACATCAGCAAG

GATGATCCCGAGGTCCAGTTCAGCTGGTTTGTAGATGATGTGGAGGTGCA

CACAGCTCAGACGCAACCCCGGGAGGAGCAGTTCAACAGCACTTTCCGCT

CAGTCAGTGAACTTCCCATCATGCACCAGGACTGGCTCAATGGCAAGGAG

TTCAAATGCAGGGTCAACAGTGCAGCTTTCCCTGCCCCCATCGAGAAAAC

CATCTCCAAAACCAAAGGCAGACCGAAGGCTCCACAGGTGTACACCATTC

CACCTCCCAAGGAGCAGATGGCCAAGGATAAAGTCAGTCTGACCTGCATG

ATAACAGACTTCTTCCCTGAAGACATTACTGTGGAGTGGCAGTGGAATGG

GCAGCCAGCGGAGAACTACAAGAACACTCAGCCCATCATGGACACAGATG

GCTCTTACTTCGTCTACAGCAAGCTCAATGTGCAGAAGAGCAACTGGGAG

GCAGGAAATACTTTCACCTGCTCTGTGTTACATGAGGGCCTGCACAACCA

CCATACTGAGAAGAGCCTCTCCCACTCTCCTGGTAAATGA

In one embodiment, the PERV-B.RBD ligand of the invention, is fused to a Fc fragment, and comprises or consists of the amino acid sequence SEQ ID NO: 13, a variant and/or a fragment thereof.

(SEQ ID NO: 13)
MHPTLSWRHLPTRGGEPKRLRIPLSFASIAWFLTLTITPQASSKRLIDSS

NPHRPLSLTWLIIDPDTGVTVNSTRGVAPRGTWWPELHFCLRLINPAVKS

TPPNLVRSYGFYCCPGTEKEKYCGGSEESFCRRWSCVTSNDGDWKWPISL

QDRVKFSFVNSGPGKYKVMKLYKDKSCSPSDLDYLKISFTEKGKQENIQK

WINGMSWGIVFYKYGGGAGSTLTIRLRIEAGTEPPVAVGSVDVPRDCGCK

PCICTVPEVSSVFIFPPKPKDVLTITLTPKVTCVVVDISKDDPEVQFSWF

VDDVEVHTAQTQPREEQFNSTFRSVSELPIMHQDWLNGKEFKCRVNSAAF

PAPIEKTISKTKGRPKAPQVYTIPPPKEQMAKDKVSLTCMITDFFPEDIT

VEWQWNGQPAENYKNTQPIMDTDGSYFVYSKLNVQKSNWEAGNTFTCSVL

HEGLHNHHTEKSLSHSPGK

In one embodiment, the PERV-B.RBD ligand of the invention, a variant and/or a fragment thereof, is fused to a Fc fragment and does not comprise a signal peptide. In one embodiment, the PERV-B.RBD ligand fused to a Fc fragment comprises or consists of amino acids 44 to 469 of SEQ ID NO: 13, or a variant thereof.

In one embodiment, the PERV-B.RBD ligand of the invention, a variant and/or a fragment thereof, is fused to a Fc fragment and does not comprise a signal peptide. In one embodiment, the PERV-B.RBD ligand fused to a Fc fragment comprises or consists of amino acids 39, 40, 41, 42, 43, 44, 45, 46, 47, 48 or 49 to 469 of SEQ ID NO: 13, or a variant thereof.

In one embodiment, the amino-acid sequence of the PERV-B.RBD ligand of the invention is fused to a Fc fragment and, comprises or consists of an amino acid sequence presenting a sequence identity of at least about 70%, preferably a sequence identity of at least about 75%, 80%, 85%, 90%, 91%, 92%, 93%, 94%, 95%, 96%, 97%, 98%, 99% or more, with the amino acid sequence SEQ ID NO: 13, a variant and/or a fragment thereof.

In one embodiment, PERV-B.RBD ligand of the invention, a variant and/or a fragment thereof is fused to a Fc fragment, and is encoded by a nucleic acid sequence comprising or consisting of the nucleic acid sequence SEQ ID NO: 14, a variant and/or a fragment thereof.

(SEQ ID NO: 14)
ATGCATCCCACGTTAAGCTGGCGCCACCTCCCGACTCGGGGTGGAGAGCC

GAAAAGACTGAGAATCCCCTTAAGCTTCGCCTCCATCGCCTGGTTCCTTA

CTCTAACAATAACTCCCCAGGCCAGTAGTAAACGCCTTATAGACAGCTCG

AACCCCCATAGACCTTTATCCCTTACCTGGCTGATTATTGACCCTGATAC

GGGTGTCACTGTAAATAGCACTCGAGGTGTTGCTCCTAGAGGCACCTGGT

GGCCTGAACTGCATTTCTGCCTCCGATTGATTAACCCCGCTGTTAAAAGC

ACACCTCCCAACCTAGTCCGTAGTTATGGGTTCTATTGCTGCCCAGGCAC

AGAGAAAGAGAAATACTGTGGGGGTTCTGAGGAATCCTTCTGTAGGAGAT

GGAGCTGCGTCACCTCCAACGATGGAGACTGGAAATGGCCGATCTCTCTC

CAGGACCGGGTAAAATTCTCCTTTGTCAATTCCGGCCCGGGCAAGTACAA

AGTGATGAAACTATATAAAGATAAGAGCTGCTCCCCATCAGACTTAGATT

ATCTAAAGATAAGTTTCACTGAAAAAGGAAAACAGGAAAATATTCAAAAG

TGGATAAATGGTATGAGCTGGGGAATAGTTTTTTATAAATATGGCGGGGG

AGCAGGGTCCACTTTTAACCATTCGCCTTAGGATAGAGGCGGGGACAGAAC

CCCCTGTGGCAGTGGGATCCGTCGACGTGCCCAGGGATTGTGGTTGTAAG

CCTTGCATATGTACAGTCCCAGAAGTATCATCTGTCTTCATCTTCCCCCC

AAAGCCCAAGGATGTGCTCACCATTACTCTGACTCCTAAGGTCACGTGTG

TTGTGGTAGACATCAGCAAGGATGATCCCGAGGTCCAGTTCAGCTGGTTT

GTAGATGATGTGGAGGTGCACACAGCTCAGACGCAACCCCGGGAGGAGCA

GTTCAACAGCACTTTCCGCTCAGTCAGTGAACTTCCCATCATGCACCAGG

ACTGGCTCAATGGCAAGGAGTTCAAATGCAGGGTCAACAGTGCAGCTTTC

CCTGCCCCCATCGAGAAAACCATCTCCAAAACCAAAGGCAGACCGAAGGC

TCCACAGGTGTACACCATTCCACCTCCCAAGGAGCAGATGGCCAAGGATA

AAGTCAGTCTGACCTGCATGATAACAGACTTCTTCCCTGAAGACATTACT

GTGGAGTGGCAGTGGAATGGGCAGCCAGCGGAGAACTACAAGAACACTCA

GCCCATCATGGACACAGATGGCTCTTACTTCGTCTACAGCAAGCTCAATG

TGCAGAAGAGCAACTGGGAGGCAGGAAATACTTTCACCTGCTCTGTGTTA

CATGAGGGCCTGCACAACCACCATACTGAGAAGAGCCTCTCCCACTCTCC

TGGTAAATGATCCCAGTGTCCTTGGAGCCCTCTGGTCCTACAgcggccgc

TCTAG

In one embodiment, the PERV-B.RBD ligand of the invention, a variant and/or a fragment thereof, is fused to a Fc fragment and is encoded by a nucleic acid sequence comprising or consisting of a nucleic acid sequence presenting a sequence identity of at least about 70%, preferably a sequence identity of at least about 75%, 80%, 85%, 90%, 91%, 92%, 93%, 94%, 95%, 96%, 97%, 98%, 99% or more, with the nucleic acid sequence SEQ ID NO: 14, a variant and/or a fragment thereof.

In one embodiment, the PERV-B.RBD ligand of the invention, a fragment and/or a variant thereof, is coupled with at least one detectable label. Non-limiting examples of contrast agents are listed herein. In one embodiment, the contrast agent is I-125.

In one embodiment, the PERV-B.RBD ligand of the invention, a variant and/or a fragment thereof, coupled with at least one detectable label may be used as a probe for medical imaging.

The term medical imaging as used herein refers to imaging techniques suitable to visualize in vivo a subject's internal structures (i.e. tissues or organs). Such techniques include but are not limited to, computed tomography (CT scan), endoscopic ultrasound (EUS), magnetic resonance imaging (MRI), positron-emission tomography (PET), single photon emission tomography (SPECT), magnetic resonance cholangiopancreatography, fluorimetry, fluorescence, and near-infrared (NIR) fluorescent imaging. In the context of the invention the PERV-B.RBD ligand of the invention, a variant and/or a fragment thereof, coupled with at least one detectable label may be used as a probe, to localize in vivo SMVT-expressing cells in a subject's internal structures.

In one embodiment of the invention, the at least one PERV-B.RBD ligand of the invention, a variant and/or a fragment thereof, coupled with at least one detectable label is for use as a tracer. The present invention thus further relates to the use as a tracer of a PERV-B.RBD ligand, a variant and/or a fragment thereof, coupled with at least one detectable label. The term "tracer", as used herein, refers to a recognition agent providing insight into SMVT-related disease location, progression and/or structure for pre-, intra- and post-operative surgery.

In one embodiment, the PERV-B.RBD ligand of the invention is a variant of one of the polypeptides having an amino acid sequence selected from the group comprising or consisting of SEQ ID NO: 2, 4, 5, 6, 13, 17, 18, 19, 20, 21 and 22, and fragments thereof, preferably a variant of one of the polypeptides having an amino acid sequence selected from the group comprising or consisting of SEQ ID NO: 5, 6, 13, 19, 20, 21 and 22, and fragments thereof.

In one embodiment, the PERV-B.RBD ligand of the invention is a variant of one of the polypeptides having an amino acid sequence selected from the group comprising or consisting of SEQ ID NO: 2, 4, 5, 6, 13, 17, 18, 19, 20, 21, 22, 25 and 26, and fragments thereof, preferably a variant of one of the polypeptides having an amino acid sequence selected from the group comprising or consisting of SEQ ID NO: 5, 6, 13, 19, 20, 21 and 22, and fragments thereof.

In one embodiment, a variant of a sequence selected from SEQ ID NO: 2, 4, 5, 6, 13, 17, 18, 19, 20, 21 and 22 and fragments thereof is capable of binding to SMVT with an affinity at least equivalent to the one of SEQ ID NO: 2, 4, 5, 6, 13, 17, 18, 19, 20, 21 and 22 or a fragment thereof, respectively.

In one embodiment, a variant of a sequence selected from SEQ ID NO: 2, 4, 5, 6, 13, 17, 18, 19, 20, 21, 22, 25 and 26 and fragments thereof is capable of binding to SMVT with an affinity at least equivalent to the one of SEQ ID NO: 2, 4, 5, 6, 13, 17, 18, 19, 20, 21, 22, 25 and 26 or a fragment thereof, respectively.

In one embodiment, a variant of a sequence selected from SEQ ID NO: 2, 4, 5, 6, 13, 17, 18, 19, 20, 21 and 22 and fragments thereof comprises conservative amino acid substitutions as compared to the sequence SEQ ID NO: 2, 4, 5, 6, 13, 17, 18, 19, 20, 21 or 22 or a fragment thereof, respectively, such as, for example, 1, 2, 3, 4, 5, 6, 7, 8, 9 or 10 conservative amino acid substitutions.

In one embodiment, a variant of a sequence selected from SEQ ID NO: 2, 4, 5, 6, 13, 17, 18, 19, 20, 21, 22, 25 and 26 and fragments thereof comprises conservative amino acid substitutions as compared to the sequence SEQ ID NO: 2, 4, 5, 6, 13, 17, 18, 19, 20, 21, 22, 25 or 26 or a fragment thereof, respectively, such as, for example, 1, 2, 3, 4, 5, 6, 7, 8, 9 or 10 conservative amino acid substitutions.

In another embodiment, a variant of a sequence selected from SEQ ID NO: 2, 4, 5, 6, 13, 17, 18, 19, 20, 21 and 22 and fragments thereof is a polypeptide wherein 1, 2, 3, 4, 5, 6, 7, 8, 9 or 10 amino acids from the sequence SEQ ID NO: 2, 4, 5, 6, 13, 17, 18, 19, 20, 21 or 22 or a fragment thereof respectively, is/are absent, or substituted by any amino acid, or wherein 1, 2, 3, 4, 5, 6, 7, 8, 9 or 10 amino acids (either contiguous or not) is/are added.

In another embodiment, a variant of a sequence selected from SEQ ID NO: 2, 4, 5, 6, 13, 17, 18, 19, 20, 21, 22, 25 and 26 and fragments thereof is a polypeptide wherein 1, 2, 3, 4, 5, 6, 7, 8, 9 or 10 amino acids from the sequence SEQ ID NO: 2, 4, 5, 6, 13, 17, 18, 19, 20, 21, 22, 25 or 26 or a fragment thereof respectively, is/are absent, or substituted by any amino acid, or wherein 1, 2, 3, 4, 5, 6, 7, 8, 9 or 10 amino acids (either contiguous or not) is/are added.

The PERV-B.RBD ligand of the invention, a variant and/or a fragment thereof, may be modified by means well-known in the art, for instance by the addition of one or more functional group such as a phosphate, acetate, lipid or carbohydrate group, and/or by the addition of one or more protecting group. For example, the RBD ligands can be modified by the addition of one or more functional groups such as phosphate, acetate, or various lipids and carbohydrates. The RBD ligands of the invention can also exist as polypeptide derivatives. The term "polypeptide derivative" refers to compound having an amino group (—NH—), and more particularly, a peptide bond. Polypeptides may be regarded as substituted amides. Like the amide group, the peptide bond shows a high degree of resonance stabilization. The C—N single bond in the peptide linkage has typically about 40 percent double-bond character and the C=O double bond about 40 percent single-bond character. "Protecting groups" are those groups that prevent undesirable reactions (such as proteolysis) involving unprotected functional groups. Specific examples of amino protecting groups include formyl; trifluoroacetyl; benzyloxycarbonyl; substituted benzyloxycarbonyl such as (ortho- or para-) chlorobenzyloxycarbonyl and (ortho- or para-) bromobenzyloxycarbonyl; and aliphatic oxycarbonyl such as t-butoxycarbonyl and t-amiloxycarbonyl. The carboxyl groups of amino acids can be protected through conversion into ester groups. The ester groups include benzyl esters, substituted benzyl esters such as methoxybenzyl ester; alkyl esters such as cyclohexyl ester, cycloheptyl ester or t-butyl ester. The guanidino moiety may be protected by nitro; or arylsulfonyl such as tosyl, methoxybenzensulfonyl or mesitylenesulfonyl, even though it does not need a protecting group. The protecting groups of imidazole include tosyl, benzyl and dinitrophenyl. The indole group of tryptophan may be protected by formyl or may not be protected.

The modification of the RBD ligands may aim at improving their lifetime in vivo. One type of modification is the addition to the N- or C-termini of the RBD ligands of polyethylene glycol (PEG). PEG is known by the person skilled in the art to have many properties that make it an ideal carrier for polypeptides such as high water-solubility, high mobility in solution and low immunogenicity. This modification also protects the polypeptides from exopeptidases and therefore increases their overall stability in vivo. Other modifications used to prevent degradation of the polypeptides by endopeptidases or exopeptidases include N-terminal modifications such as acetylation or glycosylation, C-terminal modifications such as amidation and use of unnatural amino acids (β-amino and α-trifluoromethyl amino acids) at particular sites within the polypeptides. Another alternative to increase polypeptide molecular size is the genetic fusion of the polypeptides to the Fc domain of human immunoglobulin (including, for example, IgA, IgM and IgG) or the fusion of the polypeptides to albumin.

In one embodiment, the PERV-B.RBD ligand of the invention, a variant and/or a fragment thereof, is glycosylated. In another embodiment, the PERV-B.RBD ligand of the invention, a variant and/or a fragment thereof is not glycosylated.

The RBD ligands of the invention described herein can be produced synthetically by chemical synthesis or enzymatic synthesis as it is well known in the art. Alternatively, nucleotide sequences encoding the polypeptides of the invention can be introduced into a protein expression vector and produced in a suitable host organism (e.g., bacteria, insect cells, etc.), then purified. In one embodiment, the receptor-binding domain ligand is obtained by a cloning method, such as, for example, using any production system known in the art, such as, for example, a bacterial cell (such as, for example, *E. coli*), yeast, baculovirus-insect cell, or mammalian cells such as HEK or CHO, expression system.

Methods for coupling at least one detectable label to an RBD ligand are well known in the state of the art. For instance, the at least one detectable label may be bound covalently or non-covalently.

Techniques to couple polypeptides to I-125 are well known in the state of the art. A non-limited example of such a method is the following: iodine present in a reduced form (NaI) reacts with the phenol group of a tyrosine or with the side chain of a histidine residue. These groups are pre-oxidized with an oxidizing agent (iodogen). The peptides preparation (100 μg for 1 mci=37 MBq) is then added to an iodogen solution and incubated for 10 minutes at 4° C. The reaction is stopped using a stop solution comprising for example 200 μL of PBS with sodium azide per marking. In parallel, a mouse serum is added onto a PD10 column. Then the reaction solution is added onto the PD10 column and the peptide coupled with the iodine is collected.

In embodiments concerning detectable labels encoded by a nucleic acid sequence, the detectable label may be fused to the RBD ligand of the invention, a variant and/or a fragment thereof, by techniques of molecular cloning well known in the art.

In one embodiment, the PERV-B.RBD ligand of the invention, a variant and/or a fragment thereof, binds to SMVT.

In one embodiment, the PERV-B.RBD ligand of the invention, a variant and/or a fragment thereof, binds specifically to SMVT.

The expression "specifically binds to", as used herein, refers to the binding specificity and affinity of a molecule or a domain thereof for a particular target or epitope, or a domain thereof, even in the presence of a heterogeneous population of other proteins and biological molecules. Thus, in one embodiment, under designated assay conditions, the ligand described in the invention binds preferentially to its target and does not bind in a significant amount to other components present in a test sample or subject. In one embodiment, such a ligand shows high affinity binding to its target with an equilibrium dissociation constant equal or below $1\times10^{-6}$ M (e.g., at least $0.5\times10^{-6}$, $1\times10^{-7}$, $1\times10^{-8}$, $1\times10^{-9}$, $1\times10^{-10}$ and less). Standard assays to evaluate the binding ability of two biological molecules are known in the art, including for example, ELISAs, Western blots, RIAs and flow cytometry. The binding kinetics (e.g., binding affinity) of the molecules also can be assessed by standard assays known in the art, such as by Biacore analysis.

The methods of the invention comprise the step of detecting and/or measuring the binding of a PERV-B.RBD ligand of the invention, a variant and/or a fragment thereof, to SMVT in a biological sample.

Techniques to measure the binding of a ligand to its receptor are known in the art and may imply the detection and measure of the amount of the ligand-receptor complexes. In the context of the present invention, such techniques could for example rely on the detection and measure of the amount of complexes formed by PERV-B.RBD ligands, variants and/or fragments thereof with SMVT present in the biological sample, such as, for example, at the cell surface of cells present in the biological sample Example of such technique include, but are not limited to, flow cytometry analysis, immunohistochemistry, western blot associated or not with cell fractionation, enzyme-linked immunosorbent assay (ELISA), sandwich ELISA, fluorescent-linked immunosorbent assay (FLISA), enzyme immunoassay (EIA), radioimmunoassay (RIA), image analysis, for example high content analysis, computed tomography (CT scan), endoscopic ultrasound (EUS), magnetic resonance imaging (MRI), positron-emission tomography (PET), single photon emission tomography (SPECT), magnetic resonance cholangiopancreatography, fluorimetry, fluorescence, and near-infrared (NIR) fluorescent imaging and the like.

Examples of such techniques amenable to an in vitro use include, but are not limited to, immunohistochemistry, Multiplex methods (Luminex), western blot, enzyme-linked immunosorbent assay (ELISA), sandwich ELISA, fluorescent-linked immunosorbent assay (FLISA), enzyme immunoassay (EIA), radioimmunoassay (RIA), flow cytometry (FACS), and the like.

Examples of such techniques suitable for an in vivo use include, but are not limited to, computed tomography (CT scan), endoscopic ultrasound (EUS), magnetic resonance imaging (MRI), positron-emission tomography (PET), single photon emission tomography (SPECT), magnetic resonance cholangiopancreatography, fluorimetry, fluorescence, and near-infrared (NIR) fluorescent imaging.

In one embodiment, the methods of the invention further comprise a step of comparing the binding of the PERV-B.RBD ligand of the invention, a variant and/or a fragment thereof, to SMVT measured at step b. with a reference value.

As used herein, the term "reference" broadly encompasses any suitable reference binding level which may be used as a basis for comparison with respect to the determined binding. In one embodiment, the reference is constructed using algorithms and/or other methods of statistical and hierarchical classification. In another aspect, the reference binding level is stored in a database to provide a stored binding level and the stored binding level is used to determine the difference in the binding level. The database may, for example, be stored on a computer or a server.

In one embodiment, the reference binding level is an index value or is derived from one or more risk prediction algorithms or computed indices for the presence of cells wherein the function and/or expression of SMVT is altered (e.g., increased or decreased). A reference binding level can be relative to a number or value derived from population studies, including without limitation, such populations of subjects having similar age range, subjects in the same or similar ethnic group.

In one embodiment, the reference value is determined by measuring the binding of the PERV-B.RBD ligand of the invention, a fragment and/or a variant thereof, to SMVT in a reference population.

In one embodiment, the reference population refers to a population comprising at least 1, preferably at least 5, at least 10, at least 15, at least 20, at least 25, at least 30, at least 35, at least 40, at least 45, at least 50, at least 75, at least 100 or more substantially healthy subjects, i.e., subject who are not affected and/or who have not been diagnosed with the SMVT-related disease being considered. According to this embodiment, a determined binding level different from the reference binding level may be indicative of the presence of a SMVT related disease.

In another embodiment, the reference population refers to a population comprising at least 1, preferably at least 5, at least 10, at least 15, at least 20, at least 25, at least 30, at least 35, at least 40, at least 45, at least 50, at least 75, at least 100 or more subjects affected (and preferably diagnosed) with the SMVT-related disease being considered. According to this embodiment, a determined binding level different from the reference binding level may be indicative of the absence of a SMVT related disease.

In the present invention, two numeric values, in particular two binding levels, are considered as different if the first numeric value is higher (such as, for example, the first numeric value is about 20% higher than the second one, preferably is about 30, 40, 50, 60, 70, 80, 90% or more higher than the second one) or lower than the second one (such as, for example, the second numeric value is about 20% lower than the second one, preferably is about 30, 40, 50, 60, 70, 80, 90% or more lower than the second one).

In one embodiment, two numeric values, in particular two binding levels, are considered as different if the first numeric value is increased by a factor of or above about 1.01, preferably by a factor of or above, about 1.02, 1.03, 1.04, 1.05, 1.06, 1.07, 1.08, 1.09, more preferably the value is increased by a factor of or above about 1.1, 1.15, 1.20, 1.25, 1.30, 1.3, 1.35, 1.40, 1.45, 1.50, 1.55, 1.60, 1.65, 1.70, 1.75, 1.80, 1.85, 1.90, 1.95, more preferably by a factor of or above about 2, 3, 4, 5 or more when compared to the second value or if the first numeric value is decreased by a factor of or below about 0.99, preferably by a factor of or below, about 0.98, 0.97, 0.96, 0.95, 0.94, 0.93, 0.92, 0.91, more preferably the value is decreased by a factor of or below about 0.90, 0.85, 0.80, 0.75, 0.70, 0.65, 0.60, 0.55, 0.50, 0.45, 0.40, 0.35, 0.30, 0.25, 0.20, 0.15, 0.1 or less when compared to the second value.

In one embodiment, by implying a multitude of measures of the binding of the PERV-B.RBD ligand of the invention to SMVT in the reference population, it is conceivable to use as reference value a mathematical representation of the binding of the PERV-B.RBD ligand of the invention to SMVT such as for example, a mean or a median.

In one embodiment, the reference value is a personalized reference, determined at different time points in the same subject (such as, for example, before receiving a treatment for a SMVT-related disease).

In one embodiment, the reference value is an internal reference value, determined in different part of the same subject, such as, for example, in different organs or tissues. This type of reference value is in particular useful in the implementation of method based on medical imaging.

In one embodiment, the in vitro method of the present invention is for diagnosing a SMVT-related disease in a subject, or for identifying a subject as presenting a risk of developing an SMVT-related disease.

The present invention thus also relates to in vitro methods for diagnosing a SMVT-related disease in a subject, or for identifying a subject as presenting a risk of developing an SMVT-related disease, wherein said methods comprises the steps of:
 a. contacting a biological sample from the subject with at least one PERV-B.RBD ligand, a variant and/or a fragment thereof; and,
 b. measuring the binding of said PERV-B.RBD ligand, variant and/or fragment thereof to SMVT.

The present invention relates to an in vitro method for diagnosing a subject with or identifying a subject as being at risk of developing a SMVT-related disease comprising the steps of:
 a. contacting a biological sample previously obtained from said subject with a PERV-B.RBD ligand, a variant and/or a fragment thereof;
 b. measuring the binding of said PERV-B.RBD ligand, variant and/or fragment thereof to SMVT; and,
 c. comparing the binding measured at step b. with a reference value.

In one embodiment, the step of comparing the binding of the PERV-B.RBD ligand of the invention, a variant and/or a fragment thereof, to a reference value allows to diagnose a subject with, or at risk of developing, a SMVT-related disease.

In one embodiment, the SMVT-related disease is cancer, a disorder of pregnancy, an infectious disease or a neurodegenerative disease.

In one embodiment, the SMVT-related disease is cancer, a disorder of pregnancy, an infectious disease or a neuroinflammatory disease.

In one embodiment, the SMVT-related disease is a disorder related to a mutation within the SLC5A6 gene.

In one embodiment, the SMVT-related disease is cancer, preferably cancer selected from the group comprising or consisting of liver cancer, prostate cancer, lung cancer, gallbladder cancer, pancreas cancer, colon cancer, ovarian cancer, brain cancer, kidney cancer, thyroid cancer, lymphomas, urothelial cancer, cervical cancer and endometrial cancer.

In one embodiment, the SMVT-related disease is cancer, preferably cancer selected from the group comprising or consisting of liver cancer, prostate cancer, lung cancer, gallbladder cancer, pancreas cancer, colon cancer, ovarian cancer, brain cancer, kidney cancer, thyroid cancer, and lymphomas.

Examples of liver cancers include, but are not limited to, hepatoma, hepatocellular carcinoma, cholangiocarcinoma, hepatoblastoma, angiosarcoma, hepatocellular adenoma, and hemangioma.

In one embodiment, said liver cancer is a hepatocellular carcinoma or a cholangiocarcinoma.

In one embodiment, said liver cancer is a hepatocellular carcinoma.

Examples of prostate cancers include, but are not limited to, adenocarcinoma, and sarcoma.

Examples of lung cancers include, but are not limited to non-small cell lung carcinoma, adenocarninoma, bronchogenic carcinoma, alveolar carcinoma, bronchiolar carcinoma, bronchial adenoma, lung sarcoma, lymphoma, chondromatous hamartoma, and pleural mesothelioma.

In one embodiment, said lung cancer is a non-small cell lung carcinoma.

Examples of pancreas cancers include, but are not limited to, ductal adenocarcinoma, insulinoma, glucagonoma, gastrinoma, carcinoid tumors, and vipoma.

Examples of colon cancers include, but are not limited to large bowel or large intestines cancer (such as, e.g., adenocarcinoma, tubular adenoma, villous adenoma, hamartoma or leiomyoma), and colorectal cancer.

Examples of ovarian cancers include, but are not limited to, dysgerminoma, granulosa-theca cell tumors, and Sertoli-Leydig cell tumors.

Examples of brain cancers include, but are not limited to, astrocytoma, medulloblastoma, glioma, lower grade glioma, ependymoma, germinoma (pinealoma), glioblastoma multiform, oligodendroglioma, schwannoma, retinoblastoma, congenital tumors, spinal cord neurofibroma, glioma, and sarcoma.

Example of kidney cancer include, but are not limited to, clear renal cell carcinoma, chromophobe renal cell carcinoma, papillary renal cell carcinoma, adenocarcinoma, Wilm's tumor, and nephroblastoma.

Other examples of cancer include, but are not limited to, lymphoma and leukemia.

Example of thyroid cancers include, but are not limited to, anaplastic thyroid carcinomas.

Examples of lymphomas include, but are not limited to, Hodgkin lymphoma, and non-Hogdkin lymphomas.

In one embodiment, the SMVT-related disease is prostate cancer.

In one embodiment, the SMVT-related disease is a neurodegenerative disease, such as, for example, multiple sclerosis or Huntington's disease.

In one embodiment, the SMVT-related disease is a neuroinflammatory disease, preferably multiple sclerosis.

In one embodiment, the SMVT-related disease is a disorder of pregnancy, preferably pre-eclampsia, or intrauterine growth retardation.

In one embodiment, the SMVT-related disease is a disorder associated with anomalies of placental and/or fetal development, such as, for example, intrauterine growth retardation.

In one embodiment, the SMVT-related disease is a disorder related to a mutation within the SLC5A6 gene. In one embodiment, said mutation within the SLC5A6 results in a partial or complete loss of function or partial or complete loss of expression.

In one embodiment, the SMVT-related disease is a disorder related to a mutation within the SLC5A6 gene, such as, for example the mutation described by Subramanian et al (Hum Genet. 2017, February; 136(2): 253-261), which is associated with failure to thrive, microcephaly and brain changes on MRI, cerebral palsy and developmental delay, variable immunodeficiency, severe gastro-esophageal reflux requiring a gastrostomy tube/fundoplication, osteoporosis and pathologic bone fractures. Another example of a mutation within the SLC5A6 gene is the mutation described by Schwantje et al. (JIMD Rep. 2019 May 28; 48(1):11-14), leading to biotin deficiency, symptoms and metabolites levels similar to those observed in cases of biotinidase deficiency.

In one embodiment, the SMVT-related disease is an infectious disease,

As defined hereinabove, "infectious disease" as used herein encompasses any disease caused by an infectious agent such as a virus, a bacterium, a fungus, a protozoan parasite or a prion protein.

In one embodiment, said infectious disease is caused by a virus. In other words, in one embodiment, said infectious disease is a viral infection.

Examples of viruses that may be responsible for a viral infection include, without being limited to, viruses of the families Arenaviridae, Astroviridae, Birnaviridae, Bromoviridae, Bunyaviridae, Caliciviridae, Closteroviridae, Comoviridae, Cystoviridae, Flaviviridae, Flexiviridae, Hepadnaviridae, Hepevirus, Herpesviridae, Leviviridae, Luteoviridae, Mononegavirales, Mosaic Viruses, Nidovirales, Nodaviridae, Orthomyxoviridae, Paramyxoviridae, Papillomaviridae, Picobirnavirus, Picornaviridae, Potyviridae, Reoviridae, Retroviridae, Sequiviridae, Tenuivirus, Togaviridae, Tombusviridae, Totiviridae, and Tymoviridae.

In one embodiment, said infectious disease is caused by a bacterium, preferably belonging to the order Enterobacteriales.

In one embodiment, said infectious disease is caused by a bacterium, preferably belonging to the genus *Salmonella*. In other words, in one embodiment, said infectious disease is a *Salmonella* infection.

Examples of bacteria that may be responsible for a bacterial infection include, without being limited to, bacteria of the genera *Bacillus*, including *Bacillus anthracis* and *Lactobacillus; Brucella; Bordetella* including *B. pertussis* and *B. bronchiseptica; Camplyobacter; Chlamydia* including *C. psittaci* and *C. trachomatis; Samonella* including *S. bongori* and *S. enterica Corynebacterium* including *C. diphtheriae; Enterobacter* including *E. aerogenes; Enterococcus; Escherichia* including *E. coli; Flavobacterium* including *F. meningosepticum* and *F. odoraturn; Gardnerella* including *G. vaginalis; Klebsiella; Legionella* including *L. pneumophila; Listeria; Mycobacterium* including *M. tuberculosis, M. intracellulare, M. folluitum, M. laprae, M avium, M bovis, M. africanum, M. kansasii*, and *M. lepraernurium; Neisseria* including *N. gonorrhoeae* and *N. meningitides; Nocardia; Proteus* including *P. mirabilis* and *P. vulgaris; Pseudomonas* including *P. aeruginosa; Rickettsia* including *R. rickettsii; Serratia* including *S. marcescens* and *S. liquefaciens; Staphylococcus; Streptomyces* including *S. somaliensis; Streptococcus*, including *S. pyogenes*; and *Treponema*.

In one embodiment, said infectious disease is caused by a fungus. In other words, in one embodiment, said infectious disease is a fungal infection.

Examples of fungi that may be responsible for a fungal infection include, without being limited to, fungi of the genera *Aspergillus, Candida, Cryptococcus, Epidermophyton, Microsporum*, and *Trichophyton*.

In one embodiment, said infectious disease is caused by a protozoan parasite. In other words, in one embodiment, said infectious disease is a protozoan infection.

Examples of protozoan parasites that may be responsible for a protozoan infection include, without being limited to, *Coccidia, Leishmania, Plasmodium, Toxoplasma* and *Trypanosoma*.

In one embodiment, the method of the invention is for diagnosing or for assessing a risk of developing a SMVT-related disease associated with an increased SMVT level in a subject, and a binding of the PERV-B.RBD ligand, variant and/or fragment thereof to SMVT measured at step b. higher than the binding of the PERV-B.RBD ligand of the invention, variant and/or fragment thereof to SMVT measured in a reference population of substantially healthy subjects (or in a reference sample from a reference population) is indicative of the presence of said disease, or of a risk of developing said disease.

In one embodiment, the method of the invention is for diagnosing or for assessing a risk of developing a SMVT-related disease associated with an increased SMVT level at the cell surface in a subject, and a binding of the PERV-B.RBD ligand, variant and/or fragment thereof to SMVT measured at step b. higher than the binding of the PERV-B.RBD ligand of the invention, variant and/or fragment thereof to SMVT measured in a reference population of substantially healthy subjects (or in a reference sample from a reference population) is indicative of the presence of said disease, or of a risk of developing said disease.

Examples of SMVT-related diseases associated with an increased SMVT expression level and/or level of SMVT at the cell surface include, but are not limited to, lung cancer, liver cancer, prostate cancer, kidney cancer, thyroid cancer, pancreas cancer, colon cancer (in particular colorectal cancer), gallbladder cancer, urothelial cancer, cervical cancer and endometrial cancer.

In one embodiment, the method of the invention is for diagnosing or for assessing a risk of developing a SMVT-related disease associated with a decreased SMVT level in a subject, and a binding of the PERV-B.RBD ligand, variant and/or fragment to SMVT measured at step b. lower than the binding of the PERV-B.RBD ligand, variant and/or fragment to SMVT measured in a reference population of substantially healthy subjects (or in a reference sample from a reference population) is indicative of the presence or of a risk of developing said disease.

In one embodiment, the method of the invention is for diagnosing or for assessing a risk of developing a SMVT-related disease associated with a decreased SMVT level at the cell surface in a subject, and a binding of the PERV-B.RBD ligand, variant and/or fragment to SMVT measured at step b. lower than the binding of the PERV-B.RBD ligand, variant and/or fragment to SMVT measured in a reference population of substantially healthy subjects (or in a reference sample from a reference population) is indicative of the presence or of a risk of developing said disease.

Examples of SMVT-related diseases associated with a decreased SMVT expression level and/or SMVT level at the cell surface include, but are not limited to, lymphomas, ovarian cancer, and disorders of pregnancy.

The present invention also relates to in vivo methods for detecting and/or measuring the level of SMVT using a PERV-B.RBD ligand of the invention, a variant and/or fragment thereof.

In one embodiment, said in vivo method is for diagnosing a subject with or identifying a subject as being at risk of developing a SMVT-related disease.

The present invention thus relates to a PERV-B.RBD ligand as described herein, a variant and/or fragment thereof, for use in a in vivo diagnosis method of an SMVT-related disease in a subject. In one embodiment, said method comprises the detection and/or measure of the level of SMVT within the body of said subject, such as, for example, in a specific organ or tissue.

The present invention also relates to a PERV-B.RBD ligand of the invention, a variant and/or fragment thereof, for use in a in vivo diagnosis method of cancer in a subject, wherein said method comprise the detection and/or measure of the level of SMVT in the body of said subject, such as, for example, in a specific organ.

The present application also relates to a method for the in vivo diagnosis of a SMVT-related disease, comprising:
a. contacting at least one PERV-B.RBD ligand, a variant and/or a fragment thereof with a cell, a sample, a tissue or an organ, and
b. detecting and/or quantifying the at least one PERV-B.RBD ligand bound to SMVT present in the cell, sample, tissue or organ within said subject.

The present application also relates to a method for the in vivo diagnosis of SMVT-related disease comprising:
a. administering to a subject in need thereof at least one PERV-B.RBD ligand, a variant and/or a fragment thereof, and
b. detecting and/or quantifying the binding of at least one PERV-B.RBD ligand, variant and/or fragment thereof within said subject, for example by medical imaging.

In one embodiment, of the invention, the PERV-B.RBD ligand is coupled with at least one detectable label, and may be used for in vivo diagnosis by medical imaging.

In one embodiment, the PERV-B.RBD ligand administered to the subject is comprised in a diagnostic composition.

The present invention also relates to a PERV-B.RBD ligand of the invention, a variant and/or fragment thereof, for use in a in vivo diagnosis method of an SMVT-related disease in a subject, wherein said method comprise the detection and/or measure of the level of SMVT using medical imaging techniques.

Examples of specific medical imaging techniques that may be used are well known to the skilled artisan and include, but are not limited to, computer assisted tomography (CAT), magnetic resonance spectroscopy (MRS), magnetic resonance imaging (MRI), positron emission tomography (PET) or single-photon emission computed tomography (SPECT) and are described in Boonstra et al. (2015. Oncotarget. 6(16):14260-73).

The present invention thus relates to an in vivo method for diagnosing a subject with or identifying a subject at risk of developing an SMVT-related disease comprising the steps:
a. administering to said subject a labeled PERV-B.RBD ligand, a variant and/or a fragment thereof; and,
b. detecting and/or measuring the binding of said labeled PERV-B.RBD ligand, variant and/or fragment thereof to SMVT using medical imaging;
c. optionally comparing a binding measured at step b, with a reference value.

The present invention also relates to a diagnostic composition comprising or consisting essentially of or consisting of at least one PERV-B.RBD ligand, a variant and/or a fragment thereof, and at least one pharmaceutically acceptable excipient.

As used herein, the term "consisting essentially of", with reference to a composition, means that the at least one PERV-B.RBD ligand of the invention is the only one diagnostic agent, therapeutic agent or agent with a biologic activity within said composition.

The present invention also relates to a diagnostic composition comprising or consisting essentially of at least one labeled PERV-B.RBD ligand, variant and/or fragment thereof, and at least one pharmaceutically acceptable excipient.

As used herein, the term "pharmaceutically acceptable" refers to molecular entities and compositions that do not produce an adverse, allergic or other untoward reaction when administered to a subject, especially a human, as appropriate. Hence, "Pharmaceutically acceptable excipient" refers to molecular entities and compositions that do not produce an adverse, allergic or other untoward reaction when administered to a subject, especially a human, as appropriate. It includes any and all solvents, dispersion media, coatings, antibacterial and antifungal agents, isotonic and absorption delaying agents and the like. For human administration, preparations should meet, pyrogenicity, sterility, general safety and purity standards as required by regulatory offices, such as, for example, FDA Office or EMA. A pharmaceutically acceptable carrier or excipient may thus refer to a non-toxic solid, semi-solid or liquid filler, diluent, encapsulating material or formulation auxiliary of any type.

Pharmaceutically acceptable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, such as, for example, BHA, BHT, citric acid, ascorbic acid, tetracycline, and the like.

Other examples of pharmaceutically acceptable excipients that may be used in the composition of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In addition, pharmaceutically acceptable excipients may comprise some excipients, such as, for example, surfactants (e.g. hydroxypropylcellulose); suitable carriers, such as, for example, solvents and dispersion media containing, for example, water, ethanol, polyol (e.g. glycerol, propylene glycol, and liquid polyethylene glycol, and the like), suitable mixtures thereof, and vegetable oils, such as, for example, peanut oil and sesame oil; isotonic agents, such as, for example, sugars or sodium chloride; coating agents, such as, for example, lecithin; agents delaying absorption, such as, for example, aluminum monostearate and gelatin; preservatives, such as, for example, benzalkonium chloride, benzethonium chloride, chlorobutanol, thimerosal and the like; buffers, such as, for example, boric acid, sodium and potassium bicarbonate, sodium and potassium borates, sodium and potassium carbonate, sodium acetate, sodium biphosphate and the like; tonicity agents, such as, for example, dextrose, potassium chloride, propylene glycol, sodium chloride; antioxidants and stabilizers, such as, for example, sodium bisulfite, sodium metabisulfite, sodium thiosulfite, thiourea and the like; nonionic wetting or clarifying agents, such as, for example, polysorbate 80, polysorbate 20, poloxamer 282 and tyloxapol; viscosity modifying agents, such as, for example dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose; and the like.

In one embodiment, the diagnostic composition of the invention is for diagnosing a SMVT-related disease, using a method of the invention as described hereinabove.

In one embodiment, the PERV-B.RBD ligand of the invention, variant and/or fragment thereof, is encapsulated.

The techniques of encapsulation are well known in the state of the art. Examples of capsule include, but are not limited to, phospholipids, polymers and liposomes In one embodiment, the PERV-B.RBD ligand of the invention, variant and/or fragment thereof, is encapsulated with a detectable label.

In one embodiment, the in vitro method of the present invention is for assessing the severity of a SMVT-related disease in a subject, or prognosing a SMVT-related disease.

The present invention also relates to a composition comprising or consisting essentially of or consisting of at least one PERV-B.RBD ligand according to the invention, a variant and/or a fragment thereof.

The present invention also relates to a pharmaceutical composition comprising or consisting essentially of or consisting of at least one PERV-B.RBD ligand according to the invention, a variant and/or a fragment thereof, and at least one pharmaceutically acceptable excipient.

The present invention also relates to a medicament comprising or consisting essentially of or consisting of at least one PERV-B.RBD ligand according to the invention, a variant and/or a fragment thereof.

The present invention also relates to the PERV-B.RBD ligands, variants and or fragments thereof, the pharmaceutical composition or the medicament according to the invention for use in the treatment of an SMVT-related disease.

The present invention also relates to a method for treating an SMVT-related disease, comprising administering to a subject at least one PERV-B.RBD ligand of the invention, a variant and/or a fragment thereof, the pharmaceutical composition or the medicament according to the invention.

In one embodiment, a therapeutically effective amount of the PERV-B.RBD ligand of the invention, a variant and/or a fragment thereof, is administered to the subject.

In one embodiment, the administration of a PERV-B.RBD ligand, a variant and/or a fragment thereof, modulates the flux of vitamins through the SMVT receptor.

In one embodiment, the administration of a PERV-B.RBD ligand, a variant and/or a fragment thereof, modulates the flux of biotin, pantothenic acid and/or lipoic acid through the SMVT receptor.

The present application also relates to a method for targeting cells, samples, tissues, and/or organs expressing SMVT, wherein said method comprises the administration of a PERV-B.RBD ligand of the invention, a variant and/or a fragment thereof. Such method may be used, for example, for targeting therapeutic agents to cells, samples, tissues, and/or organs in a subject in need thereof. In one embodiment, the targeting method of the invention is for targeting anticancer drugs to cancer cells, in particular to SMVT-expressing cancer cells as described herein.

In one embodiment, the PERV-B.RBD ligand of the invention, a variant and/or a fragment thereof, is encapsulated with a therapeutic agent to be specifically administered to cells, samples, tissues or organs of a subject in need thereof.

Another object of the present invention is a screening method to identify compounds modulating the level of SMVT, said method comprising the detection and/or measure of the level of SMVT in a biological sample using the in vitro or in vivo methods of the invention.

Hence, the present invention further relates to a screening method to identify compounds modulating the level of SMVT, using a PERV-B.RBD ligand of the invention, a variant and/or a fragment thereof comprising the steps of:
a. measuring the level of SMVT in a biological sample from a subject using an in vitro method of the invention;
b. contacting said sample with the tested compound;
c. measuring the level of SMVT in said sample using an in vitro method of the invention; and,
d. comparing the levels of SMVT measured at step a. and c.

The present invention also relates to a screening method to identify compounds modulating the level of SMVT using a PERV-B.RBD ligand of the invention, a variant and/or a fragment thereof comprising the steps of:
a. measuring the level of SMVT in a subject using an in vivo method of the invention;
b. contacting said subject with said compound;
c. measuring the level of SMVT in a subject using an in vivo method of the invention; and,
d. comparing the levels of SMVT measured at step a. and c.

In one embodiment, the methods of the invention further comprise a step of measuring the surface level of at least one other cell surface receptor using an RBD ligand that binds specifically to said at least one other surface receptor.

Example of cell surface receptor-RBD ligands combinations that can be considered for their use with the RBD ligand of the invention include, without limitation, those disclosed in international patent applications WO2010079208 and WO2015110606, GLUT1-human T-cell leukemia virus (HLTV) RBDs (see e.g. international patent application WO2004096841), CAT1-bovine leukemia virus (BLV) RBDs (see e.g. international patent application WO2017085271), PAR1/RFT3 and PAR2/RFT1 receptor-PERV-A RBD (see e.g. international patent application WO2012035166).

In one embodiment, the PERV-B.RBD ligand, a variant and/or a fragment thereof, the composition, the pharmaceutical composition, the medicament or the diagnostic composition of the invention is to be administered at a dose determined by the skilled artisan and personally adapted to each subject.

It will be understood that the usage of the PERV-B.RBD ligand, a variant and/or fragment thereof, the composition, the pharmaceutical composition, the medicament or the diagnostic composition of the invention will be decided by the attending physician within the scope of sound medical judgment. The specific effective amount for any particular patient will depend upon a variety of factors including the specific composition employed, the age, body weight, general health, sex and diet of the subject; the time of administration, route of administration, and like factors well known in the medical arts.

In one embodiment, the PERV-B.RBD ligand, a variant and/or a fragment thereof, the composition, the pharmaceutical composition, the medicament or the diagnostic composition of the invention is to be administered by injection, orally, topically, nasally, buccally, rectally, vaginally, intratracheally, by endoscopy, transmucosally, or by percutaneous administration.

In one embodiment, the PERV-B.RBD ligand, a variant and/or a fragment thereof, the composition, the pharmaceutical composition, the medicament or the diagnostic composition of the invention is to be administered by injection, preferably is to be systemically injected. Examples of formulations adapted to systemic injections include, but are not limited to, liquid solutions or suspensions, solid forms suitable for solution in, or suspension in, liquid prior to injection. Examples of systemic injections include, but are not limited to, intravenous, subcutaneous, intramuscular, intradermal, intravitreal, and intraperitoneal injection, or perfusion. In another embodiment, when injected, the PERV-B.RBD ligand, a variant and/or a fragment thereof, the composition, the pharmaceutical composition, the medicament or the diagnostic composition of the invention is sterile. Methods for obtaining a sterile PERV-B.RBD ligand, a variant and/or a fragment thereof, or the diagnostic composition, include, but are not limited to, GMP synthesis (GMP stands for "Good manufacturing practice").

In one embodiment, the PERV-B.RBD ligand, a variant and/or a fragment thereof, the composition, the pharmaceutical composition, the medicament or the diagnostic composition of the invention is to be orally administered. Examples of formulations adapted to oral administration include, but are not limited to, solid forms, liquid forms and gels. Examples of solid forms adapted to oral administration include, but are not limited to, pill, tablet, capsule, soft gelatine capsule, hard gelatine capsule, caplet, compressed tablet, cachet, wafer, sugar-coated pill, sugar coated tablet, or dispersing/or disintegrating tablet, powder, solid forms suitable for solution in, or suspension in, liquid prior to oral administration and effervescent tablet. Examples of liquid forms adapted to oral administration include, but are not limited to, solutions, suspensions, drinkable solutions, elixirs, sealed phial, potion, drench, syrup and liquor.

In another embodiment, the PERV-B.RBD ligand, a variant and/or a fragment thereof, the composition, the pharmaceutical composition, the medicament or the diagnostic composition of the invention is to be topically administered. Examples of formulations adapted to topical administration include, but are not limited to, sticks, waxes, creams, lotions, ointments, balms, gels, masks, leave-on washes and/or the like.

Depending on the cell(s), sample(s), tissue(s) and/or organ(s) targeted, the skilled artisan can determine the technology needed for the introduction of the PERV-B.RBD ligand, a variant and/or fragment thereof, the composition, the pharmaceutical composition, the medicament or the diagnostic composition of the invention in the targeted cell(s), sample(s), tissue(s) and/or organ(s).

In one embodiment, the PERV-B.RBD ligand, a variant and/or a fragment thereof, the composition, the pharmaceutical composition, the medicament or the diagnostic composition of the invention is to be administered in a sustained-release form. In another embodiment, the PERV-B.RBD ligand, a variant and/or a fragment thereof, the composition, the pharmaceutical composition, the medicament or the diagnostic composition of the invention comprises a delivery system that controls the release of the agent.

In one embodiment, the sample is a biological sample.

Examples of biological samples include, but are not limited to, body fluids, cell samples, tissue samples, biopsy samples.

In one embodiment, the biological sample is a body fluid. Examples of body fluids include, but are not limited to, blood, plasma, serum, lymph, ascetic fluid, cystic fluid, urine, bile, synovial fluid, bronchoalveolar lavage fluid, sputum, amniotic fluid, peritoneal fluid, cerebrospinal fluid, pleural fluid, pericardial fluid, semen, saliva, sweat and milk.

In one embodiment the biological sample is a tissue sample. Examples of tissues include, but are not limited to, placenta, intestine, brain, liver, lung, kidney, cornea, retina, heart breast, cervix, kidney, pancreas, ovary, skin, nerve, spleen, thymus, esophagus, stomach, testis, hair, skin, bone, uterus, bladder and spinal cord.

In one embodiment, the biological sample is a biopsy sample. In one embodiment, the biological sample is a fine-needle aspirate sample. In one embodiment, the biological sample is a resection sample.

In one embodiment, the biological sample is a cell sample. Examples of cell samples include, without being limited to, red blood cells, peripheral blood mononuclear cells (PBMC), peripheral white blood cells, cell samples obtained from tissue biopsies such as lymph nodes biopsies, intestinal or synovial biopsies, or cell sample obtained from broncho-alveolar lavage or cerebrospinal fluid, cell culture sample.

In one embodiment, the methods according to the present invention comprise a step of providing a biological sample from a subject.

In one embodiment, the sample was previously taken from the subject, i.e., the in vitro methods of the invention do not comprise a step of recovering a sample from the subject. Consequently, according to this embodiment, the in vitro methods of the invention are non-invasive methods.

It will be understood that the in vivo methods of the invention will be implemented by the attending physician within the scope of sound medical judgment. The specific implementation of the in vivo methods of the invention for any particular subject will depend upon a variety of factors including the condition being considered, the predisposition the said condition, the age, body weight, general health, sex and diet of the subject; and like factors well known in the medical arts.

Another object of the present invention is a kit for implementing the methods of the invention, wherein said kit comprises at least one PERV-B.RBD ligand of the invention, a variant and/or fragment thereof.

In one embodiment, the kit of the invention further comprises cells displaying SMVT at the cell surface for use as a reference.

The present invention further relates to a method for the treatment of cancer in a subject, preferably of a SMVT-related cancer, more preferably of a cancer selected from the group consisting of liver cancer, prostate cancer, lung cancer, gallbladder cancer, pancreas cancer, colon cancer, ovarian cancer, brain cancer, kidney cancer, thyroid cancer, lymphomas, urothelial cancer, cervical cancer and endometrial cancer, comprising the steps of:
  a) diagnosing said cancer using an in vitro or in vivo method according to the invention for diagnosing a SMVT-related disease,
  b) treating said cancer, preferably by chemotherapy.

Examples of chemotherapies include, but are not limited to:
  a. alkylating agents that act mainly by forming covalent bonds between DNA bases, including, but not limited to, nitrogen mustards (e.g., cyclophosphamide), aziridines and epoxides (e.g., thiopeta), alkyl sulfonates (e.g., busulfan), nitrosureas (e.g., BCNU and CCNU), hydrazine and triazine derivatives (e.g., procarbazine and temozolomide);
  b. cisplatin and its analogs that act by forming DNA adducts which lead to intra-strand and inter-strand linking leading to the formation of DNA filaments, including, but not limited to, carboplatin, cisplatin and oxaliplatin;
  c. antimetabolites including but not limited to folate metabolism inhibitors (e.g., methotrexate, trimetrexate, tomudex), 5-fluoropyrimidines (e.g., 5-FU), oral fluoropyramidines (e.g., tegafur, uracil, capecitabine), necleoside analogs (e.g., cytarabine), gemcitabine and 6-thiopurines (e.g., 6-MP and 6-TG);
  d. topoisomerase-interactive agents that affect the topologic states of DNA by interfering or modulating DNA cleavage, strand passage and re-ligation, including, but not limited to, epipodophyllotoxins (e.g., etoposide and teniposide), camptothecin analogs, anthracyclines (e.g., doxorubicin, daunorubicin, epirubicin, idarubicin), mitoxantrone and losoxantrone, and dactinomycin;
  e. antimicrotubule agents, which interfere with the proper polymerization/depolymerization of microtubules, including, but not limited to, vinca alkaloids (e.g., vincristine, vinorelbine and vinblastine), taxanes (e.g., paclitaxel, docetaxel) and estramustine phosphate; and
  f. numerous miscellaneous agents exist which cannot be classified into any of the above groups, including but not limited to suramin, bleomycin, L-asparaginase and amifostine.

The present invention further relates to a method for the treatment of diseases characterized by a lower expression and/or function of SMVT in a subject, comprising the steps of:
  a) diagnosing said disease using an in vitro or in vivo method according to the invention for diagnosing a SMVT-related disease;
  b) treating said disease, preferably by a biotin, pantothenic acid and/or lipoic acid supplementation.

EXAMPLES

The present invention is further illustrated by the following examples.

Example 1: PERVB-RBD Automated Screen Identifies SLC5A6 as the PERVB-RBD Cognate Receptor Materials and Methods Three independent screenings for PERV-B-RBD (SEQ ID NO: 13) binding on a collection of 172 member of the Solute Carrier protein (SLC) family were performed with a Freedom-EVO® robot from Tecan with acquisition of images and fluorescence intensity parameters by Cellomics (Array Scan XTI HCS Thermo Scientific).

20 000 quail QT6 cells per well were seeded in a 96 well plate coated with poly-D-lysine. 24 hours later, cells were transfected with 100 ng of SLC expression vectors using JetPrime transfection reagent (Polypus Transfection 114-15) according to the manufacturer's instructions. QT6 cell were chosen as the spontaneous binding of the PERV-B.RBD ligand was the lowest among the cell lines considered and tested. Cells were washed the next day with PBS and incubated in fresh DMEM/FBS for 48 hours before binding assays. Binding assays were performed on transfected adherent cells that were washed with PBA (PBS with 2% FBS), incubated in 40 µl with either a saturating concentration of the PERV-B RBD ligand fused to a mouse Fc fragment (SEQ ID NO: 13), or a control supernatant, or a control RBD known to interact with a cognate SLC protein.

Incubation was carried on for 30 min at 37° C., before cells were washed twice with PBA, incubated with Alexa488-conjugated (Invitrogen) anti-mouse IgG1 antibody (1/500 dilution) at room temperature, washed twice with PBA and fixed with 1% paraformaldehyde (PFA). Transfection and binding assays were performed on the Freedom EVO robot (Tecan). Images and fluorescence intensity parameters were acquired by Cellomics (Array Scan XTI HCS, Thermo Scientific). Fluorescent signal was analyzed using GraphPad Prism 5.

Results and Conclusions

Among the collection of members of the Solute carrier (SLC) protein family, PERV-B.RBD ligand binds to SMVT/SLC5A6 (FIG. 1).

Example 2: Specificity of the Binding of PERV-B.RBD Ligand to SMVT/SLC5A6

Figure 2:
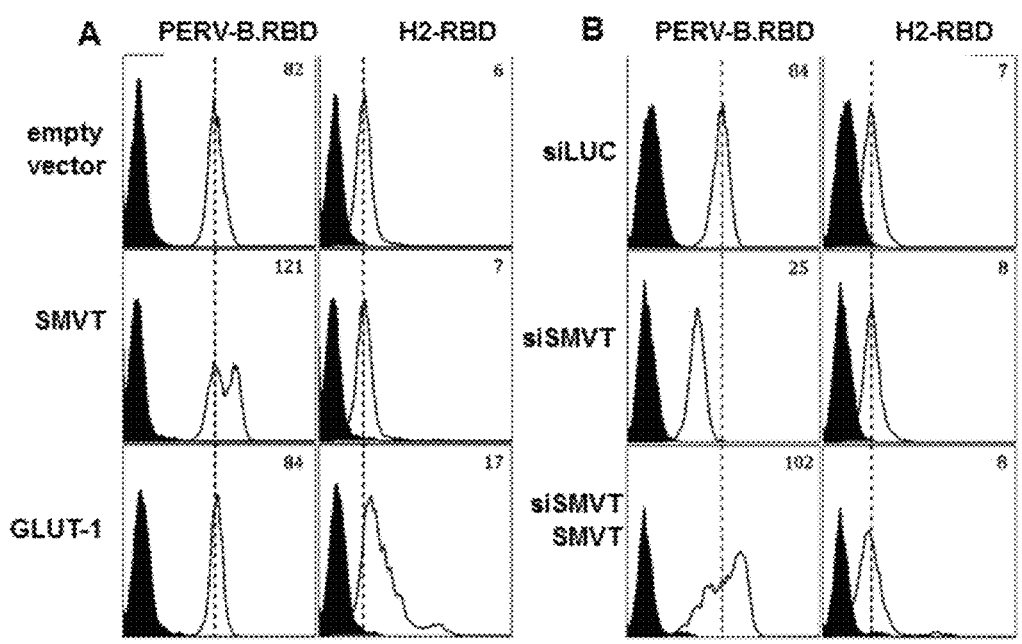
FIG. 2 is a set of graphs showing the specific PERV-B.RBD binding to SLC5A6/SMVT. A) HEK 293T cells were transfected with empty vector (pCHIX), a SMVT expression or a glucose transporter type 1 (GLUT-1) expression vector. B) HEK 293T cells were transfected with siRNAs directed against luciferase (siLUC, upper panels), SMVT (siSMVT) alone (central panels) or in combination with SMVT expression vector (siSMVT+SMVT, lower panels). SMVT expression level was monitored using PERV-B.RBD ligand (and GLUT-1 expression using human T-cell leukemia virus type 2 (HTLV2)-RBD (H2-RBD) by flow cytometry. Nonspecific staining (filled histograms) and specific binding (solid line histograms) are represented. The number of cells (count–y-axis) is plotted as a function of the fluorescence intensity (AU–x-axis). Relative specific binding of each RDB in the different conditions, expressed as the delta of the geometric mean of the fluorescence intensity between a specific binding and a nonspecific staining, is indicated in the upper right of each panel.

Material and Methods $5 \times 10^5$ HEK293T cells were seeded on a 6-well plate and transfected with a siRNA directed either against the firefly luciferase gene (siLUC, 5'-CUUACGCUGAGUAC-UUCGA-3'—SEQ ID NO: 15), or a siRNA directed against the SLC5A6 gene (siSMVT, 5'-GGAUGAGUCUUGGU-GUGUUTT-3'—SEQ ID NO: 16). Forty-eight hours post-transfection, cells were detached with 1 mM EDTA in PBS. For the binding assay, $1 \times 10^5$ cells were resuspended in 100 µl of PBA (PBS with 2%1-BS) containing a saturating concentration of either the PERV-B.RBD (SEQ ID NO: 13), or the human T-cell leukemia virus type 2 (HTLV2)-RBD known to bind SLC2A1/GLUT1, and incubated at 37° C. for 30 min Cells were then washed twice with 100 µl of PBA, incubated with Alexa488-congugated anti-mouse IgG1 at 4° C. for 20 min, washed twice and resuspended in 200 µl of PBA. The results were acquired by flow cytometry on a FACSCalibur (Becton Dickinson) and analyzed by FlowJo. Nonspecific staining with no RBD (filled histograms) and specific binding of the RBD (solid line histograms) are represented as delta of the geometric mean of the fluorescence intensity between a specific binding and a nonspecific staining. HEK 293T cells were transfected as above with either the empty vector (pCHIX, "vecteur vide"), the SMVT expression vector (SMVT), or the GLUT-1 expression vector. All were tested with PERV-B.RBD (SEQ ID NO: 13) or HTLV2-RBD, the latter known to bind SLC2A1/GLUTE Results and Conclusion The binding of the PERV-B.RBD ligand increased specifically when cells overexpressed SMVT (FIG. 2A) and decreased specifically in cell underexpressing SMVT (FIG. 2B). The PERV-B.RBD thus binds specifically to SMVT/SLC5A6, allowing it use in the diagnosis of disease characterized by a variation of SMVT expression.

Example 3: Specificity of the Binding of PERV-B.RBD Ligand to SMVT/SLC5A6, as Assessed with a Second Anti-SMVT siRNA Material and Methods $5 \times 10^5$ HEK293T cells were seeded on a 6-well plate and transfected with a siRNA directed either against the firefly luciferase gene (siLUC, 5'-CUUACGCUGAGUAC-UUCGA-3'—SEQ ID NO: 15), or a siRNA directed against the SLC5A6 gene and different from the siRNA used in Example 2 (siSMVT A, 5'GCAGGAU-CAUGCCAGAAAUTT-3'—SEQ ID NO: 23). Forty-eight hours post-transfection, cells were detached with 1 mM EDTA in PBS. For the binding assay, $1 \times 10^5$ cells were resuspended in 100 µl of PBA (PBS with 2% FBS) containing a predetermined saturating concentration of either the PERV-B.RBD (SEQ ID NO: 13), or a RBD from a xenotropic murine retrovirus (XRBD), whose receptor is known to be XPR1/SLC53A1, or the HTLV2-RBD (H2), whose receptor is known to be GLUT1/SLC2A1, or a RBD derived from the bovine leukemia virus (BLV), whose receptor is known to be CAT1/SLC7A1, or a control supernatant preparation with no RBD (MOCK), followed by an incubation at 37° C. for 30 min. All RBD were produced as fusion proteins with mFC (PERV-B.RBD, XRBD, BLV-RBD and HTLV2-RBD). Cells were then washed twice with 100 µl of PBA, incubated with Alexa488-congugated anti-mouse IgG1 at 4° C. for 20 min, and washed twice and resuspended in 200 µl of PBA. The results were acquired by flow cytometry on a FACSCalibur (Becton Dickinson) and analyzed by FlowJo. Relative specific binding of each RDB in the different conditions, expressed as the delta of the geometric mean of the fluorescence intensity between a specific binding and a nonspecific staining.

Results and Conclusion

Figure 3:
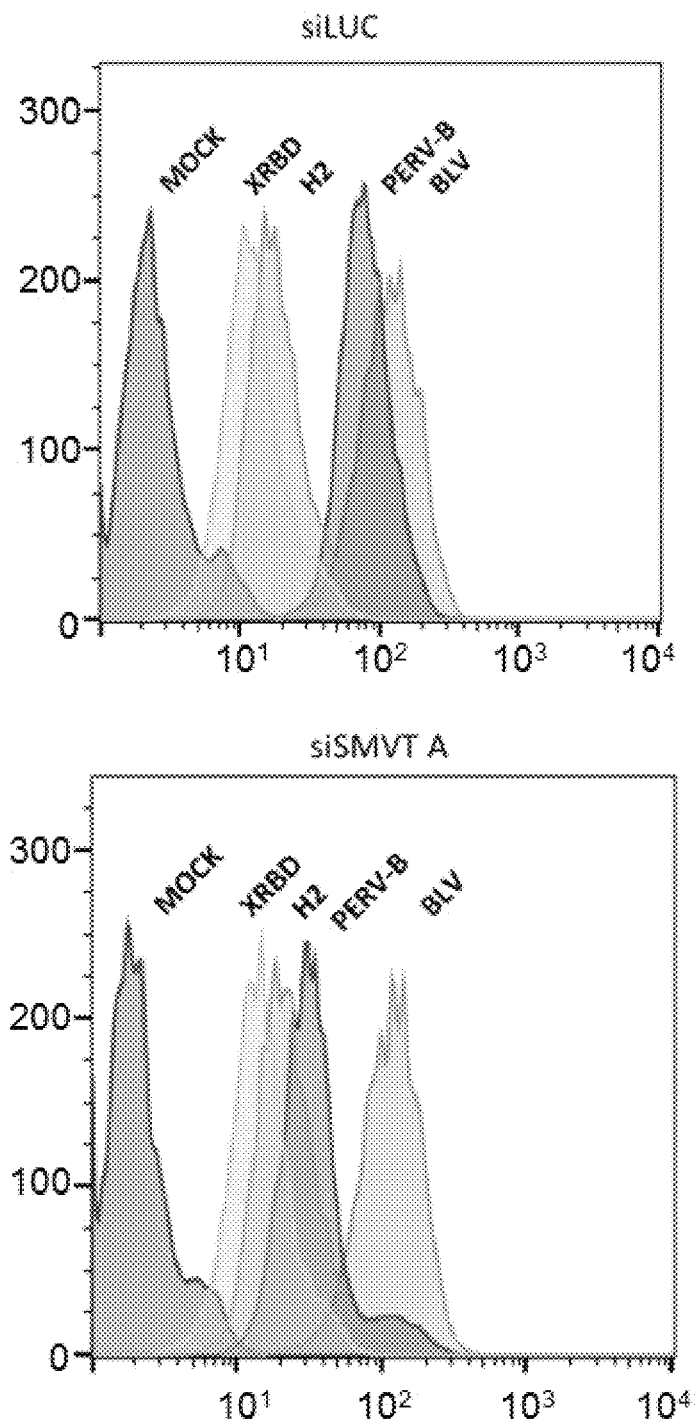
FIG. 3 is a set of graphs confirming the specific PERV-B.RBD binding to SLC5A6/SMVT using a second siSMVT siRNA. HEK 293T cells were transfected with either a siLUC control siRNA (siLUC) (upper panel), or an anti-SMVT siRNA (siSMVT) (lower panel). Variation of relative binding of different RBD ligands was compared by flow cytometry in these two conditions. RBD ligands included a control supernatant preparation with no RBD (MOCK), or a preparation of either PERV-B.RBD (PERV-B), or a RBD from a xenotropic murine retrovirus (XRBD), whose receptor is known to be XPR1/SLC53A1, or the HTLV2-RBD (H2), whose receptor is known to be GLUT1/SLC2A1, or a RBD derived from the bovine leukemia virus (BLV), whose receptor is known to be CAT1/SLC7A1. The number of cells (count-y-axis) is plotted as a function of the fluorescence intensity (AU-x-axis).

Specific binding of the PERV-B.RBD ligand decreased significantly when cells where treated with anti-SMVT siRNA, with a drop of over 2-fold (77.5 to 34, FIG. 3 and table 1). Specific drop of PERV-B.RBD binding observed upon introduction of siSMVT was assessed as binding of XRBD, H2-RBD or BLV-RBD did not vary significantly between siLUC (FIG. 3 left panel) and siSMVT treatment (FIG. 3 right panel). This confirmed that PERV-B.RBD binds specifically to SMVT/SLC5A6, allowing it use in the diagnosis of disease characterized by a variation of SMVT expression.

TABLE 1

Relative binding of each RBD preparation and the control (MOCK) is expressed Relative specific binding of each RDB in the different conditions, expressed as the delta of the geometric mean of the fluorescence intensity between a specific binding and a nonspecific staining.

| Ligand | siLUC | siSMVT A |
| --- | --- | --- |
| MOCK | 2.6 | 2.2 |
| PERV-B.RBD | 77.5 | 34.0 |
| XRBD | 12.6 | 14.6 |
| HTLV2-RBD | 18.3 | 21.3 |
| BLV-RBD | 110.0 | 110.0 |

Example 4: PERV-B.RBD Ligand Allows the Detection of Variations of the Expression of SMVT at the Surface of Cancer Cells Materials and Methods For the binding assay, $1 \times 10^5$ cells of each cell type were resuspended in 100 µl of PBA (cell density of $1 \times 10^6$ per mL) containing a saturating concentration of either the PERV-B-RBD (SEQ ID NO: 13), and incubated at 37° C. for 30 min. Cells were washed twice with 100 µl of PBA, incubated with PE-conjugated anti-mouse IgG1 at 4° C. for 20 min, washed twice and resuspended in 200 µl of PBA. The results were acquired by flow cytometry on a FACS verse (Becton Dickinson) and analyzed with the FlowJo software (FLOWJO, LLC). Relative specific binding of PERV-B.RBD to the different cells is expressed as the delta of the geometric mean of the fluorescence intensity between a specific binding and a nonspecific staining.

Results and Conclusions

The binding of PERV-B.RBD to the surface of the cells was expressed in terms of the mean signal to noise ratio, for each cell type. Most cancer cell lines displayed a signal to noise ratio over 100 (table 2).

The results indicate that variations of expression level of SMVT, are indicative of cancer.

TABLE 2

Expression of SMVT in different human cancer cell lines. Bold font distinguishes cells of cancerous origin. Relative specific binding of PERV-B.RBD to the different cells is expressed as the delta of the geometric mean of the fluorescence intensity between a specific binding and a nonspecific staining.

| Cell type | Specific PERV-B.RBD binding |
|---|---|
| RS4; 11 (lymphoma cell line, B-type) | 6 |
| Cardiomyocytes (ES-derived) | 12 |
| Primary hepatocytes | 14 |
| hMSC (hES-derived) | 16 |
| IC8LC10 (Lung, NSCLC cell line) | 16 |
| Circulating granulocytes | 20 |
| HID28-1 (Prostate, adenocarcinoma cell line) | 30 |
| RCC-49 (Kidney, carcinoma cell line) | 37 |
| SU-DHL6 (lymphoma cell line) | 47 |
| GBM14-CHA (Brain, gliobastoma cell line) | 55 |
| HEK-293T | 64 |
| Red blood cells | 70 |
| Circulating lymphocytes | 81 |
| Circulating monocytes | 106 |
| OVA2-BUR (Ovarian - Adenocarcinoma cell line) | 111 |
| KP4 (Pancreas, ductal cell carcinoma cell line) | 118 |
| T84 (colorectal carcinoma cell line) | 120 |
| MIA PaCa-2 (Pancreas, carcinoma cell line) | 173 |
| TC122a (Colon - carcinoma cell line) | 175 |
| AsPC1 (Pancreas, adenocarcinoma cell line) | 202 |
| Mz-ChA-1 (Gallbladder, carcinoma cell line) | 242 |
| Mz-ChA-2 (Gallbladder, carcinoma cell line) | 248 |
| IC20-DAN (Lung, NSCLC cell line) | 250 |
| HID28-2 (Prostate, adenocarcinoma cell line) | 266 |
| HepG2 (Liver, hepatocellular carcinoma cell line) | 343 |

---

The invention claimed is:

1. An in vitro method for detecting and/or measuring the level of sodium-dependent multivitamin transporter (SMVT) in a biological sample, wherein said method comprises the steps of:

a. contacting said biological sample with a PERV-B.RBD ligand, which is a receptor binding domain (RBD) ligand isolated from an envelope protein of porcine endogenous retrovirus type B (PERV-B), a variant and/or a fragment; and, b. detecting and/or measuring the binding of said PERV-B.RBD ligand, variant and/or fragment to SMVT, wherein said PERV-B.RBD ligand comprises a sequence consisting of the sequence SEQ ID NO: 6, a variant and/or fragment, wherein said variant presents a sequence identity of at least 90% with the sequence SEQ ID NO: 6, wherein said fragment is a fragment of the sequence SEQ ID NO: 6 or of said variant, and wherein said variant and/or fragment binds to SMVT.

2. The in vitro method according to claim 1, wherein said method further comprises comparing the binding level measured at step b. with a reference value.

3. The in vitro method according to claim 1, wherein the amino acid sequence of said PERV-B.RBD ligand, variant and/or fragment comprises or consists of an amino acid sequence selected from the group consisting of the amino acid sequences SEQ ID NO: 6, SEQ ID NO: 20, SEQ ID NO: 22, variants thereof, and/or fragments thereof.

4. The in vitro method according to claim 1, wherein said PERV-B.RBD ligand, variant and/or fragment thereof is labeled with a detectable label.

5. The in vitro method according to claim 1, wherein said method is for diagnosing a SMVT-related disease in a subject or for identifying a subject as being at risk of developing a SMVT-related disease.

6. The in vitro method according to claim 5, wherein said SMVT-related disease is cancer.

7. The in vitro method according to claim 5, wherein said SMVT-related disease is a neuroinflammatory disease.

8. The in vitro method according to claim 5, wherein said SMVT-related disease is a disorder of pregnancy.

9. The in vitro method according to claim 5, wherein said SMVT-related disease is an infectious disease.

10. The in vitro method according to claim 6, wherein said cancer is selected from the group consisting of liver cancer, prostate cancer, lung, cancer, gallbladder cancer, pancreas cancer, colon cancer, ovarian cancer, brain cancer, kidney cancer, thyroid cancer and lymphomas.

11. The in vitro method according to claim 7, wherein said neuroinflammatory disease is multiple sclerosis.

12. The in vitro method according to claim 8, wherein said disorder of pregnancy is pre-eclampsia or intrauterine growth retardation.

13. The in vitro method according to claim 9, wherein said infectious disease is caused by a bacterium.

14. The in vitro method according to claim 13, wherein said infectious disease is caused by a bacterium belonging to the order Enterobacteriales.

* * * * *